United States Patent
Folzenlogen et al.

(10) Patent No.: US 11,766,306 B2
(45) Date of Patent: Sep. 26, 2023

(54) CRANIAL GUIDE FOR AN INTRACRANIAL MEDICAL PROCEDURE

(71) Applicant: THE REGENTS OF THE UNIVERSITY OF COLORADO, A BODY CORPORATE, Denver, CO (US)

(72) Inventors: Zach Folzenlogen, Denver, CO (US); Joshua Seinfeld, Denver, CO (US); Joshua Buehler, Arvada, CO (US); Talia Cioth, Denver, CO (US); Joshua Dwernychuk, Boulder, CO (US); Nico Andresen, Boulder, CO (US); Adam Jung, Colorado Springs, CO (US); Gilang Manurung, Lafayette, CO (US); Hao Yuan, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 957 days.

(21) Appl. No.: 16/620,678

(22) PCT Filed: Jun. 11, 2018

(86) PCT No.: PCT/US2018/036850
§ 371 (c)(1),
(2) Date: Dec. 9, 2019

(87) PCT Pub. No.: WO2018/231686
PCT Pub. Date: Dec. 20, 2018

(65) Prior Publication Data
US 2020/0170748 A1 Jun. 4, 2020

Related U.S. Application Data

(60) Provisional application No. 62/518,103, filed on Jun. 12, 2017.

(51) Int. Cl.
*A61B 90/10* (2016.01)
*A61B 90/11* (2016.01)
(Continued)

(52) U.S. Cl.
CPC .......... *A61B 90/10* (2016.02); *A61B 17/3423* (2013.01); *A61B 90/11* (2016.02);
(Continued)

(58) Field of Classification Search
CPC ........ A61B 17/3423; A61B 2017/3445; A61B 2017/3449; A61B 2017/3458;
(Continued)

(56) References Cited

U.S. PATENT DOCUMENTS 3,115,140 A 12/1963 Volkman
4,328,813 A 5/1982 Ray
(Continued)

OTHER PUBLICATIONS

PCT; International Search Report and Written Opinion dated Aug. 28, 2018 in Application No. PCT/US2018/036850.

*Primary Examiner* — Martin T Ton
(74) *Attorney, Agent, or Firm* — Nicholas Pfeifer; Smith & Hopen, P. A.

(57) ABSTRACT

The present disclosure relates to an intracranial guide for use in a medical procedure, such as to evacuate a subdural hematoma or to relieve an intracerebral hemorrhage. The intracranial guide generally includes a guide cannula to be received within a portion of a cranial port. The cranial port is configured to be anchored in a burr hole to be formed in the patient's cranium. The guide cannula includes at least one channel that may be used to guide a catheter to a targeted portion of the patient's anatomy or to apply a suction force within the patient's cranium.

16 Claims, 42 Drawing Sheets

(51) Int. Cl.
*A61B 17/34* (2006.01)
*A61B 90/00* (2016.01)
*A61B 17/00* (2006.01)

(52) U.S. Cl.
CPC ............. *A61B 2017/00526* (2013.01); *A61B 2017/3458* (2013.01); *A61B 2090/103* (2016.02); *A61B 2090/3983* (2016.02)

(58) Field of Classification Search
CPC ... A61B 2017/347; A61B 90/11; A61B 90/14; A61M 2039/025
See application file for complete search history.

(56) References Cited

U.S. PATENT DOCUMENTS

| | | | | |
|---|---|---|---|---|
| 4,681,103 | A | | 7/1987 | Boner et al. |
| 4,809,694 | A | * | 3/1989 | Ferrara .............. A61B 17/3403 606/130 |
| 5,279,575 | A | * | 1/1994 | Sugarbaker ........ A61B 17/3403 606/1 |
| 6,044,304 | A | | 3/2000 | Baudino |
| 6,623,490 | B1 | | 9/2003 | Crane et al. |
| 7,658,879 | B2 | | 2/2010 | Solar |
| 7,981,120 | B2 | | 7/2011 | Mazzocchi et al. |
| 8,308,781 | B2 | | 11/2012 | Wilson et al. |
| 9,020,606 | B2 | | 4/2015 | Yin |
| 9,033,990 | B2 | | 5/2015 | Iannotti et al. |
| 9,226,735 | B2 | | 1/2016 | Pretre et al. |
| 9,408,629 | B2 | | 8/2016 | Flint |
| 2006/0020241 | A1 | * | 1/2006 | Piskun ............... A61B 17/3421 604/93.01 |
| 2006/0192319 | A1 | * | 8/2006 | Solar ..................... A61B 90/11 264/271.1 |
| 2009/0326519 | A1 | * | 12/2009 | Wilson .............. A61M 39/0247 606/1 |
| 2010/0312063 | A1 | * | 12/2010 | Hess .................. A61B 17/3423 600/204 |
| 2016/0193008 | A1 | | 7/2016 | Gale et al. |

* cited by examiner

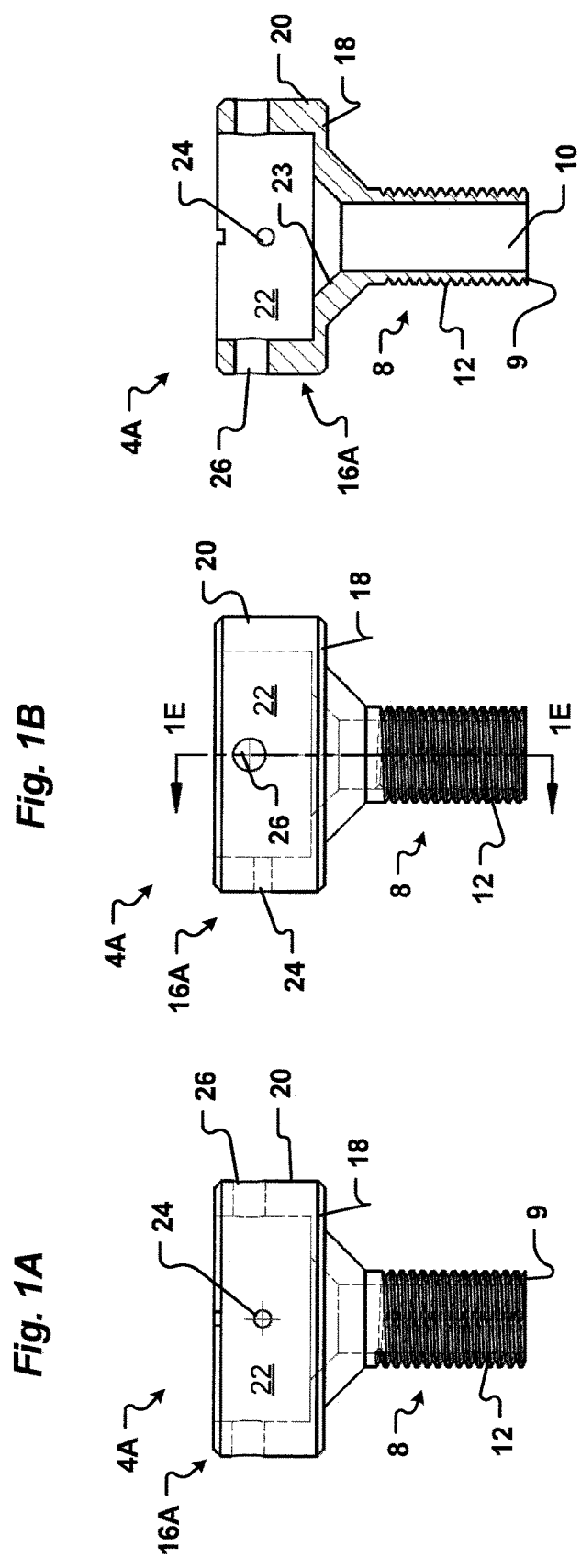
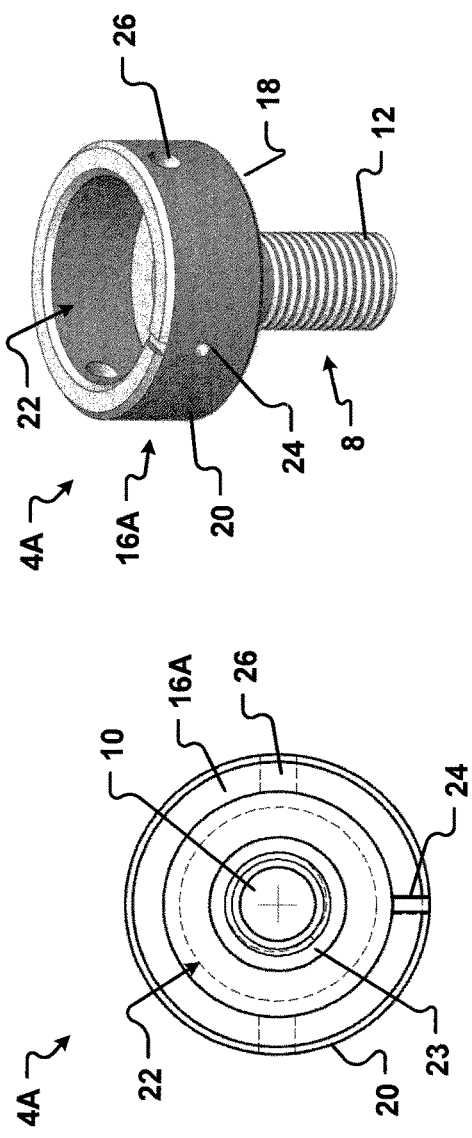

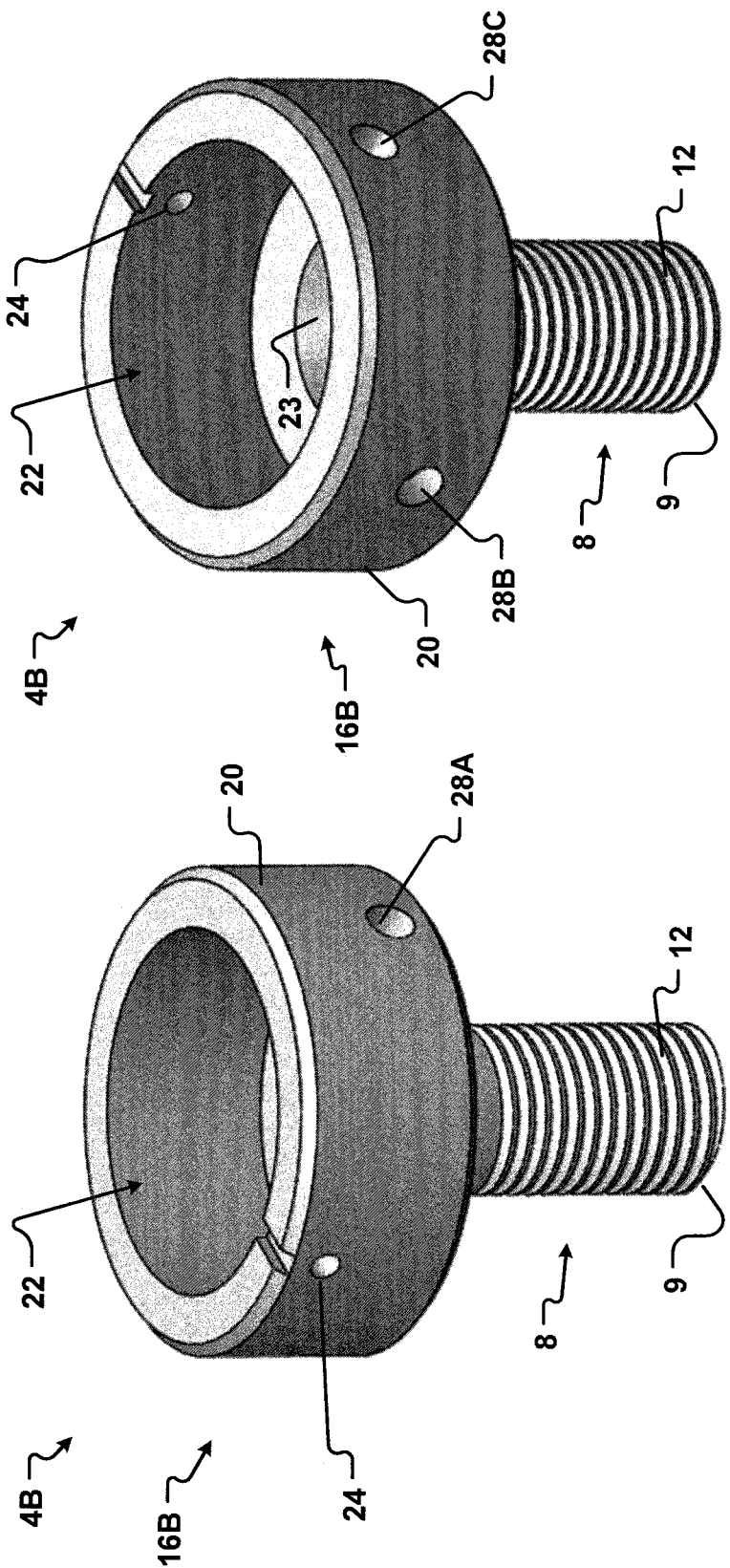

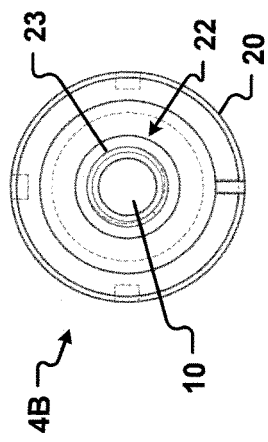
Fig. 3A
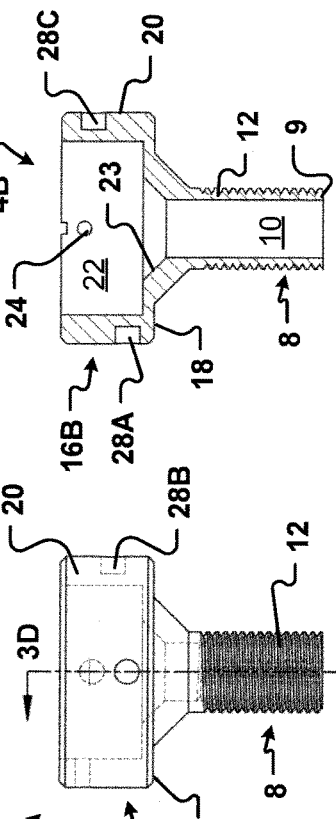
Fig. 3B
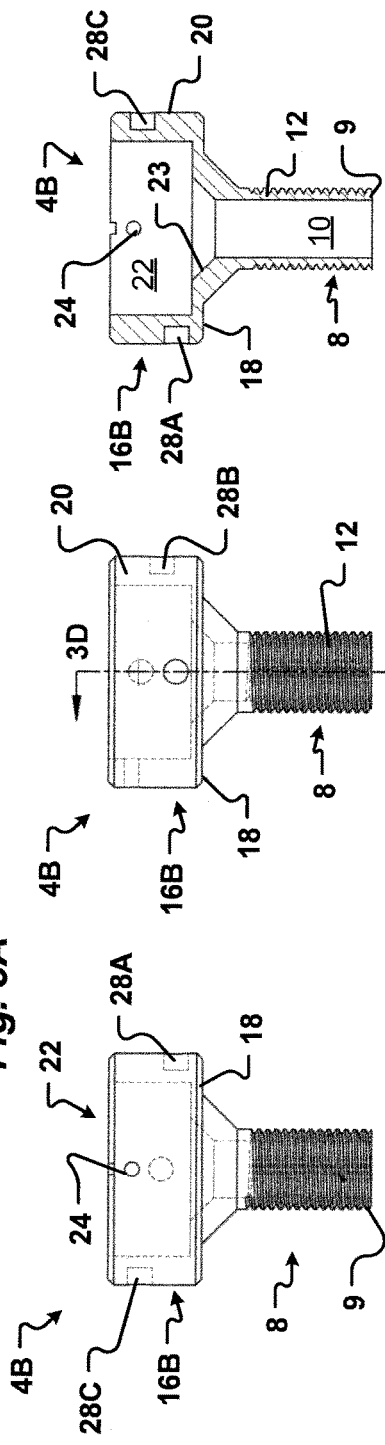
Fig. 3C
Fig. 3D
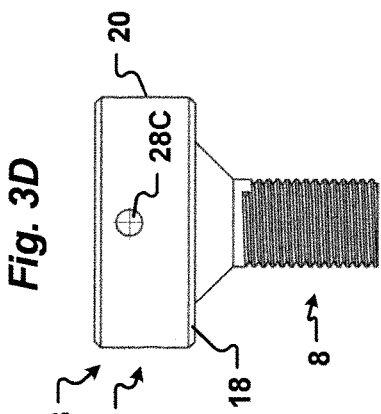
Fig. 3E
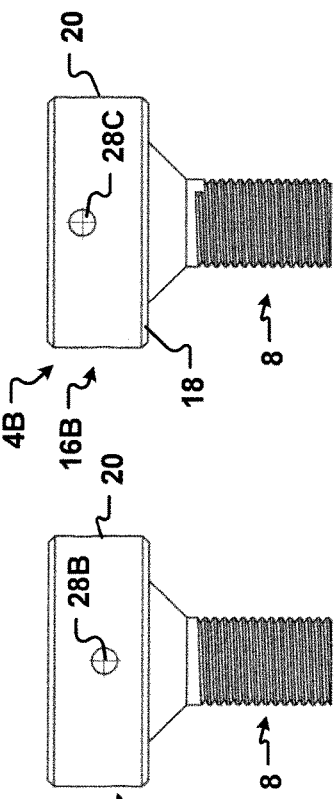
Fig. 3F
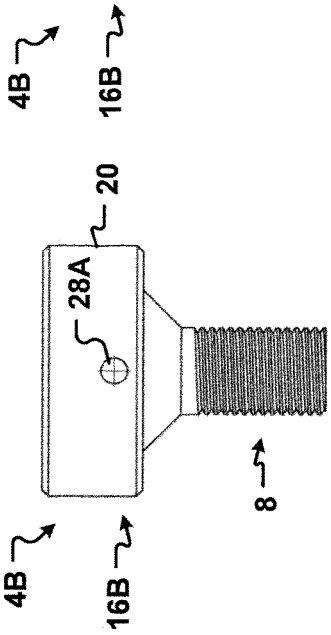
Fig. 3G

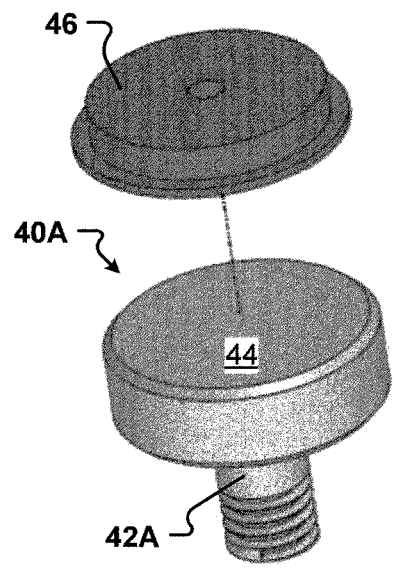
*Fig. 6A*
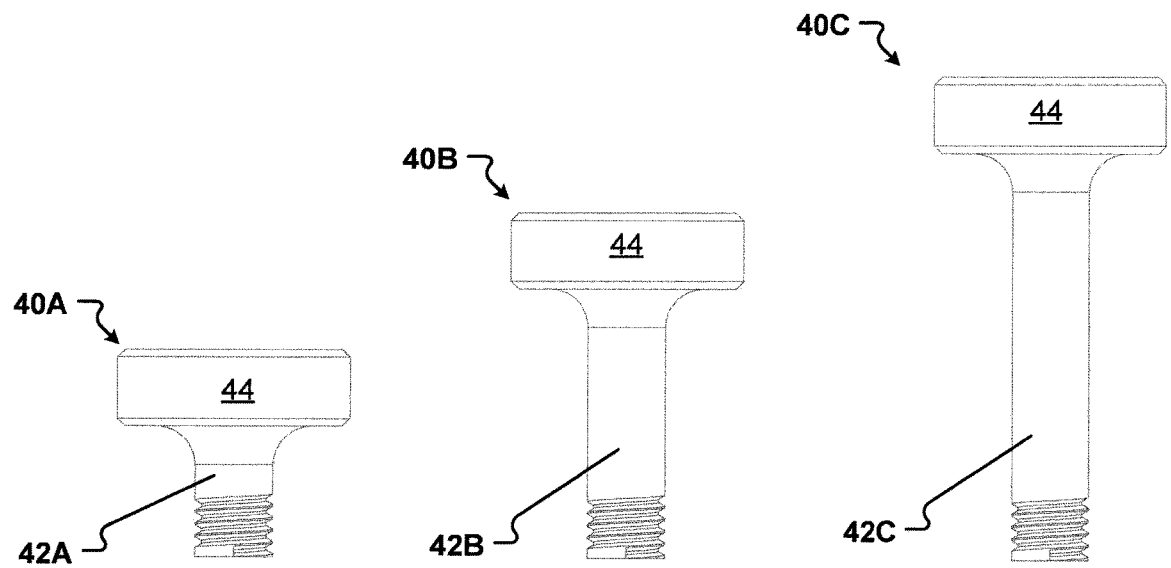
*Fig. 6B*     *Fig. 6C*     *Fig. 6D*

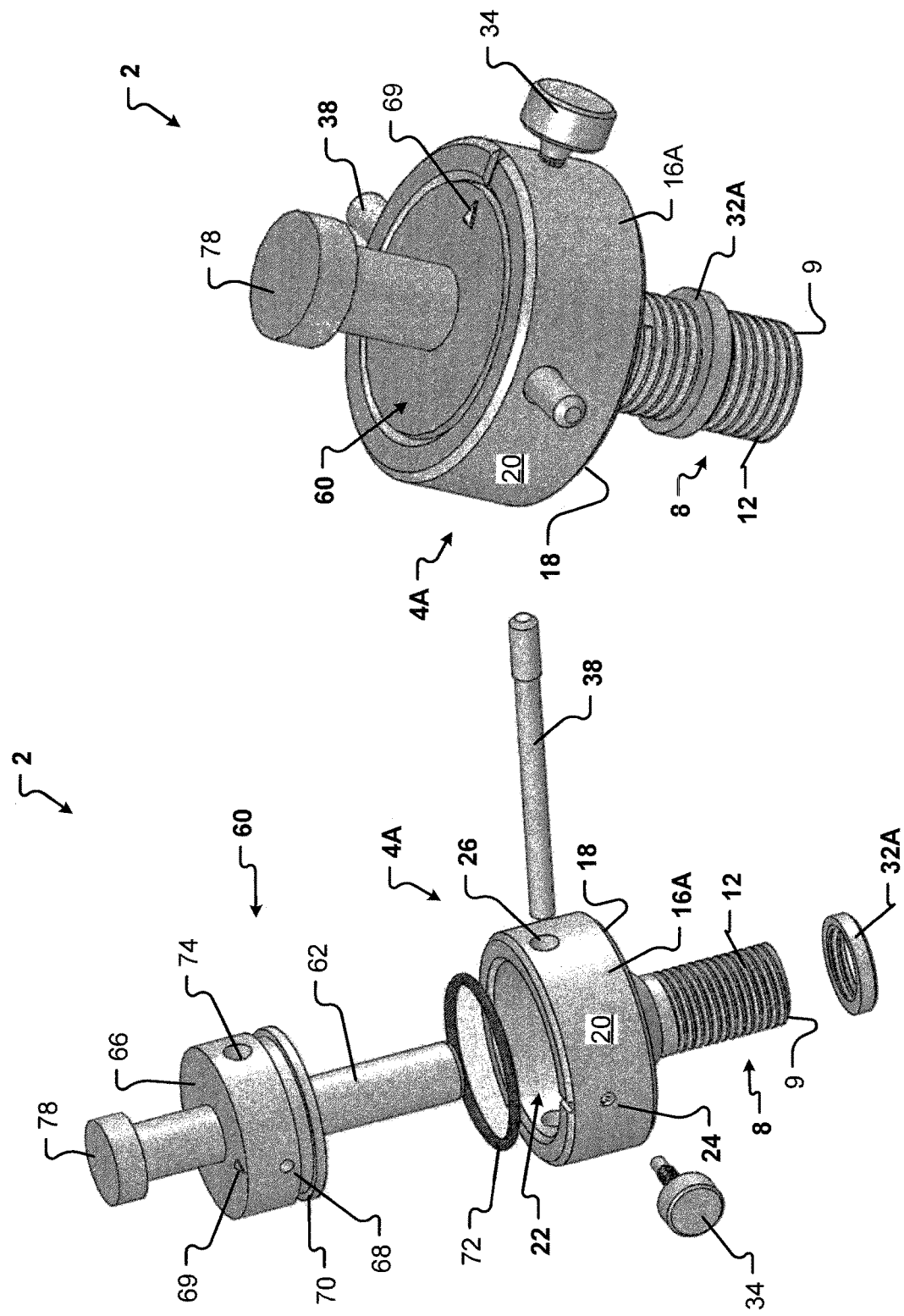

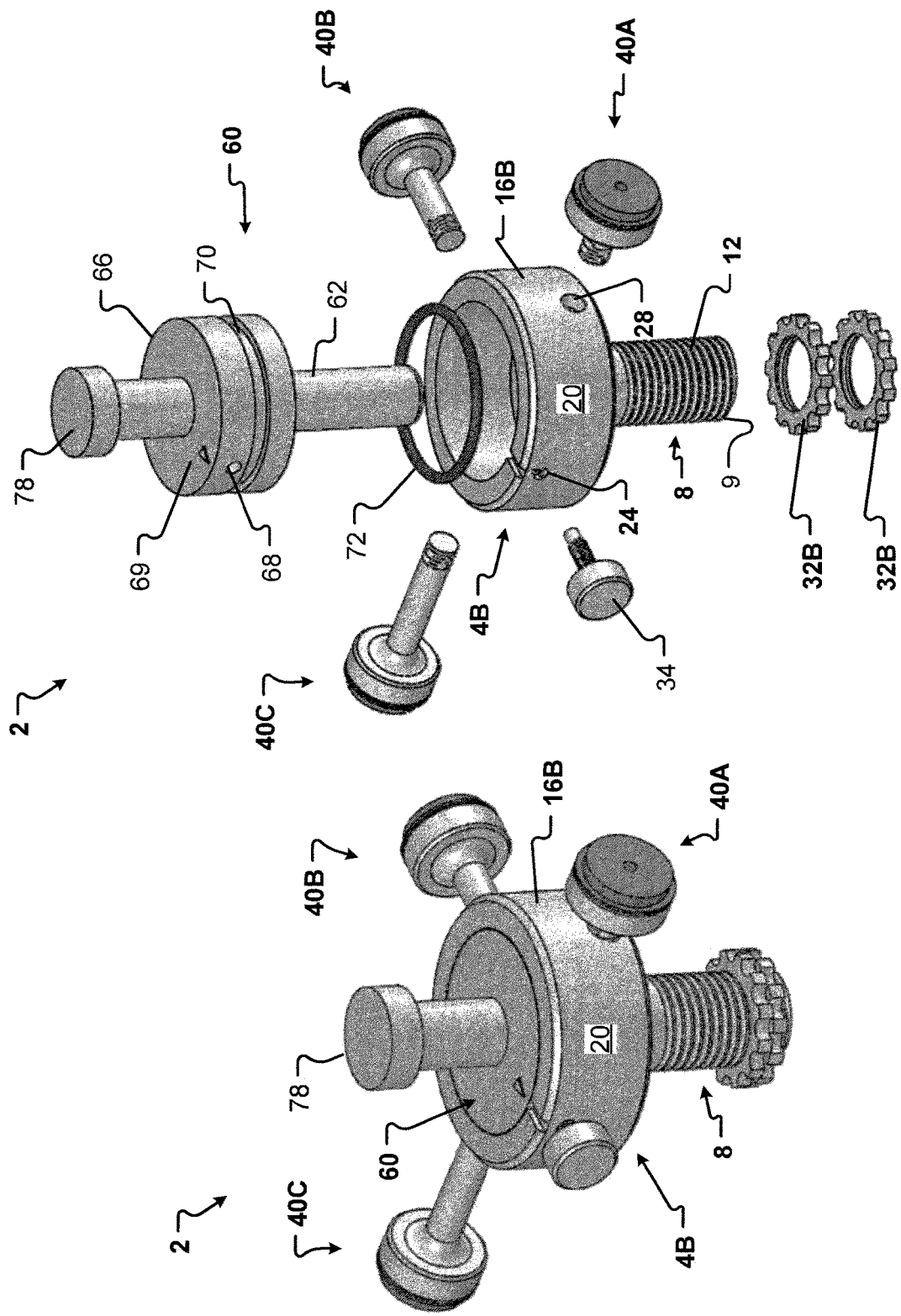

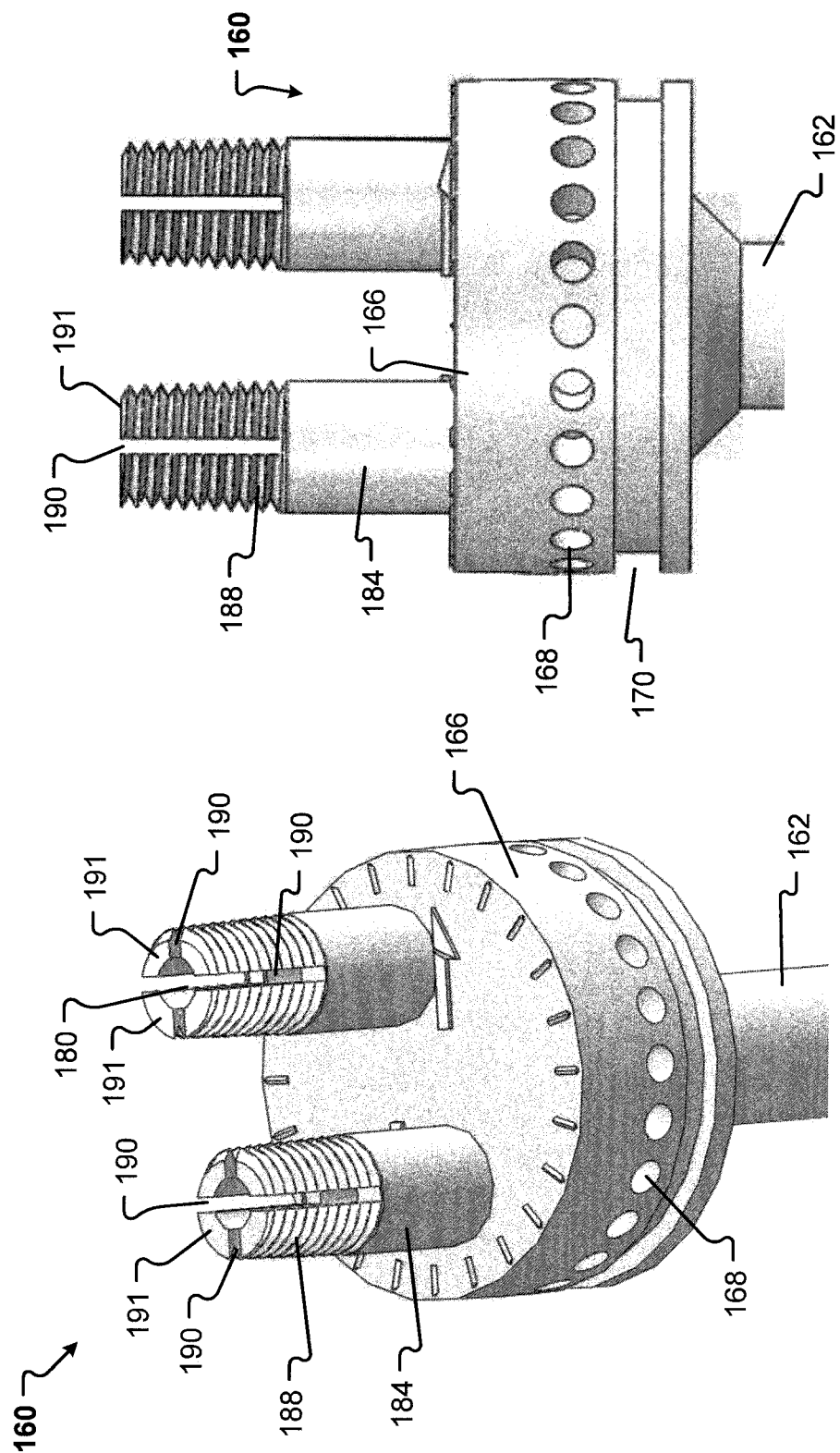

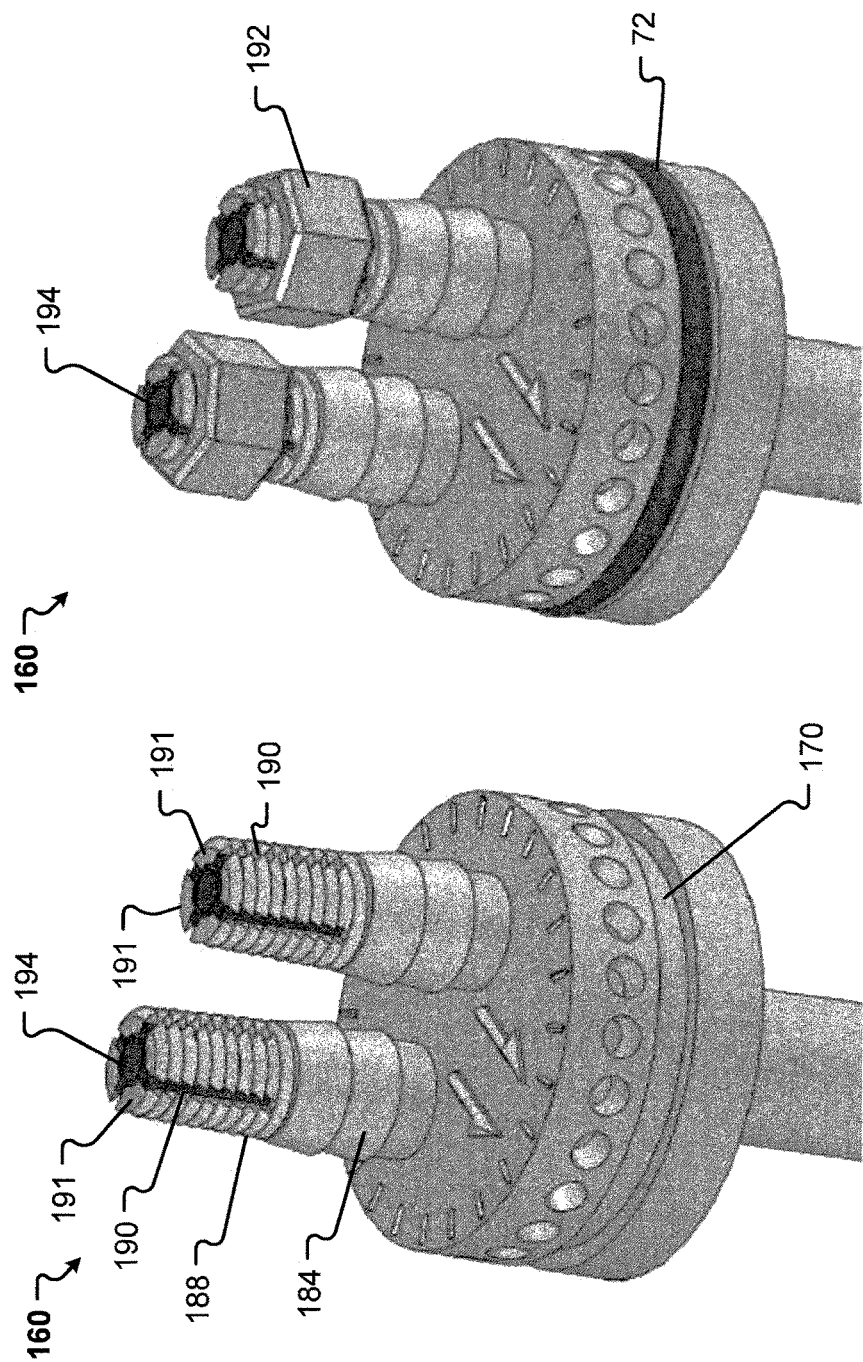

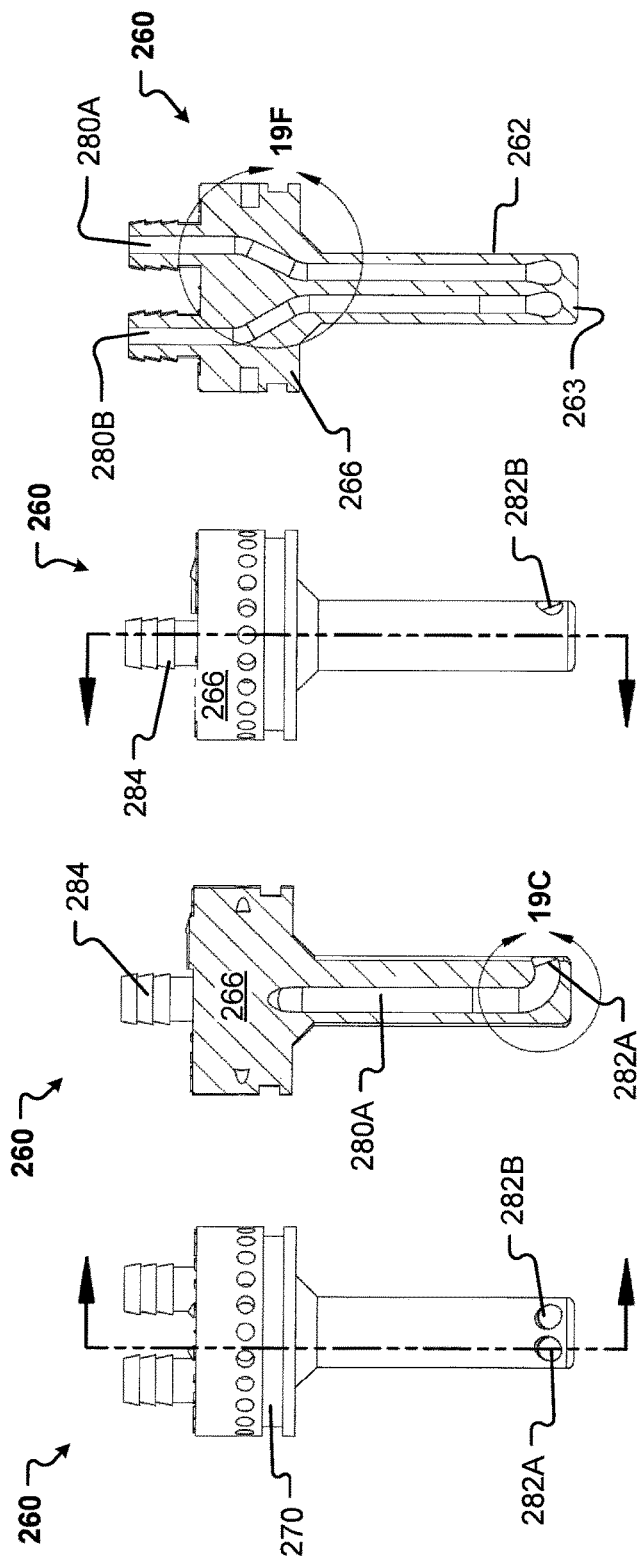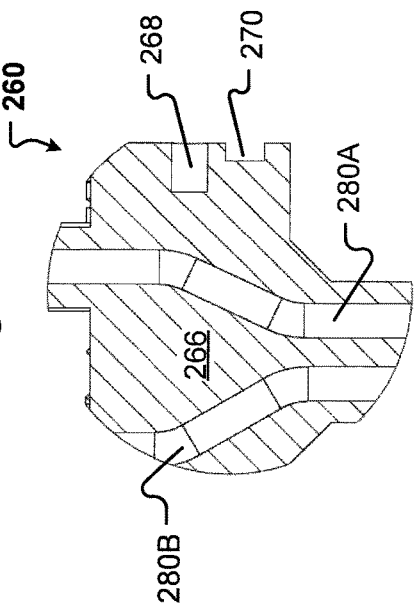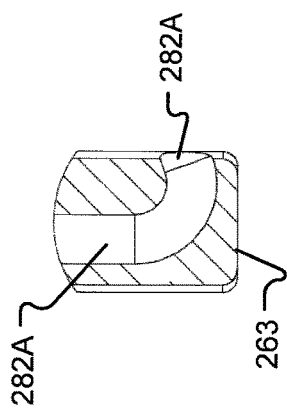

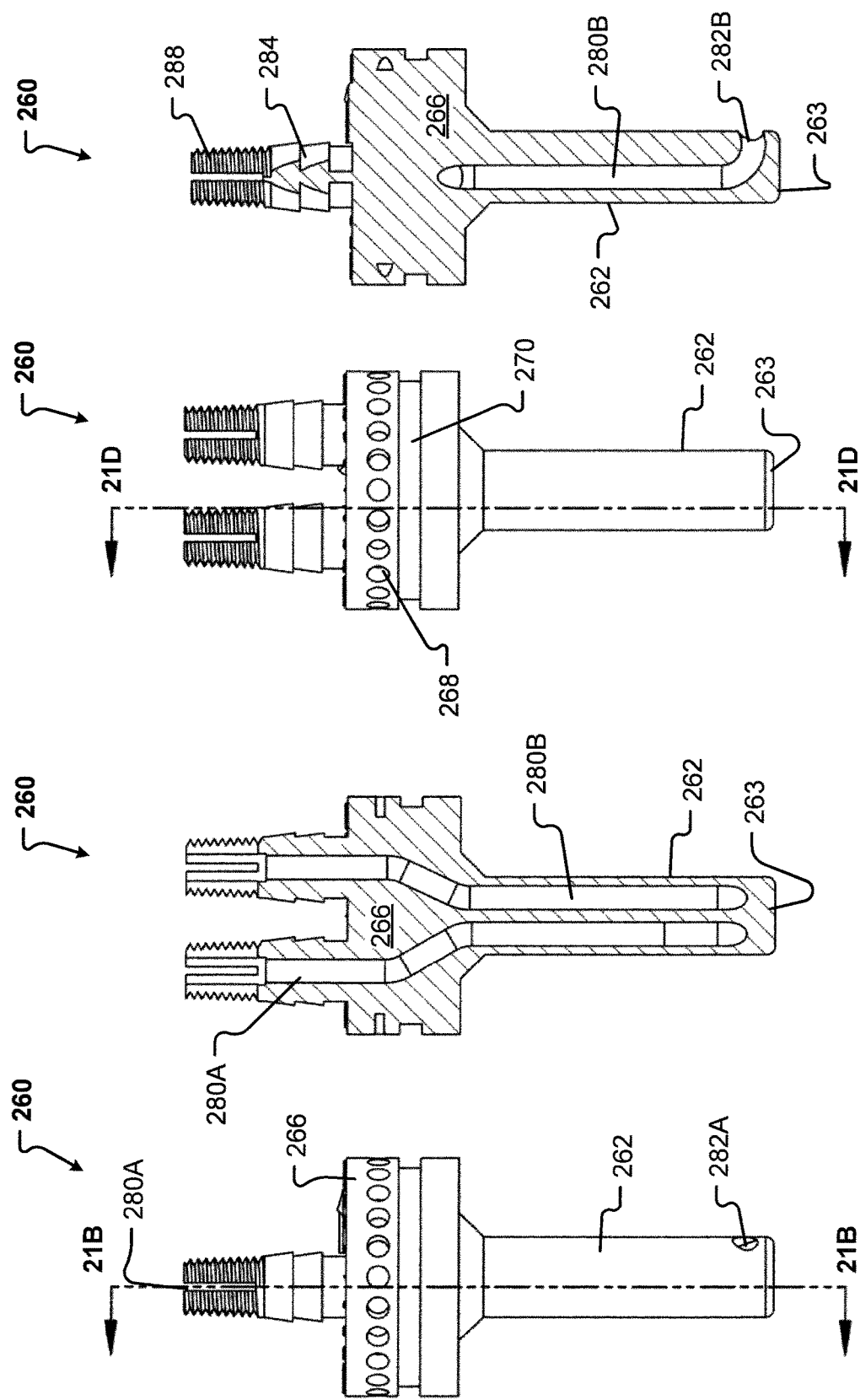

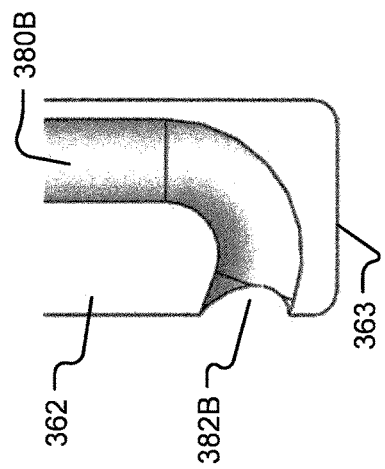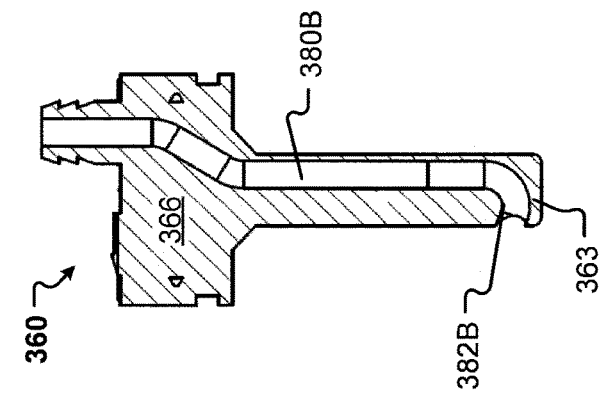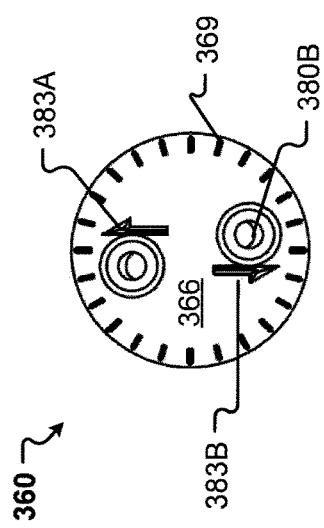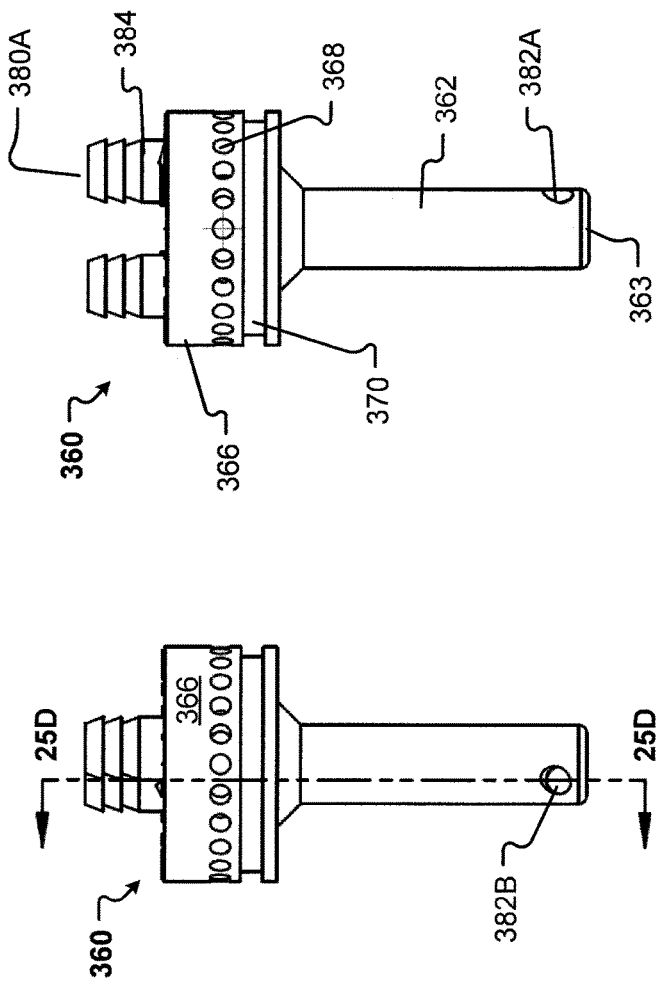

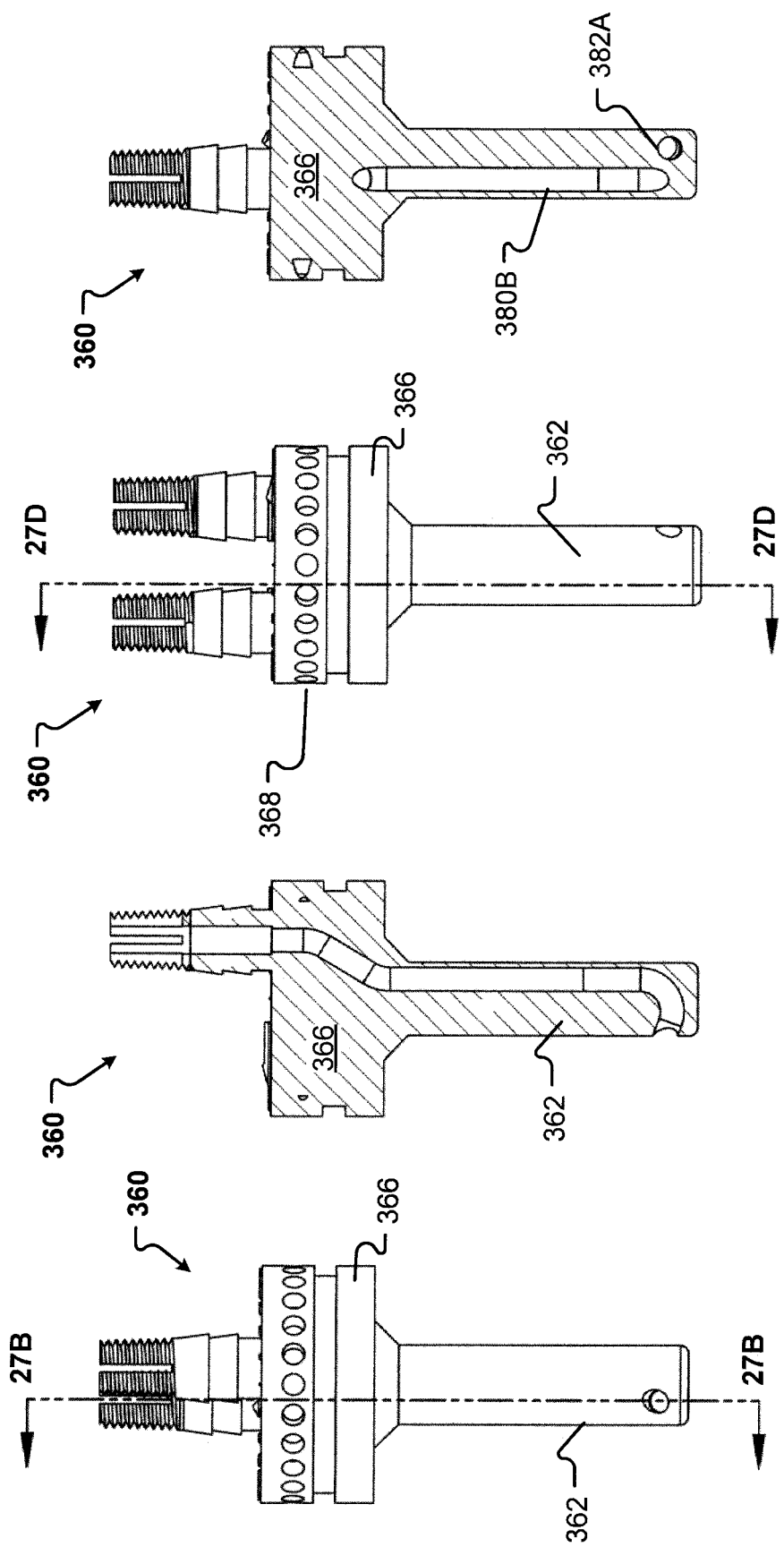

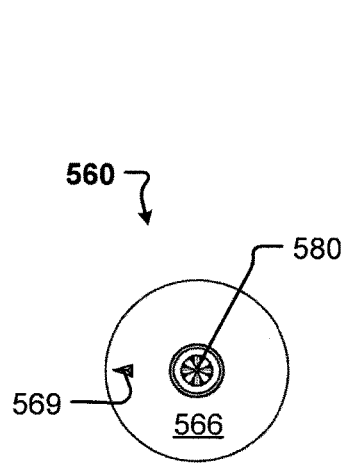
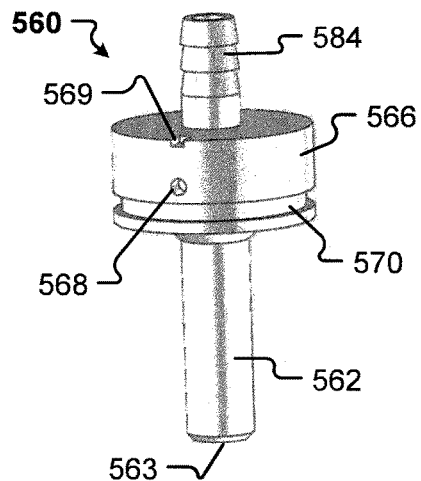
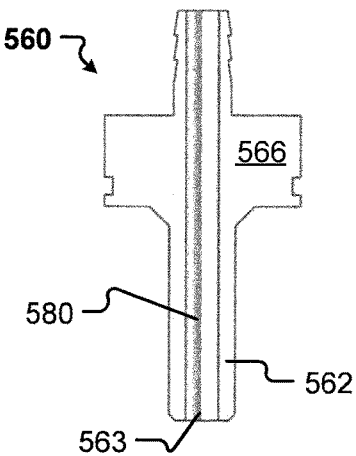
Fig. 29A  Fig. 29B  Fig. 29C
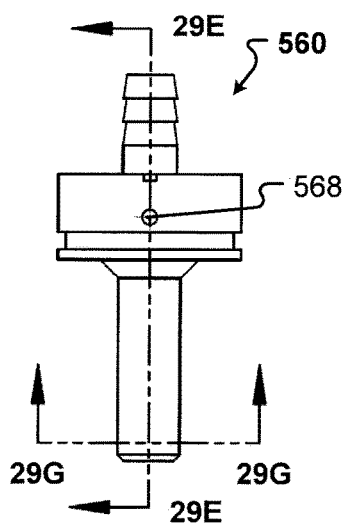
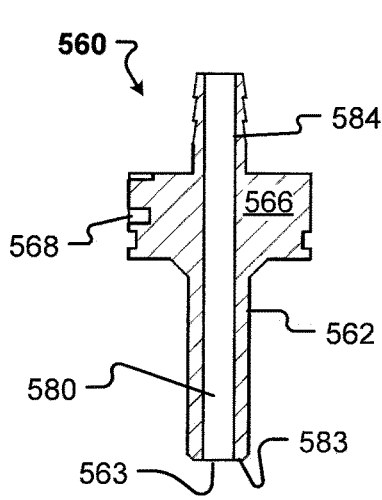
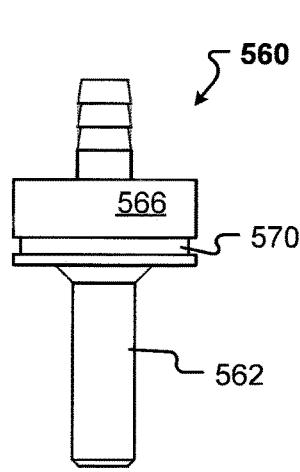
Fig. 29D  Fig. 29E  Fig. 29F
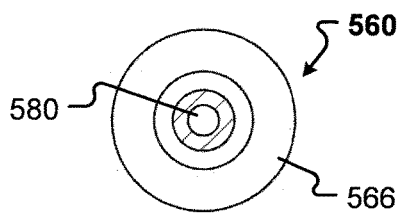
Fig. 29G

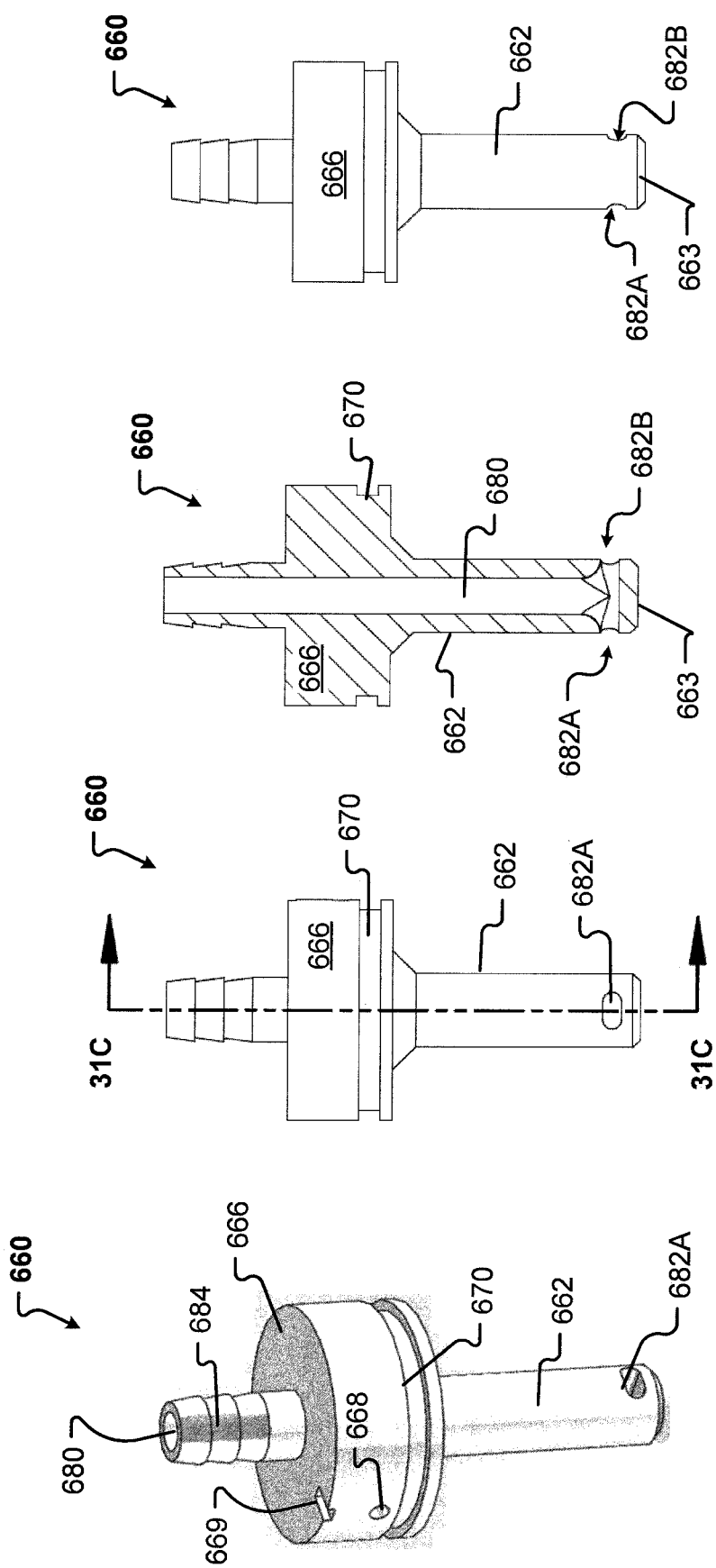

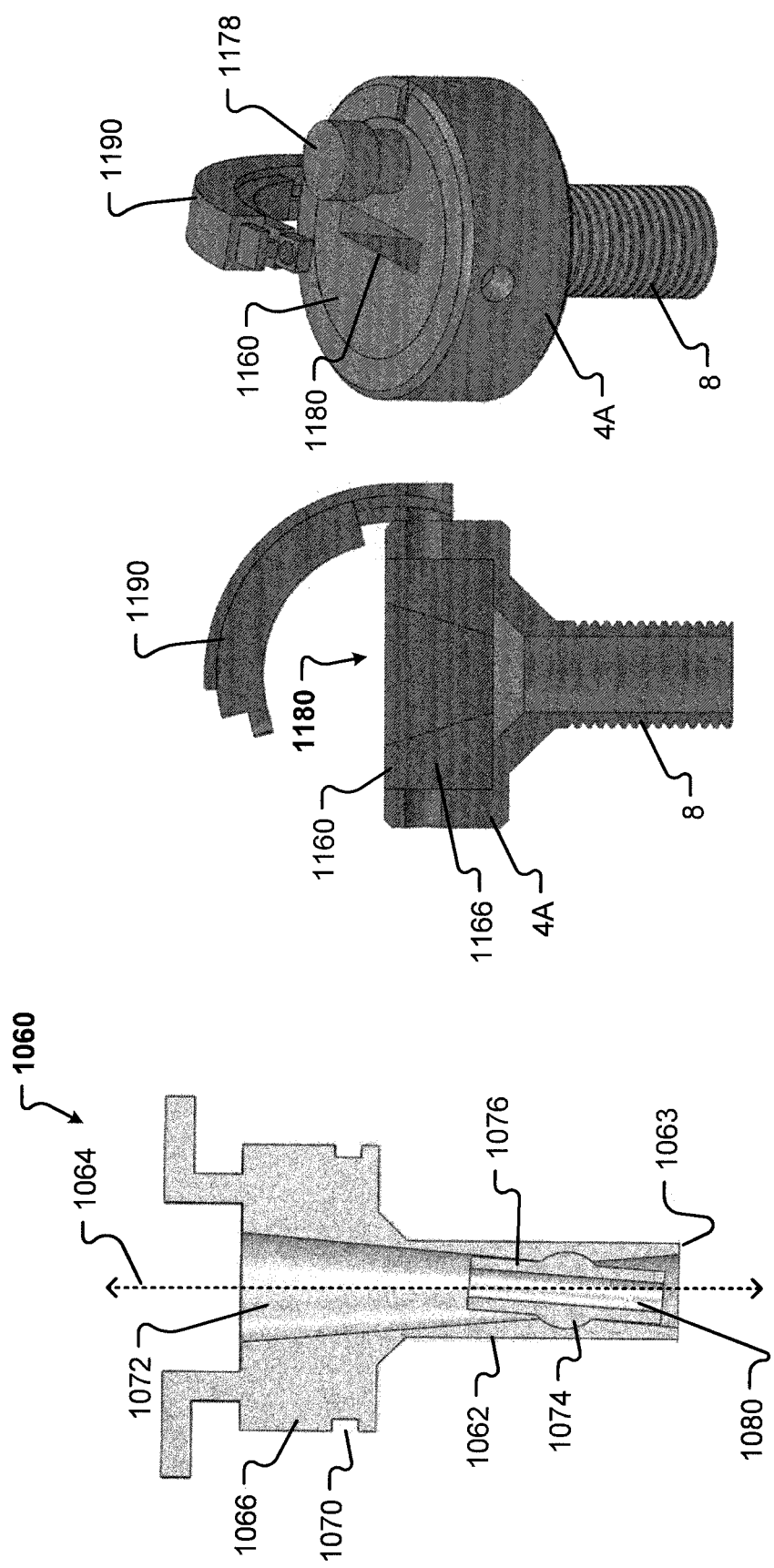

CRANIAL GUIDE FOR AN INTRACRANIAL MEDICAL PROCEDURE

CROSS REFERENCE TO RELATED APPLICATIONS

This application is a U.S. national stage entry under 35 U.S.C. § 371 of International Application No. PCT/US2018/036850 filed Jun. 11, 2018 entitled "CRANIAL GUIDE FOR AN INTRACRANIAL MEDICAL PROCEDURE," which claims priority to, and the benefit of, U.S. Provisional Patent Application Ser. No. 62/518,103 filed on Jun. 12, 2017, which are incorporated herein by reference in their entirety.

FIELD

The present disclosure relates to an intracranial guide for use in a medical procedure, such as to evacuate a subdural hematoma or to relieve an intracerebral hemorrhage. The intracranial guide generally includes a guide cannula to be received within a portion of a cranial port. The cranial port is configured to be anchored in a burr hole to be formed in the patient's cranium. The guide cannula includes at least one channel that may be used to guide a catheter to a targeted portion of the patient's anatomy or to apply a suction force within the patient's cranium.

BACKGROUND

A subdural hematoma is a collection of blood in the space between the brain and its outer membrane. Also known as a subdural hemorrhage, a subdural hematoma occurs when small veins spanning the brain and the dura (the membrane covering the brain) tear, causing bleeding in the subdural space. The resulting pressure can cause brain damage and death. Subdural hematomas are most often the result of head trauma but may also occur due to blood thinning medications and blood clotting disorders.

Subacute subdural hematomas are those discovered within 3 to 7 days of the initial head trauma. Chronic subdural hematomas are slow hemorrhages that can accumulate for weeks before the victim shows any symptoms. Elderly patients are most at risk of suffering chronic subdural hematomas due to the shrinkage of the brain that accompanies aging. As the brain shrinks, the vessels spanning the brain are stretched which makes them more susceptible to tears.

Subacute and chronic subdural hematomas can be treated with a minimally invasive bedside procedure. Bedside procedures are particularly beneficial to older patients since standard operating room procedures such as airway intubation and general anesthesia can be especially traumatic for the elderly. The current bedside procedure is performed by drilling a burr hole and threading a port into the skull. A tube and sealed suction bulb are then attached to the port and an extradural uniform negative pressure is applied to evacuate the hematoma. Alternatively, a catheter with perforations can be inserted through a small hole in the skull into the subdural space to evacuate the fluid collection.

This current procedure is limited due to deficiencies of known devices used during the procedure. For example, known ports used in procedures to evacuate hematomas are of limited usefulness. The port may not accurately guide a catheter to the hematoma. Some known ports do not enter the subdural space such that the procedure does not always completely evacuate the hematoma. Known ports also may not allow for irrigation of the site of the hematoma. Irrigation consists of washing out the desired area with a saline solution. Other known ports are not compatible with medical imaging devices, such as MRI or CT scanners. For example, some known ports are made of steel or other metals that interfere with medical imaging. Thus, these ports may not be used in conjunction with medical imaging devices to precisely guide a catheter or other tool to a targeted portion of the patient's anatomy.

Another form of brain injury is an intracerebral hematoma (ICH) which includes bleeding in the brain itself. An ICH occurs when a blood vessel tears within the brain allowing blood to accumulate. Intracerebral hemorrhages are diagnosed through an evaluation of physical symptoms and MRI or cranial computed tomography (CT) scans.

The ICH may necessitate treatment. ICH are currently surgically evacuated by craniotomies, endoscopic evacuation, or stereotactic/image guided aspiration or pharmacologic thrombolysis. These procedures are generally invasive and cannot be performed outside of an operating room. Accordingly, treatment of ICH may be delayed due to availability of a suitable operating room. Additionally, known tools used to treat ICH include many of the deficiencies associated with known tools for treating hematomas.

Due to these and other limitations associated with known ports used to evacuate hematomas and to treat ICH, there is a need for improved intracranial guide that may be used with medical imaging devices, can guide a catheter to a targeted portion of the patient's anatomy in the subdural space, and may be used to provide irrigation and suction within the patient's cranium.

SUMMARY

One aspect of the present disclosure is a novel device for evacuation of subdural hematoma. In one embodiment, the device includes irrigation capabilities. Optionally, the device can be comprised of materials that are compatible with medical imaging devices, such as an MM and a CT scanner. In another embodiment, the device includes features that are visible by medical imaging devices. In this manner, an orientation and position of the device may be determined relative to a target of a surgical procedure. In one embodiment, the features visible by the medical imaging devices are selectively interconnectable to a portion of the device. In another embodiment, the device includes a port configured to receive a cannula with at least one channel. The cannula may be rotated axially with respect to the port to guide a catheter to a targeted portion of the patient's anatomy.

Another aspect of the present disclosure is a novel cannula. The cannula is configured to be received in a port to be anchored in a patient's cranium. The cannula includes at least one channel. The channel may be used to guide a tool, such as a catheter, to a targeted portion of the patient's anatomy. In another embodiment, tubing may be interconnected to the channel. In this manner, a suction force may be applied through the channel to aspirate the targeted portion of anatomy. In one embodiment, the cannula includes at least two channels. Optionally, the channels may exit the cannula such that an exit port of each channel defines a trajectory away from the cannula. In one embodiment, the exit ports are separated by an angle of about 0° such that trajectories defined by the exit ports are substantially parallel. In another embodiment, the exit ports are separated by an angle of about 90°. In yet another embodiment, the exit ports are separated by an angle of about 180°.

In one embodiment, the channel is at a predetermined angle with respect to a longitudinal axis of the cannula. Accordingly, the cannula may be rotated around the longitudinal axis to align the channel with the targeted portion of anatomy. In one embodiment, the channel bends at least about 90° with respect to the longitudinal axis. In this manner, an exit port of the channel may be used to guide the tool radially away from the longitudinal axis within the patient's cranium. In yet another embodiment, the cannula includes one channel that is generally aligned with the longitudinal axis of the cannula. Specifically, in one embodiment, an exit port of the channel may be oriented generally parallel to the longitudinal axis. Additionally, or alternatively, the exit port can be substantially concentric with the longitudinal axis.

One aspect of the present disclosure is cranial guide for an intracranial medical procedure to be performed on a patient. The cranial guide generally includes, but is not limited to: (1) a cranial port; (2) a guide cannula; and (3) a fixture.

The cranial port includes one or more of, but is not limited to: (A) a stem that is generally cylindrical and configured to be anchored in a burr hole to be formed in the patient's cranium; (B) a cap including a distal surface interconnected to the stem, a sidewall portion extending proximally from the distal surface, and a chamber; (C) a lumen having an interior diameter which extends through the stem to the chamber to define a passage through the cranial port; and (D) a key hole extending through the cap sidewall portion. Optionally, threads may be formed on the stem to anchor the cranial port in the burr hole. In one embodiment, the stem has a predetermined length such that when the cranial port is anchored in the burr hole in the patient's cranium, the distal surface of the cap is spaced from the patient's scalp.

In one embodiment, a depth set element is releasably interconnectable to the stem. Accordingly, when the cranial port is anchored in the burr hole in the patient's cranium, a distal end of the stem is a predetermined distance from the patient's scalp. In this manner, over insertion of the cranial port can be prevented.

The guide cannula generally comprises: (A) a head having a sidewall portion and a proximal portion, the head positionable within the chamber of the cap; (B) a plurality of apertures spaced around the sidewall portion of the head, each of the apertures alignable with the key hole; and (C) at least one channel extending through the head and alignable with the lumen of the cranial port, the channel including a distal outlet such that rotating the guide cannula with respect to the cranial port alters a trajectory of the distal outlet. In one embodiment, the plurality of apertures comprises 24 apertures spaced substantially equidistant around the sidewall portion of the head.

The fixture is configured to extend a least partially through the key hole into one of the plurality of apertures aligned with the key hole. In this manner, the fixture prevents rotation of the guide cannula with respect to the cranial port.

In one embodiment, the at least one channel is configured to guide an instrument to a target within the patient's cranium. Optionally, the at least one channel includes at least one of: (i) a first channel at a first angle with respect to a longitudinal axis of the guide cannula; (ii) a second channel at a second angle with respect to the longitudinal axis; (iii) a third channel at a third angle with respect to the longitudinal axis; (iv) a fourth channel at a fourth angle with respect to the longitudinal axis; and (v) a fifth channel substantially parallel to the longitudinal axis. In one embodiment, the fifth channel is substantially concentrically aligned with the longitudinal axis.

Optionally, the guide cannula further comprises a shaft interconnected to a distal portion of the head, the shaft including an exterior diameter which is not greater than the lumen interior diameter, and wherein the channel extends through at least a portion of the shaft. In one embodiment, the shaft has a predetermined length such that when the head is received within the chamber, a distal end of the shaft extends a predetermined distance beyond a distal end of the stem. In another embodiment, the distal outlet of the channel extends through a sidewall of the shaft. Additionally, the guide cannula may optionally include indicia on the proximal portion of the head to indicate the trajectory of the distal outlet of the channel.

The guide cannula may further comprise a connector extending from the proximal portion of the head, the connector to interconnect a tube to the at least one channel of the guide cannula. In one embodiment, the guide cannula further comprises a boss extending from the proximal portion for manipulating the guide cannula.

In one embodiment, the cranial port further comprises at least one tap extending at least partially into the cap sidewall portion. The tap is configured to receive a marker. In one embodiment, the at least one tap comprises three taps having a predetermined spacing in the cap sidewall portion. Optionally, a first one of the three taps is configured to receive a first marker, a second one of the three taps configured to receive a second marker, and a third one of the three taps configured to receive a third marker.

Another aspect of the present disclosure is a cranial port configured to be anchored in a burr hole formed in a patient's cranium. The cranial port comprises: (1) a stem that is generally cylindrical; (2) a helical thread formed on an exterior surface of the stem; (3) a cap including a distal end interconnected to the stem, a sidewall that is generally cylindrical extending proximally from the distal end, and a chamber; (4) three taps formed in the sidewall, each tap configured to receive a marker adapted to be visible to a medical imaging device; (5) a key hole extending through the sidewall; and (6) a lumen extending through the stem to the chamber to define a passage through the cranial port. In one embodiment, the three taps include a first tap separated from a second tap by approximately 90° and a third tap separated from the first tap by approximately 180°. Optionally, the first tap is a first distance from a distal end of the stem, the second tap is a second distance from the stem distal end, and third tap is a third distance from the stem distal end.

Yet another aspect of the present disclosure is a cranial port configured to guide a tool during an intracranial medical procedure to be performed on a patient. The cranial port includes, but is not limited to, one or more of: (1) a head that is generally cylindrical and includes a sidewall portion, a proximal surface and a distal surface, the head adapted to be received within a chamber of a cranial port; (2) a plurality of apertures spaced around the sidewall portion of the head; (3) an annular groove in the sidewall portion configured to receive a seal element; and (4) at least three channels extending through the head, each of the channels oriented at a distinct angle relative to a longitudinal axis extending substantially perpendicular to the proximal and distal surfaces. In one embodiment, a first one of the at least three channels is oriented substantially parallel to the longitudinal axis. Optionally, a second one of the at least three channels is oriented at an angle of between about 5.5° and about 7.6° or of between about 9° and about 11° to the longitudinal axis. Additionally, or alternatively, a third one of the at least three channels is oriented at an angle of between about 11° and about 13.5° or of between about 13.5° and about 15.5° to the longitudinal axis.

These and other advantages will be apparent from this disclosure. The above-described embodiments, objectives, and configurations are neither complete nor exhaustive. As will be appreciated, other embodiments of the disclosure are possible using, alone or in combination, one or more of the features set forth above or described below. For example, it is contemplated that various features and devices shown and/or described with respect to one embodiment or in one figure may be combined with or substituted for features or devices of other embodiments or figures regardless of whether or not such a combination or substitution is specifically shown or described herein. Further, the Summary is neither intended nor should it be construed as representing the full extent and scope of the present disclosure. The invention is set forth in various levels of detail in the Summary, and, in the attached drawings and the Detailed Description and no limitation as to the scope of the invention is intended to either the inclusion or non-inclusion of elements, components, etc. in this Summary. Additional aspects of the disclosure will become more readily apparent from the detailed description, particularly when taken with the drawings.

The use of the term "distal" herein refers to a direction away from a user, such as a physician, and toward a target tissue area.

The term "proximal" refers to a direction approaching a user of the device (e.g., a physician). A proximal portion of a guide may remain at least partially external to the patient. A distal portion of a guide may be inserted at least partially into the body of the patient.

Unless otherwise indicated, all numbers expressing quantities, dimensions, conditions, and so forth used in the specification and claims are to be understood as being modified in all instances by the term "about." For example, all angles described herein may be increased or decreased by approximately 2% to achieve satisfactory results. In one embodiment, all dimensions may be varied by up to approximately 15%.

The term "a" or "an" entity, as used herein, refers to one or more of that entity. As such, the terms "a" (or "an"), "one or more," and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

BRIEF DESCRIPTION OF THE DRAWINGS

The accompanying drawings, which are incorporated in and constitute a part of the disclosure, illustrate embodiments of the disclosure and together with the Summary given above and the Detailed Description of the drawings given below, serve to explain the principles of these embodiments. In certain instances, details that are not necessary for an understanding of the disclosure may have been omitted. It should be understood, of course, that the disclosure is not necessarily limited to the particular embodiments illustrated herein. Additionally, it should be understood that the drawings are not necessarily to scale.

FIG. 1 provides views of a cranial port of one embodiment of the present disclosure;

FIGS. 2-3 are views of another cranial port of the present disclosure;

FIG. 6 provides views of fiducial markers of embodiments of the present disclosure that are interconnectable to the cranial ports of FIGS. 1-3;

FIG. 8A is an exploded view of the blank cannula of FIG. 7 proximate to the cranial port of FIG. 1;

FIG. 8B is a view of the blank cannula of FIG. 7 received within the cranial port of FIG. 1;

FIG. 9A illustrates the blank cannula of FIG. 7 received within the cranial port of FIGS. 2-3 and FIG. 9B is an exploded view of the blank cannula and the cranial port;

FIGS. 14-15 are views of catheter locks of embodiments of the present disclosure for use with cannulas of all embodiments of the present disclosure;

FIGS. 18-21 are views of a 0 degree cannula of an embodiment of the present disclosure;

FIGS. 25-27 are views of a 180 degree cannula of an embodiment of the present disclosure;

FIG. 29 provides views of an extracranial evacuation cannula of one embodiment the present disclosure;

FIGS. 31-32 are views of a dual open extracranial evacuation cannula of the present disclosure;

FIG. 41 is a front elevation cross sectional view of a cannula including a channel through a swivel guide; and FIG. 42 provides views of a cannula with an arcuate guide to orient an instrument with respect to a channel of the cannula, the cannula received by a port such as illustrated in FIG. 1.

Figure 4A:
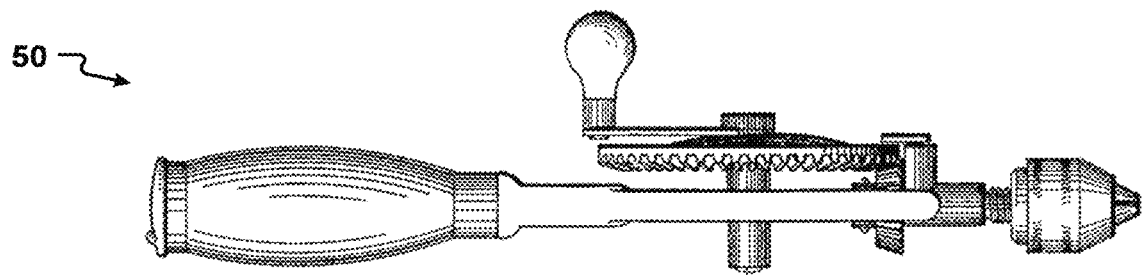
FIGS. 4A-4C illustrate tools used to prepare a burr hole in a patient's cranium.

To assist in the understanding of one embodiment of the present disclosure the following list of components and associated numbering found in the drawings is provided herein:

| Number | Component |
| --- | --- |
| 2 | Cranial guide |
| 4 | Port |
| 8 | Stem |
| 9 | Distal end of stem |
| 10 | Lumen |
| 12 | Threads |
| 16 | Cap |
| 18 | Distal surface |
| 20 | Sidewall |
| 22 | Chamber |
| 23 | Conical portion of chamber |
| 24 | Key hole |
| 26 | Wing hole |
| 28 | Tap for marker |
| 32 | Depth stop |
| 34 | Lock key |
| 36 | Column |
| 38 | Wing |
| 40 | Fiducial Marker |
| 42 | Rod |
| 44 | Head |
| 46 | Marker disc |
| 50 | Drill |
| 52 | Bit collar |
| 54 | Tap |
| 60 | Blank cannula |
| 62 | Shaft |
| 66 | Head |
| 68 | Aperture |
| 69 | Indicia aligning with aperture |
| 70 | Annular groove |
| 72 | O-ring for annular groove |
| 72A | Small O-ring |
| 74 | Wing bore |
| 76 | Wing |
| 78 | Boss |
| 80 | Burr hole |
| 160 | Single return cannula |
| 162 | Shaft |
| 163 | Distal end of shaft |
| 166 | Head |
| 168 | Aperture |
| 169 | Indicia |
| 170 | Annular groove |
| 180 | Channel through cannula |
| 182 | Exit port |
| 183 | Exit indicia |
| 184 | Connector |
| 186 | Channel plug |
| 188 | Catheter lock |
| 190 | Transverse channels |
| 191 | Prongs |
| 192 | Lock nut |
| 194 | Channel sleeve |
| 195 | Longitudinal protrusions |
| 196 | Bore |
| 260 | 0 degree cannula |
| 262 | Shaft |
| 263 | Distal end of shaft |
| 266 | Head |
| 268 | Aperture |
| 269 | Indicia |
| 270 | Annular groove |
| 280 | Channel through cannula |
| 282 | Exit port |
| 283 | Exit indicia |
| 284 | Connector |
| 288 | Catheter lock |
| 360 | 180 degree cannula |
| 362 | Shaft |
| 363 | Distal end of shaft |
| 366 | Head |
| 368 | Aperture |
| 369 | Indicia |
| 370 | Annular groove |
| 380 | Channel through cannula |
| 382 | Exit port |
| 383 | Exit indicia |
| 384 | Connector |
| 388 | Catheter lock |
| 460 | 90 degree cannula |
| 462 | Shaft |
| 463 | Distal end of shaft |
| 466 | Head |
| 468 | Aperture |
| 470 | Annular groove |
| 480 | Channel through cannula |
| 482 | Exit port |
| 484 | Connector |
| 560 | Extracranial evacuation cannula |
| 562 | Shaft |
| 563 | Distal end of shaft |
| 566 | Head |
| 568 | Aperture |
| 569 | Indicia aligning with aperture |
| 570 | Annular groove |
| 580 | Channel through cannula |
| 582 | Exit port |
| 584 | Connector |
| 586 | Catheter |
| 588 | Syringe |
| 660 | Dual open extracranial evacuation cannula |
| 662 | Shaft |
| 663 | Distal end of shaft |
| 666 | Head |
| 668 | Aperture |
| 669 | Indicia aligning with aperture |
| 670 | Annular groove |
| 680 | Channel through cannula |
| 682 | Exit port |
| 684 | Connector |
| 760 | Sieve extracranial evacuation cannula |
| 762 | Shaft |
| 763 | Shaft distal end |
| 766 | Head |
| 768 | Aperture |
| 769 | Indicia aligning with aperture |

-continued

| Number | Component |
|---|---|
| 770 | Annular groove |
| 780 | Channel through cannula |
| 782 | Exit port |
| 784 | Connector |
| 860 | Slant cannula |
| 864 | Longitudinal axis |
| 866 | Head |
| 868 | Aperture |
| 869 | Indicia aligning with aperture |
| 870 | Annular groove |
| 878 | Boss |
| 880 | Channel through cannula |
| 882 | Exit port |
| 883 | Channel indicia |
| 889 | Plug |
| 892 | Reachable areas |
| 894 | Rings |
| 960 | Single slant cannula |
| 966 | Head |
| 970 | Annular groove |
| 978 | Boss |
| 980 | Channel through cannula |
| 1060 | Swivel ball cannula |
| 1062 | Shaft |
| 1063 | Shaft distal end |
| 1066 | Head |
| 1070 | Annular groove |
| 1072 | Lumen |
| 1074 | Pivot |
| 1076 | Shaft |
| 1080 | Channel through shaft |
| 1160 | Arc guided cannula |
| 1166 | Head |
| 1178 | Boss |
| 1180 | Tapered channel |
| 1190 | Guide arm |

DETAILED DESCRIPTION

Before any embodiments of the disclosure are explained in detail, it is to be understood that this disclosure is not limited in its application to the details of construction and the arrangement of components set forth in the following description or illustrated in the accompanying drawings. The disclosure is capable of other embodiments and of being practiced or of being carried out in various ways. Also, it is to be understood that the phraseology and terminology used herein is for the purpose of description and should not be regarded as limiting.

Referring now to FIG. 1, a port 4A of an embodiment of the present disclosure is generally illustrated. The port 4A includes, but is not limited to, a stem 8 and a cap 16A. The port 4A is made of a material that is compatible with medical imaging devices, such as an MM and a CT scanner. In one embodiment, the material is selected to not interfere with, or generate artifacts in, an Mill image or a CT image. In one embodiment, the port 4A is made from plyetheretherketone (PEEK). However, the port 4A may be made of any other suitable material.

The stem 8 is generally cylindrical. In one embodiment, the stem has a diameter of between about 11 mm and about 17 mm. A lumen 10 extends through the stem 8. The lumen 10 has a predetermined interior diameter. In one embodiment, the interior diameter is substantially uniform. Optionally, the interior diameter may be between about 7 mm and about 14 mm.

Figure 24:
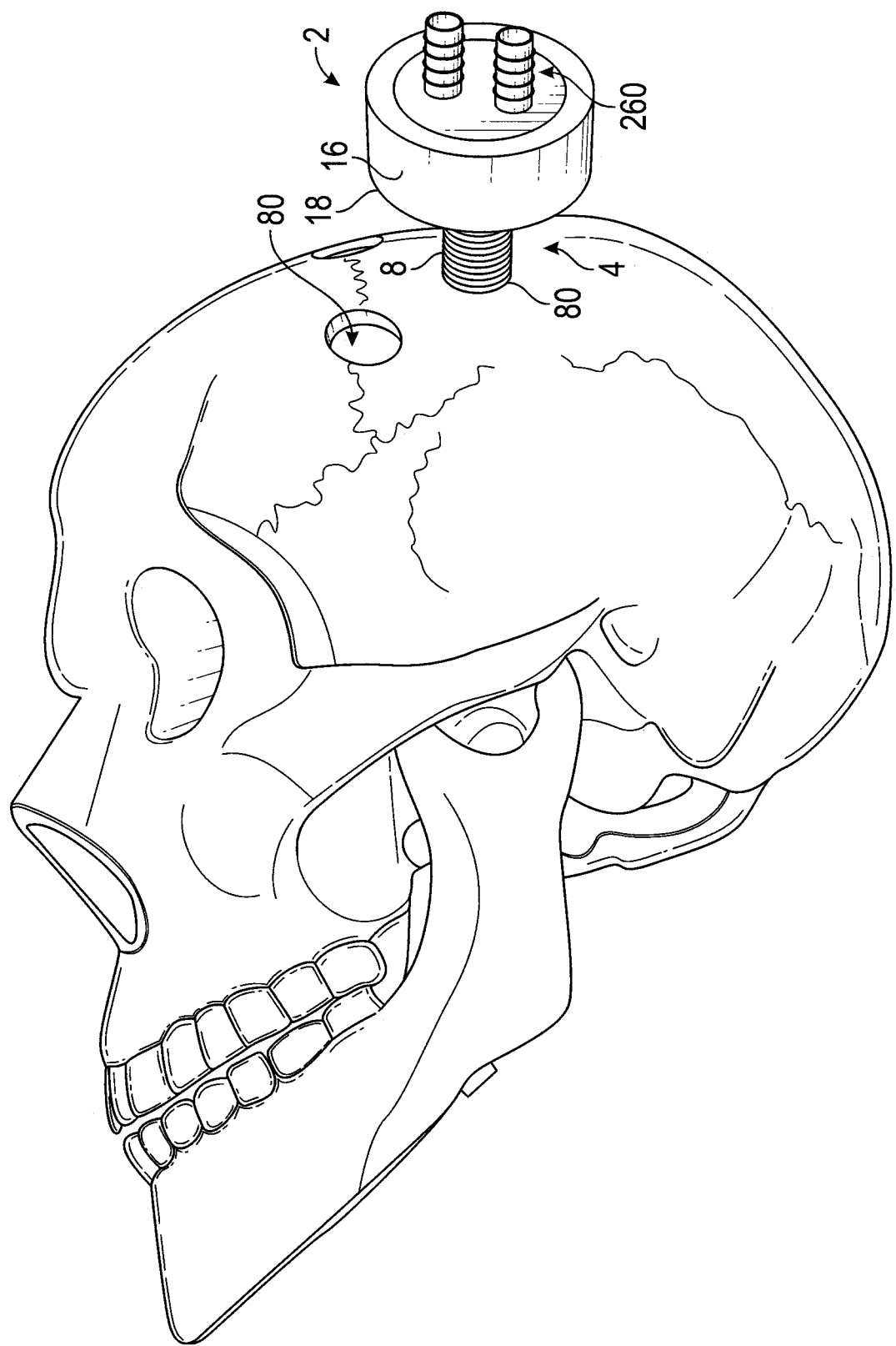
FIG. 24 illustrates a cranial port of an embodiment of the present disclosure anchored in a burr hole formed in a skull and further showing a cannula of an embodiment of the present disclosure received by the cranial port.
Figure 26E:
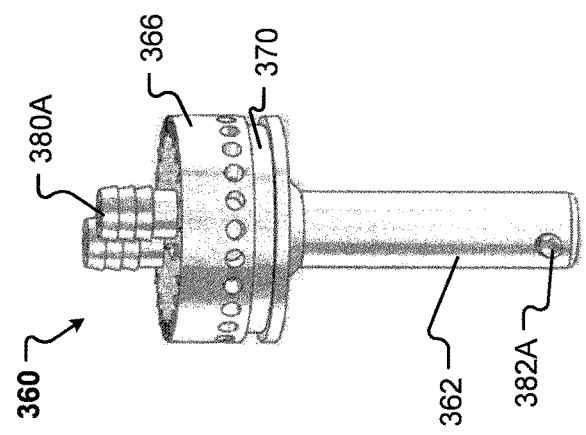
Figure 26D:
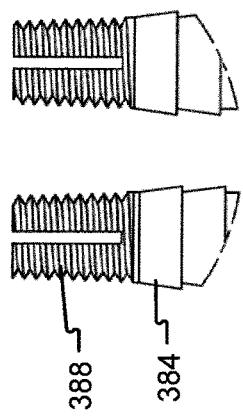
Figure 26C:
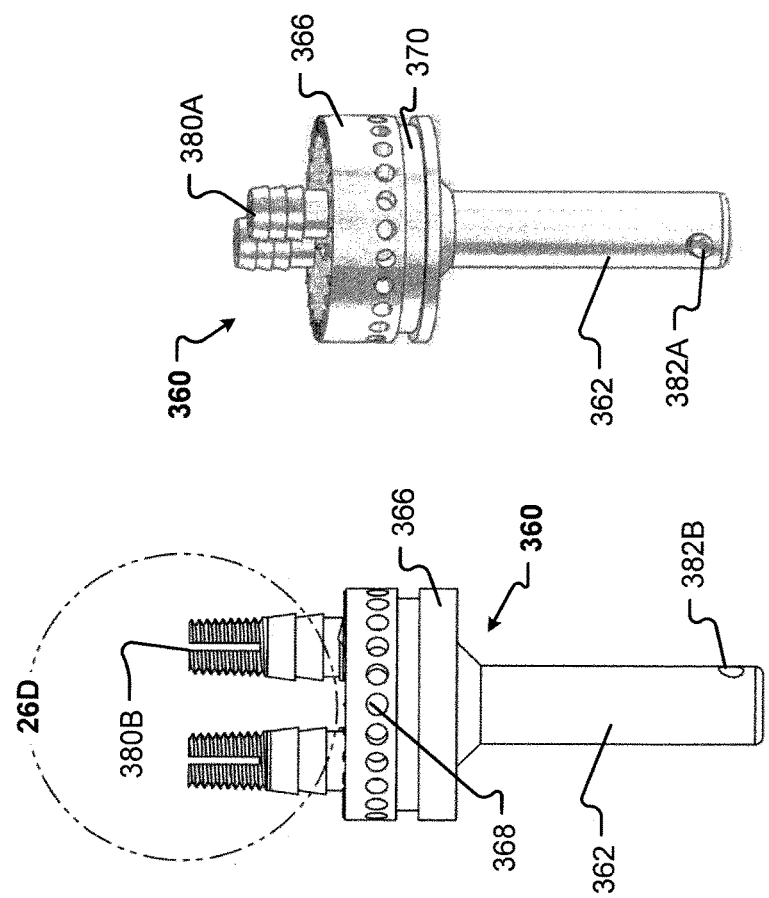
Figure 26A:
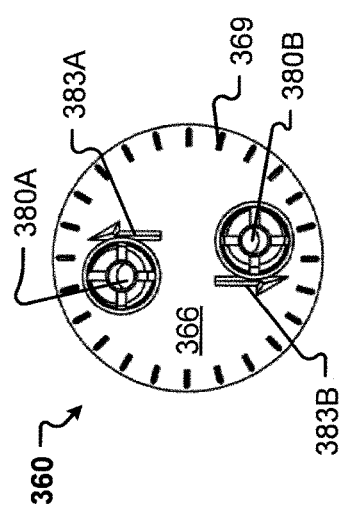
Figure 26B:
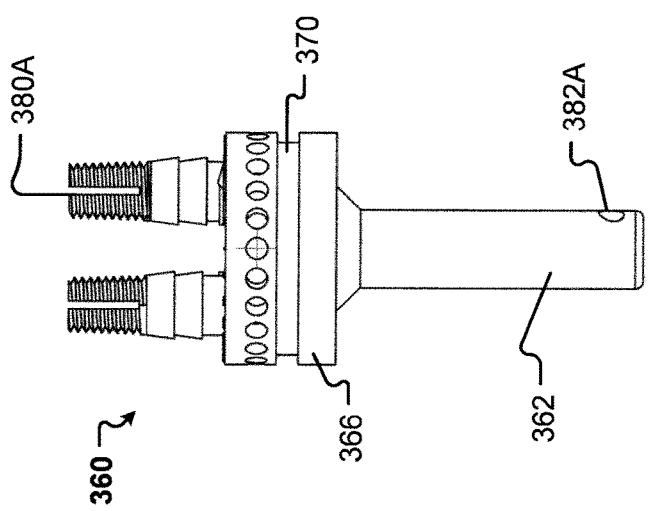

The stem 8 is configured to be anchored in a burr hole 80 formed in a patient's cranium, as generally illustrated in FIG. 24. In one embodiment, threads 12 are formed on at least a portion of the stem 8. In one embodiment, the threads 12 have a pitch of between about 1 mm and 2 mm.

The stem 8 has a predetermined length. In one embodiment, the length is selected such that when the port 4A is anchored in the burr hole 80, a distal surface 18 of the cap 16 is spaced from the patient's scalp. In another embodiment, the length of the stem 8 is between about 19 mm and about 25 mm. Optionally, a distance from a distal end 9 of the stem 8 to the distal surface 18 of the cap 16 is between about 26 mm and about 32 mm.

The cap 16A includes the distal surface 18 interconnected to the stem 8, a sidewall portion 20 extending proximally from the distal surface 18, and a chamber 22. In one embodiment, the sidewall portion 20 has an exterior height of between about 13 mm and about 19 mm. Optionally, the sidewall portion 20 has a diameter of between about 37 mm and about 44 mm. In another embodiment, the chamber 22 has a depth of between about 11 mm and about 17 mm.

Optionally, at least a portion of the distal surface 18 is angled proximally away from a proximal portion of the stem 8. In this manner, a portion of the chamber 22 proximate to the stem 8 has a shape of a frustum. More specifically, in one embodiment, a distal portion 23 of the chamber has a conical or funnel shape leading to the lumen 10 of the stem 8.

In one embodiment, a key hole 24 extends through the sidewall 20 to the chamber 22. The key hole 24 is configured to selectively interconnect a lock key 34 (illustrated in FIG. 5) to the port 4A. Optionally, the interior of the key hole 24 is threaded.

In one embodiment, at least one wing hole 26 extends at least partially into the sidewall portion 20. Optionally, the wing hole 26 may extend to the chamber 22. In another embodiment, the cap 16 includes two wing holes 26 diametrically aligned, each of the wing holes 26 extending through the sidewall portion 20 to the chamber 22. The wing hole 26 is adapted to receive a wing 38 as generally illustrated in FIG. 8.

Referring now to FIGS. 2-3, a port 4B of another embodiment of the present disclosure is illustrated. Port 4B includes many features and dimensions that are the same as, or similar to, port 4A. For example, port 4B generally comprises a stem 8 with a lumen 10 and, optionally, threads 12. A cap 16B is interconnected to a proximal portion of the stem 8. The cap 16B includes a distal surface 18, a sidewall 20, a chamber 22, and a key hole 24.

Notably, the cap 16B includes at least one tap 28 configured to receive a fiducial marker 40 such as illustrated in FIG. 9. The at least one tap 28 extends at least partially into the sidewall 20. In one embodiment, the tap 28 does not extend to the chamber 22. Accordingly, the tap 28 does not compromise an air tight seal formed when a cannula is positioned within the chamber 22. In another embodiment, an interior surface of the tap 28 is threaded.

Optionally, the at least one tap 28 comprises a first tap 28A, a second tap 28B, and a third tap 28C. In one embodiment, each tap 28A-28C has substantially the same diameter. Accordingly, a fiducial marker 40 may be positioned in any of the taps 28A-28C. Alternatively, each tap 28A-28C has a different diameter. In this manner, a first fiducial marker 40A is interconnectable to the first tap 28A, a second fiducial marker 40B is interconnectable to the second tap 28B, and a third fiducial marker 40C is interconnectable to the third tap 28C.

Optionally, unique indicia may be positioned on the port 4 to label each tap 28. Accordingly, a fiducial marker 40A-40C can be positioned in a corresponding tap 28A-28C. In one embodiment the indicia comprise at least one of letters, numbers, symbols, and colors that correspond to letters, numbers, symbols, and colors of associated fiducial markers.

In one embodiment, each tap 28A-28C is spaced from a proximal portion of the sidewall 20 by a different length. Said differently, the first tap 28A is closest to the stem 8, the third tap 28C is furthest from the stem 8, and the second tap 28B is positioned between the first and second taps 28A, 28C. In this manner, fiducial markers 40 positioned in the taps 28 are arranged in a spaced relationship along a longitudinal axis of the port 4B. Optionally, the taps 28A-28C separated by about 90° around the circumference of the sidewall 20. In one embodiment, the first tap 28A and the second tap 28C are diametrically opposed. However, in another embodiment the taps 28A-28C are separated by approximately 120°.

Figure 4B:
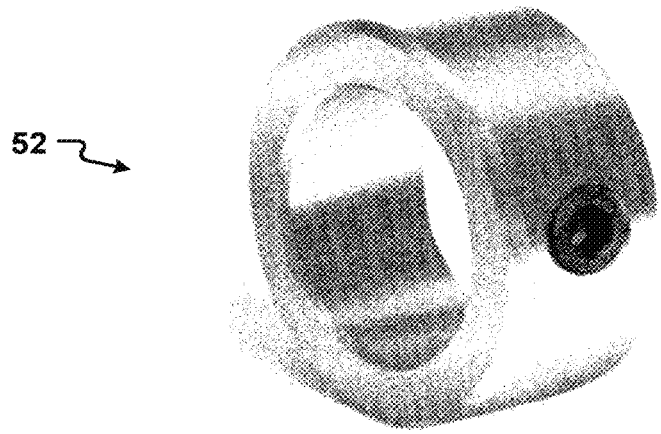

Referring now to FIG. 4A, a drill 50 used to form a burr hole 80 in a patient's cranium is shown. The drill 50 may be manually operated. In one embodiment, an electrically powered drill is used to create the burr hole. The burr hole may be of any size about equal to the exterior diameter of the stem 8. In one embodiment, a drill bit of between about 9 mm and about 16 mm is used with the drill 50 to form the burr hole 80. A bit collar 52, illustrated in FIG. 4B, may be positioned on the drill bit to limit the depth the drill bit penetrates into the patient's cranium.

Figure 4C:
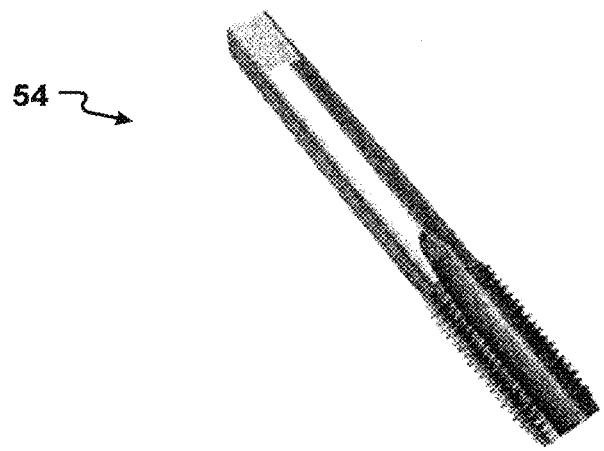

Referring now to FIG. 4C, a tap 54 may optionally be used to form threads in the burr hole 80 formed by the drill 50. The tap 54 is selected to form threads compatible with the threads 12 of the stem 8. In one embodiment, the tap 54 is sized to create threads with a pitch of about 1.5 mm with an outer diameter of about 14 mm. However, as one of skill in the art will appreciate, other diameters and thread pitches may be used with the ports 4 of the present disclosure.

Referring now to FIG. 5, a lock key 34 of one embodiment of the present disclosure is generally illustrated. The lock key 34 includes a column 36 sized to extend through the key hole 24 of ports 4 of all embodiments of the present disclosure into the chamber 22. In this manner, the column 36 can extend at least partially into an aperture 68 of a cannula 60, 160 (described hereinafter) positioned with the chamber 22 as generally illustrated in FIGS. 5C-5F. Accordingly, the cannula 60, 160 is selectively interconnected to the port 4 by the lock key. Although two embodiments of cannulas 60, 160 of the present disclosure are shown engaged by a lock key 34, cannulas of all embodiments described herein can be engaged by the lock key in a similar manner.

In one embodiment, at least a portion of the column 36 is threaded. In another embodiment, a medial portion of the column 36 is threaded. The threaded portion of the column 36 can engage threads formed in the key hole 24. In another embodiment, a distal portion of the column 36 is devoid of threads. Optionally, the column 36 is sized to extend at least about 3 mm into an aperture of the cannula. In one embodiment, the column extends between about 2.5 mm and about 4.5 mm into a cannula aperture 68 when the lock key 34 engages the cannula. In another embodiment, the column 36 has a length of between about 4 mm and 10 mm. In one embodiment, the threads extend between about 4 mm and 8 mm along the length of the column. Optionally, the lock key 34 is formed of polyphenylsulfone (PPSU). In another embodiment, the lock key 34 comprises PEEK.

Referring now to FIG. 6, embodiments of fiducial markers 40 of embodiments of the present disclosure are illustrated. The fiducial markers 40 may be interconnected to the ports 4 for computer guided tracking of the port 4 and the orientation of cannulas of all embodiments of the present disclosure positioned within the chamber 22. The fiducial markers 40 may also be used to determine the orientation and position of a catheter guided by the cannula. In one embodiment, the fiducial markers 40 are integrally formed with the port 4.

The fiducial markers 40 generally include a rod 42 extending from a head 44. Optionally, the fiducial markers 40A-40C may each have a rod 42A-42C of a different length. In this manner, the position of each fiducial marker 40A-40C may be distinguished in an image produced by a medical imaging device. When interconnected to a port 4, the fiducial markers 40 facilitate stereotactic, image guided placement of the port 4 with respect to a patient's anatomy. During stereotactic aspiration, a medical imaging device (such as a CT scanner) is used to locate hemorrhages and to guide a catheter or needle to the hemorrhages to drain the hemorrhages.

In one embodiment, each fiducial marker 40A-40C is configured to be interconnected to only one marker tap 28A-28C. For example, the rods 42 of the fiducial markers 40 may have different diameters corresponding to a diameter of one of the taps 28. Alternatively, threads formed on each of the rods 42 may be of a different size or pitch.

In one embodiment, the fiducial markers 40 are formed of a material compatible with the medical imaging device. Optionally, the rod 42 and head 44 of each fiducial marker 40 is formed of PEEK. In this embodiment, a marker disc 46 is interconnectable to the head 44. In one embodiment, an adhesive is used to interconnect the marker disc 46 to the head 44. The marker disc 46 is formed of a material that will be visible on a CT or MRI scan. In one embodiment, the marker disc 46 comprises a metal. Optionally, a unique marker disc 46 can be interconnected to each fiducial marker 40A-40C. For example, the discs 46 may have a different size, shape, or be formed of a different material such that the create a distinct image visible on the CT or MRI scan. Alternatively, in another embodiment, at least a portion of the fiducial marker 40, such as the head 44, may be formed of a material visible on a CT or MM scan. In this manner, the fiducial marker 40 may be used without the marker discs 46.

The fiducial markers 40 provide a reference point during operations where precise targeting of a portion of the patient's anatomy is necessary. For example, the marker discs 46 may be used to guide a catheter to a target within the patient's brain during a procedure such as intracerebral hematoma removal. The marker discs 46 may also be beneficial for other procedures with the port 4, such as a subdural evacuation procedure.

Referring now to FIG. 7, a blank cannula 60 of one embodiment of the present disclosure is generally illustrated. The blank cannula 60 is sized to be received within the lumen 10 and chamber 22 of all embodiments of ports 4 of the present disclosure. The blank cannula 60 is formed of a material that is at least one of chemically resistant, that can be sterilized such as in an autoclave, and is compatible with medical imaging devices, such as an MM or CT scanner. In one embodiment, the material can be used to form the blank cannula 60 by an injection molding method or by 3D printing. In another embodiment, the blank cannula 60 is formed of PPEK or polyphenylsulfone (PPSU).

The blank cannula 60 generally includes a shaft 62 interconnected to a distal portion of a head 66. Notably, the blank cannula 60 does not include a channel for a catheter. The blank cannula 60 is intended to be positioned within the port 4 during installation of the port in the patient's skull.

Accordingly, the blank cannula 60 is adapted to seal the lumen 10 of the port 4 during insertion to aid in maintaining sterility.

The shaft 62 has an exterior diameter about equal to, and no greater than, the interior diameter of the lumen 10. Optionally, the exterior diameter of the shaft 62 is between about 7 mm and about 13 mm. In one embodiment, the shaft 62 has a length that is not greater than the length of the port stem 8. Optionally, the length of the shaft 62 is between about 22 mm and about 28 mm.

The head 66 has an exterior diameter that is no greater than the interior diameter of the chamber 22. In one embodiment, the head has an exterior diameter of between about 26 mm and about 33 mm.

Figure 5A:
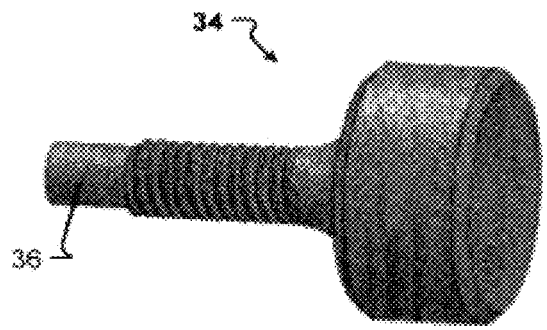
FIG. 5 illustrates an embodiment of a lock key of the present disclosure configured to be received in a key hole formed in the cranial ports of FIGS. 1-3.
Figure 5B:
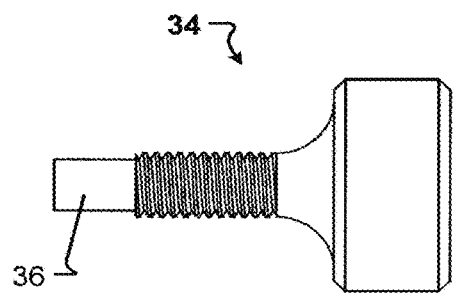
Figure 5C:
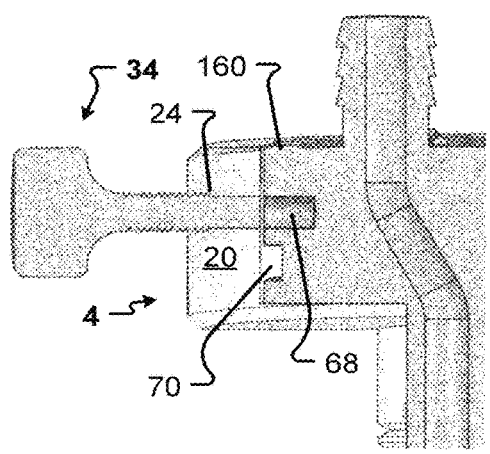
Figure 5D:
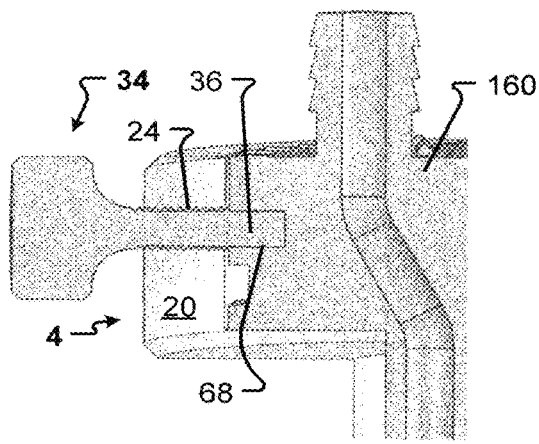
Figure 5E:
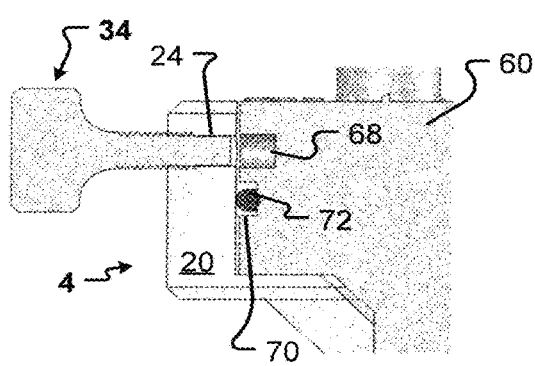
Figure 5F:
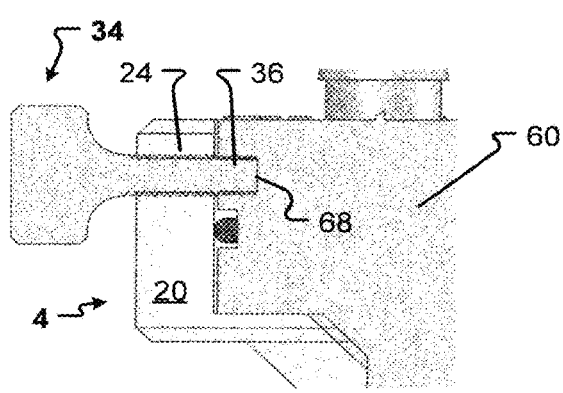
Figure 7A:
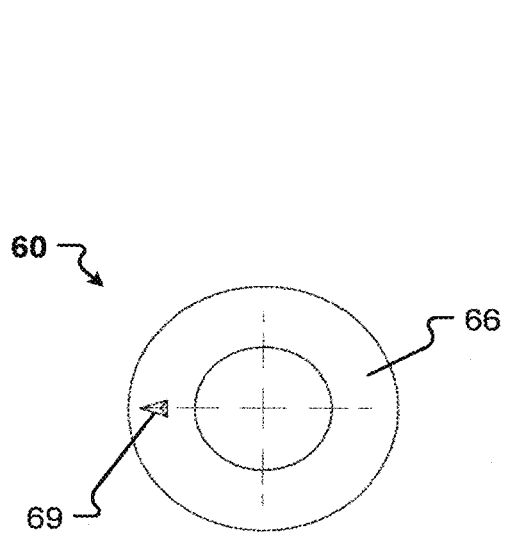
FIG. 7 illustrates a variety of views of a blank cannula of one embodiment configured to seal a lumen of each cranial port of the present disclosure.
Figure 7B:
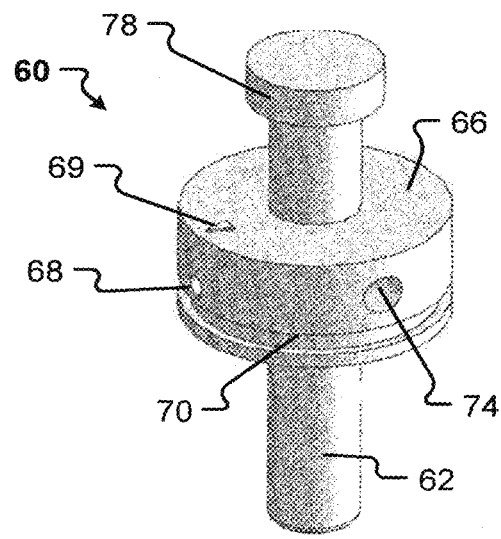
Figure 7C:
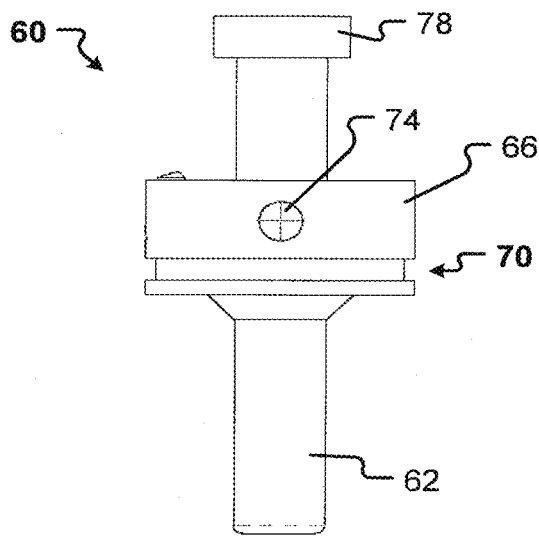
Figure 7D:
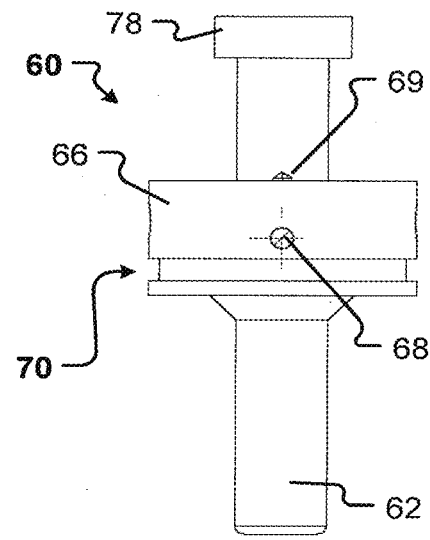
Figure 7E:
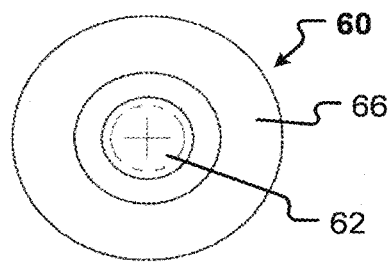

Optionally, an aperture 68 is formed in a sidewall of the head. The aperture 68 is positioned to align with the key hole 24 of the port 4. Accordingly, a lock key 34 may be positioned through the key hole 24 such that the column 36 of the lock key 34 extends at least partially into the aperture 68, such as generally illustrated in FIG. 5F.

The head 66 may also include an annular groove 70. The annular groove 70 may receive an o-ring 72 to facilitate forming an air tight seal between the blank cannula 60 and the port 4.

Optionally, a wing bore 74 may be formed through the head 66. The wing bore 74 may be substantially aligned with a diameter of the head 66. Additionally, the wing bore 74 can align with the wing hole 26 of the cap 16A. In this manner, a wing 38 may extend through the port 4A and the blank cannula 60 as illustrated in FIG. 8. The wing 38 may be used for grasping and providing leverage to the port 4A as the port 4 is rotated into a burr hole. In one embodiment, the wing bore 74 is positioned further from the shaft 62 than the annular groove 70. Accordingly, the wing bore 74 does not interfere with the air tight seal formed between the blank cannula 60 and the port 4.

Optionally, the blank cannula 60 may include a boss 78. The boss 78 may extend proximally from the head 66. The boss 78 has a shape to facilitate grasping of the blank cannula 60.

The blank cannula 60 may further comprise indicia 69 that align with the aperture 68. The indicia 69 aide in aligning the aperture 68 with the key hole 24 of the port 4.

Referring now to FIG. 8, a blank cannula 60 is illustrated in relation to a port 4A forming a cranial guide 2 according to one embodiment of the present disclosure. During a medical procedure, the blank cannula 60 will generally be inserted into port 4A to seal the lumen 10 during portions of the procedure which do not require access through the lumen. In this manner, the blank cannula 60 aides in maintaining sterility during the procedure. Thus, during installation of the port 4 into a burr hole 80, or between aspiration guided by other cannulas of the present disclosure, the blank cannula 60 can be inserted into the port 4. The blank cannula 60 may also be interconnected to a port 4 during initial imaging of the port 4 and the patient's cranium to assist determining alignment of the port 4 with respect to a target portion of the patient's anatomy.

FIG. 8 further illustrates a depth stop 32A of one embodiment. The depth stop 32A is configured to be interconnected to the stem 8 a predetermined distance from a distal end 9 of the stem 8. In this manner, when the port 4A is anchored in a burr hole 80 formed in a patient's cranium, the distal end of the stem 8 will not penetrate beyond a predetermined distance into the patient's cranium. In one embodiment, the stem 8 has a length such that the distal end will not penetrate more than about 8 mm beyond the interior surface of the cranium. The position of the depth stop 32A on the stem 8 may also be used to set a distance between the distal surface 18 of the cap 16A and the patient's scalp. In one embodiment, the stem has a length sufficient to space the distal surface 18 of the cap 16 from the patient's scalp when the stem is anchored in the bore hole. In one embodiment, the depth stop 32A is formed of PEEK.

Referring now to FIG. 9, the blank cannula 60 is illustrated in relation to a second port 4B of the present disclosure. FIG. 9A also illustrates fiducial markers 40A-40C of different lengths interconnected to the cap 16B of port 4B. Another embodiment of a depth stop 32B of the present disclosure is also illustrated. Depth stop 32B is similar to depth stop 32A. However, depth stop 32B comprises two elements that may be counter tightened together. In this manner, a first depth stop 32B applies a force to a second depth stop 32B preventing inadvertent or unintended movement of the depth stops 32B.

Figure 10B:
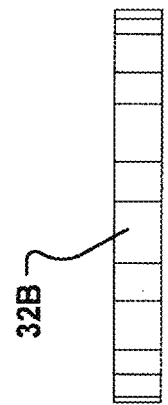
FIG. 10 shows a lock ring of one embodiment of the present disclosure which is interconnectable to the cranial ports of FIGS. 1-3.
Figure 10A:
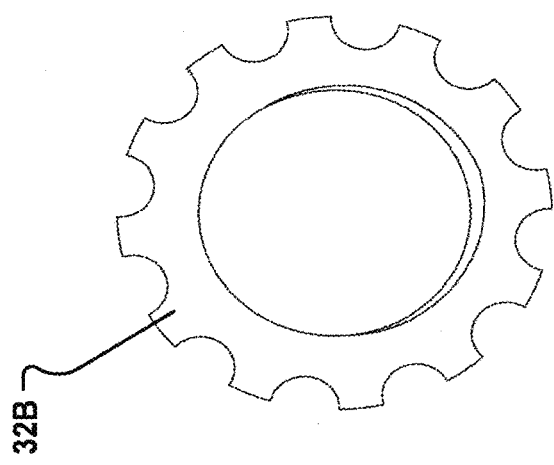
Figure 10C:
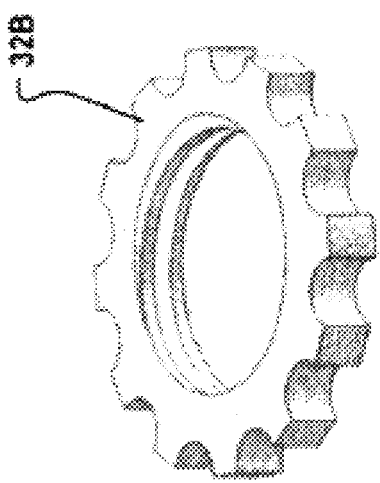
Figure 11A:
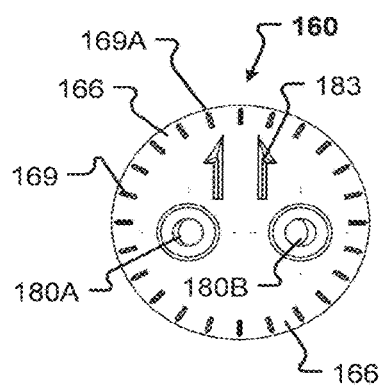
FIGS. 11-12 include views of a single return cannula of embodiments of the present disclosure for use with the cranial ports illustrated in FIGS. 1-3.
Figure 11B:
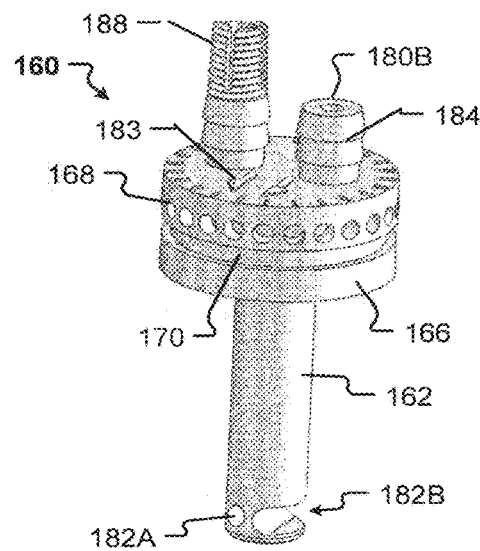
Figure 11C:
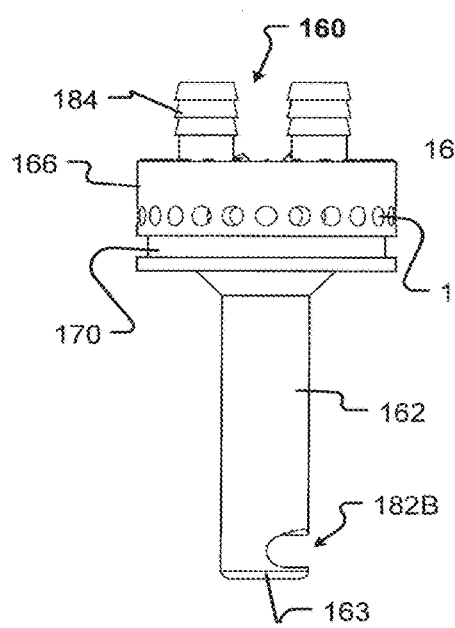
Figures 11D, 11E:
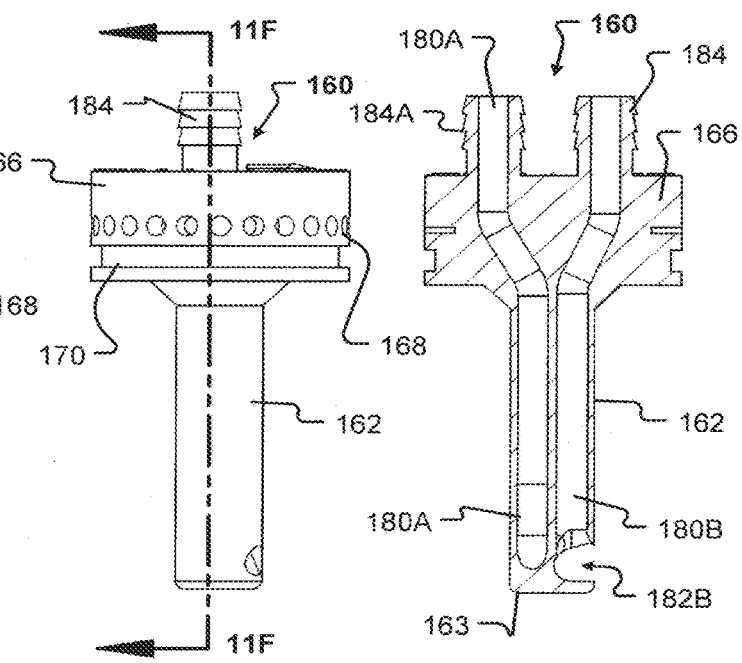
Figure 12A:
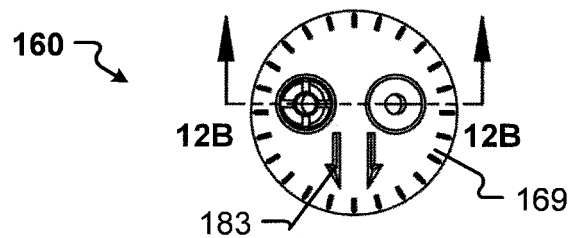
Figure 12B:
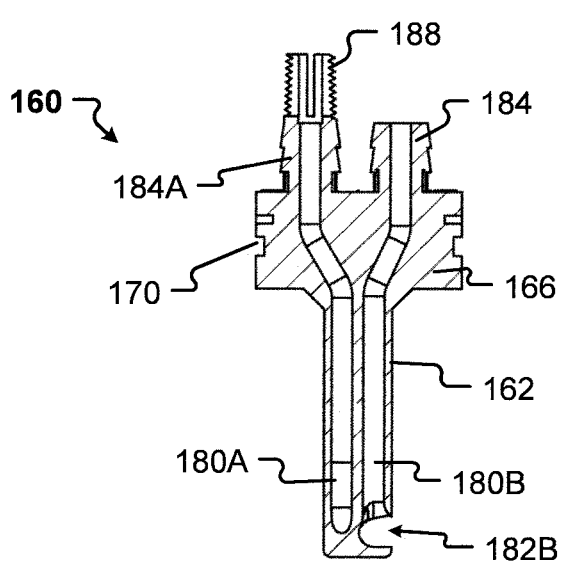
Figure 12C:
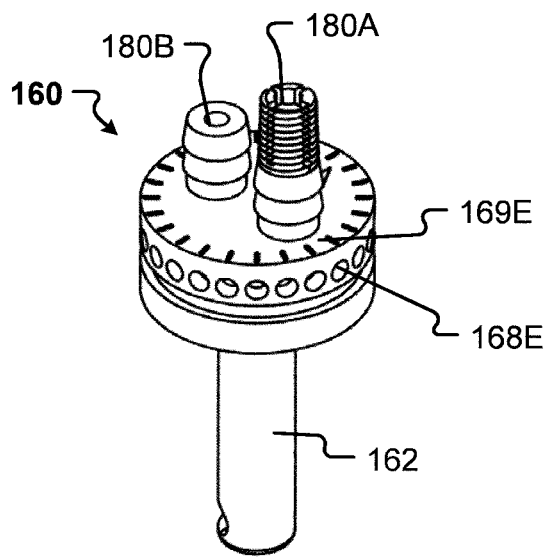
Figure 12D:
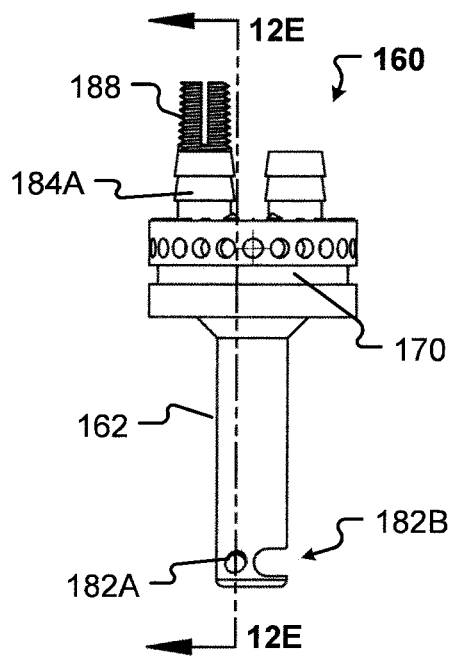
Figure 12E:
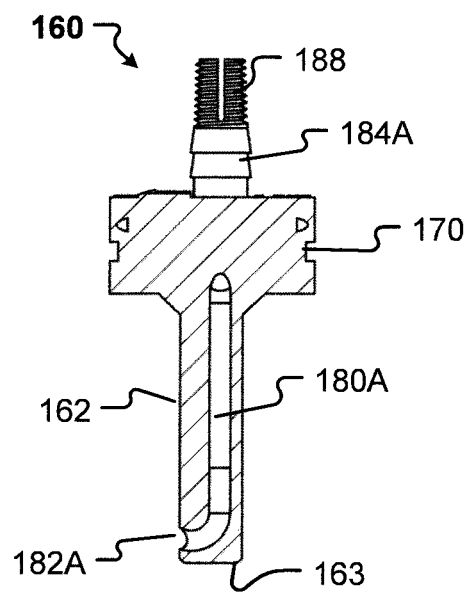

Referring now to FIG. 10, more views of depth stop 32B are provided. Depth stop 32B generally include a body with protrusions on an exterior surface. A central opening includes threads sized to engage threads of the stem 8 of all embodiments.

Referring now to FIGS. 11-12, a single return cannula 160 of an embodiment of the present disclosure is illustrated for use with all ports 4 of the present disclosure. The single return cannula 160 is generally designed for intracranial subdural evacuation procedures.

The single return cannula 160 has a shape and features similar to the blank cannula 60. Thus, the single return cannula 160 generally includes a shaft 162 interconnected to a head 166. The shaft has a length at least equal to the length of the port stem 8. In one embodiment, a distal end 163 of the cannula shaft 162 extends no more than about 8 mm past an interior wall of the patient's skull. This is for the patients' safety as a deeper penetration of the cannula shaft 162 increases the risk of injuring the patient's brain as the brain expands to refill the skull as a hemorrhage is drained by the single return cannula 160. In one embodiment, the shaft 162 has a length of between about 33 mm and about 39 mm. In another embodiment, the distal end 163 of the cannula shaft 162 is substantially flat. The flat distal end 163 will distribute pressure generated by contact between the shaft and the patient's brain evenly, reducing the risk of puncturing or laceration of the brain.

The head 166 includes a plurality of apertures 168 that are each alignable with the key holes 24 of the ports 4. In this manner, the single return cannula 160 can be rotated axially (or around a longitudinal axis) with respect to the port 4. In one embodiment, the cannula 160 may be rotated up to 360° within the chamber 22 of the port 4. When a desired orientation of the cannula 160 with respect to the port 4 is reached, a lock key 34 column may be inserted into one of the apertures 168 to fix the orientation of the cannula 160. In one embodiment, 24 apertures 168 are formed on the head 166. In another embodiment, the apertures are substantially evenly spaced around the head 166. Said differently, the 24 apertures may be formed about every 15° around the head.

Unlike the blank cannula 60, the single return cannula 160 includes at least one channel 180 that extends from the head 166 through at least a portion of the shaft 162. In one embodiment, the single return cannula includes two channels 180A, 180B. In another embodiment, the channels have an interior diameter of between about 1.5 mm and about 4.5 mm. In one embodiment, each of the two channels 180 has a diameter of between about 3 mm and 4 mm.

Channel 180A may be used to guide and direct a catheter through the single return cannula 160 to evacuate a subdural hematoma. By rotating the cannula 160 with respect to the port 4, the channel 180A may be used to guide a catheter to a targeted portion of the patient's anatomy. An exit port 182A of channel 180A guides the catheter in a trajectory away from the shaft 162. Channel 180B has an open distal end 182B (or an open return) for suction. Tubing may be attached to channel 180B to provide extracranial evacuation.

The channels exit through a sidewall of the shaft 162. In this manner, a catheter guided through channel 180A will be redirected at least 90 degrees from a longitudinal axis of the single return cannula 160 (entry angle) so as to prevent the danger of the catheters piercing the brain. More specifically, as illustrated in the cross-sectional front elevation views of FIG. 11F and FIG. 12E, channel 180A includes a turn of approximately 90° from a longitudinal axis to exit through a sidewall of the shaft 162. In one embodiment, the turn of channel 180A is slightly greater than 90° with respect to the longitudinal axis of the cannula 160.

At least one connector 184 is formed on the head 166. Optionally, a connector 184 may be formed for each of the two channels 180. The channels 180 are spaced apart at the head 166 to accommodate tubing interconnected to the connectors 184.

In one embodiment, the connectors 184 are compatible with tubing of a predetermined internal diameter. Optionally the connectors 184 have an exterior diameter sized to receive tubing with an interior diameter of between about 6 mm and about 10 mm. In another embodiment, the connectors 184 are configured to receive tubing with an interior diameter of about 5/16 inch. Optionally, the outer diameter of the tubing may be about 7/16 inch. In one embodiment, the connectors are configured to receive silastic medical grade tubing.

A catheter can be inserted into channel 180A through connector 184A when intracranial evacuation is desired. Optionally, at least one indicia 183 is formed on the head 166 indicating an orientation at which channel 180A exits from the sidewall of shaft 162 through exit port 182A. In this manner, the catheter may be guided to a targeted portion of the patient's anatomy. Tubing may be interconnected to the connector 184 to provide suction through channel 180B for extracranial evacuation. When performing an extracranial evacuation, the tubing forms an airtight seal around the connector 184.

Figure 13A:
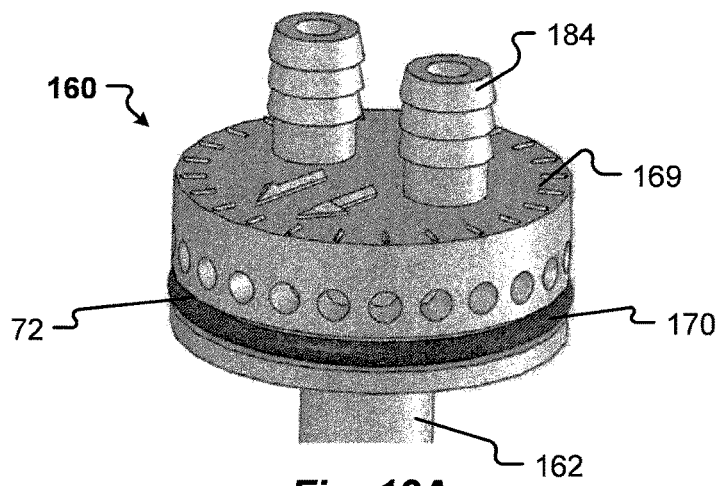
FIGS. 13A-13B illustrate embodiments of seals of the present disclosure in relation to the single return cannula of FIGS. 11-12.

FIG. 13A illustrates an O-ring 72 positioned in an annular groove 170 of the single return cannula 160. The O-ring 72 helps provide a vacuum seal with respect to a port 4 in order to aspirate a hematoma. When the cannula 160 is positioned within the port 4, the O-ring 72 contacts the interior surface of the sidewall 20 to form a seal between the cannula 160 and the port 4. In one embodiment, the seal can withstand up to about 8 psi of pressure.

Figure 13B:
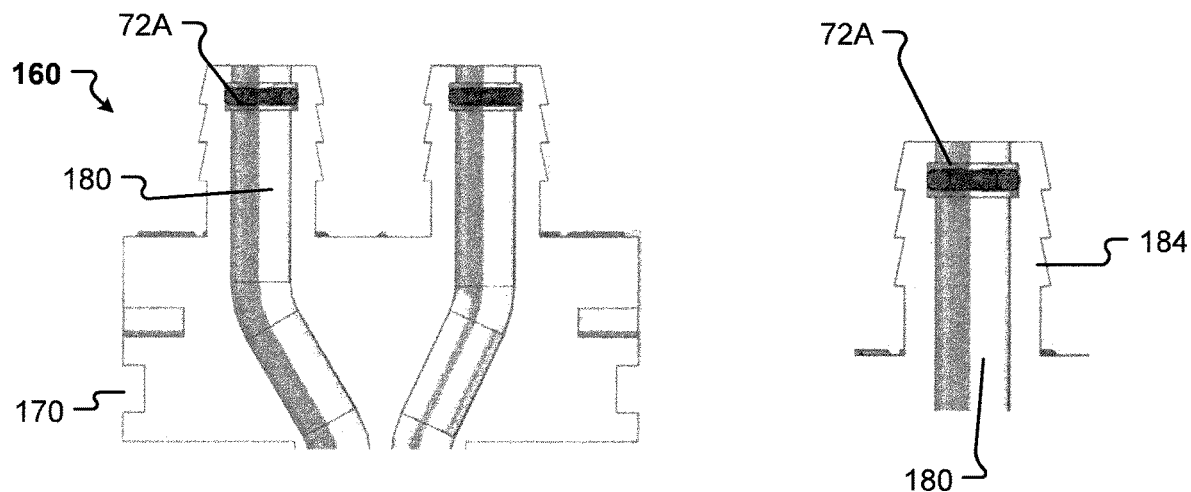

FIG. 13B illustrates smaller o-rings 72A that may be positioned within the channels 180. The small O-ring 72A forms an airtight interface or seal between an exterior of a catheter inserted through the channels 180 and an interior surface of the channel. Since the catheter must be able to slide down the channel 180, a small groove is formed for a dynamic application of the O-ring.

Figure 13C:
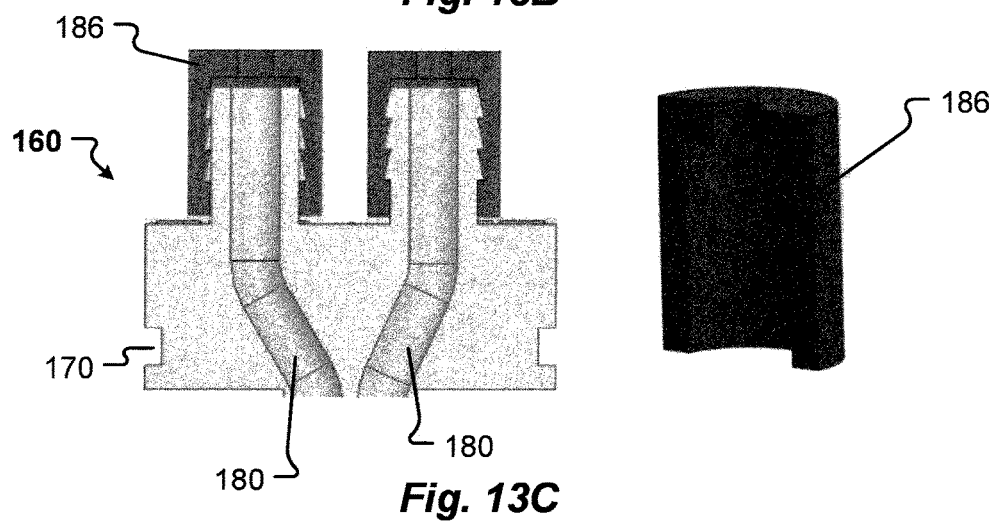
FIG. 13C show a channel plug of the present disclosure.
Figure 16A:
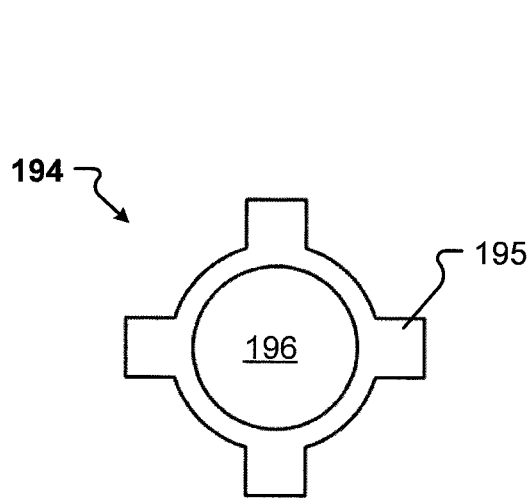
FIG. 16 provides views of a channel sleeve of one embodiment of the present disclosure.
Figure 16B:
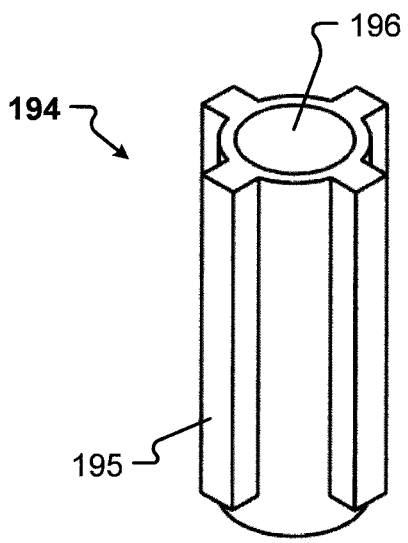
Figure 16C:
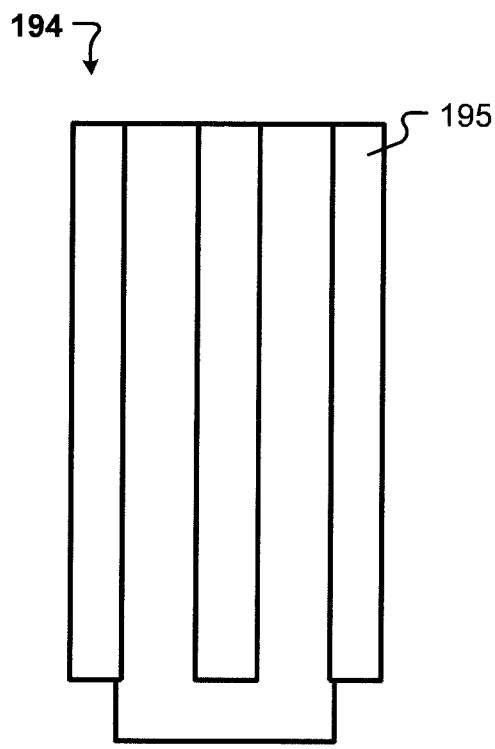
Figure 16D:
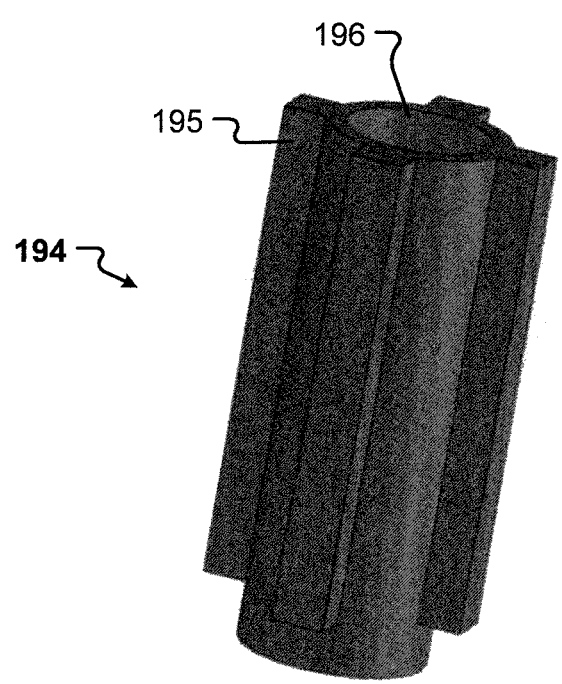
Figure 17C:
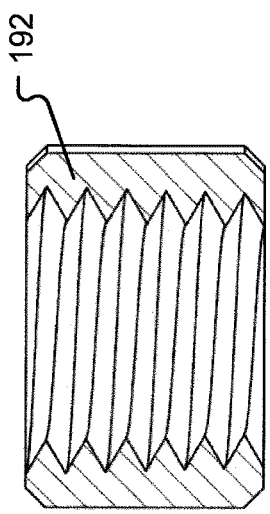
FIG. 17 provides views of a lock nut of an embodiment of the present disclosure.
Figure 17A:
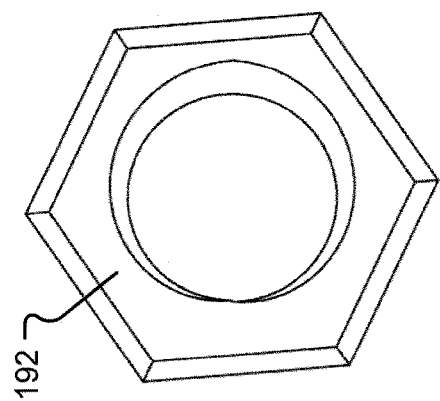
Figure 17B:
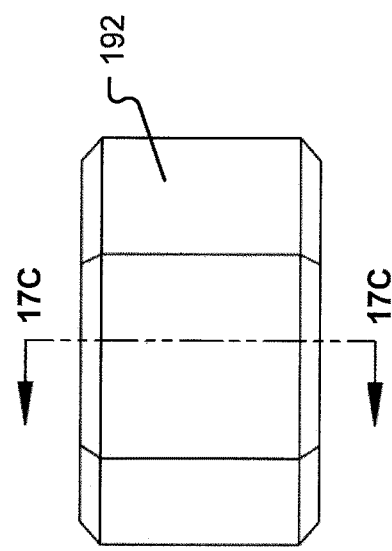
Figure 18A:
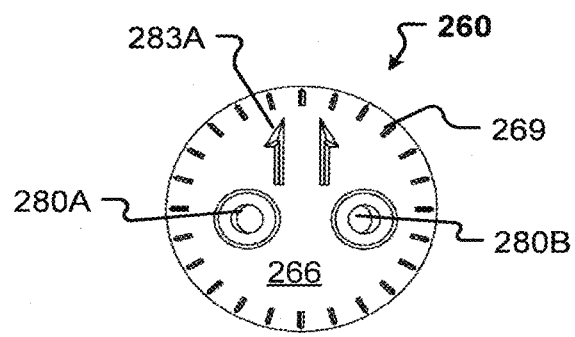
Figure 18B:
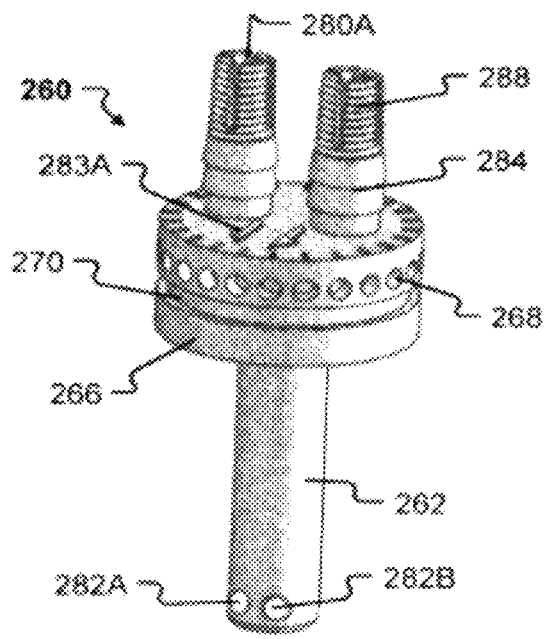
Figure 18C:
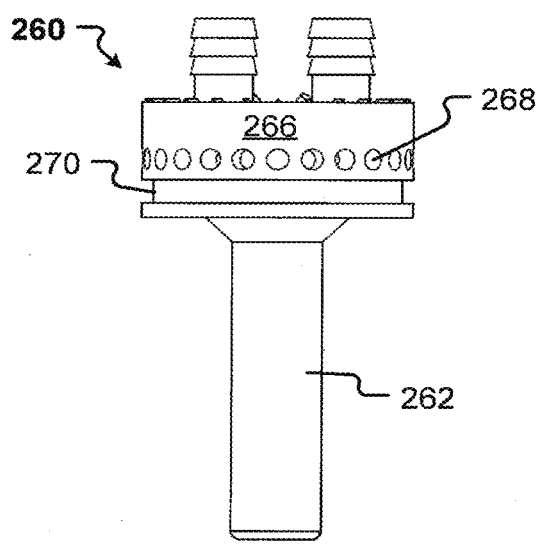
Figure 18D:
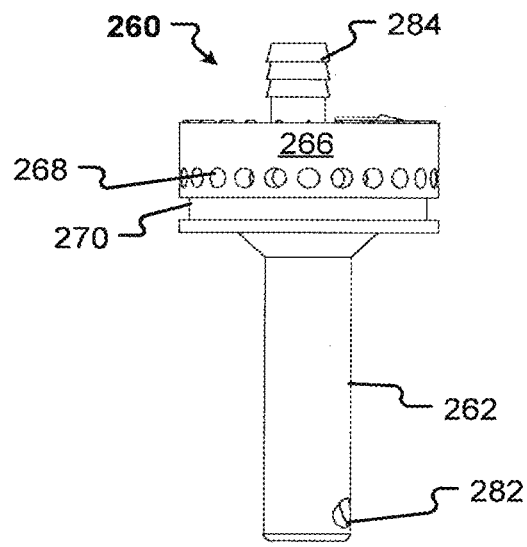
Figure 18E:
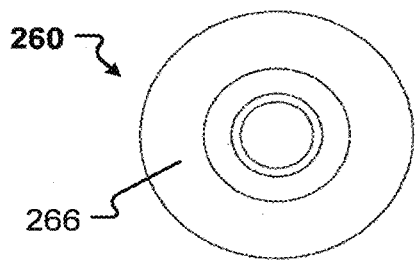
Figure 20A:
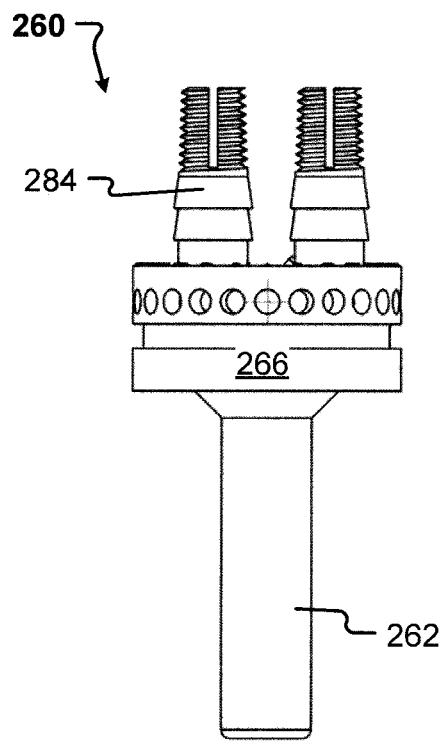
Figure 20B:
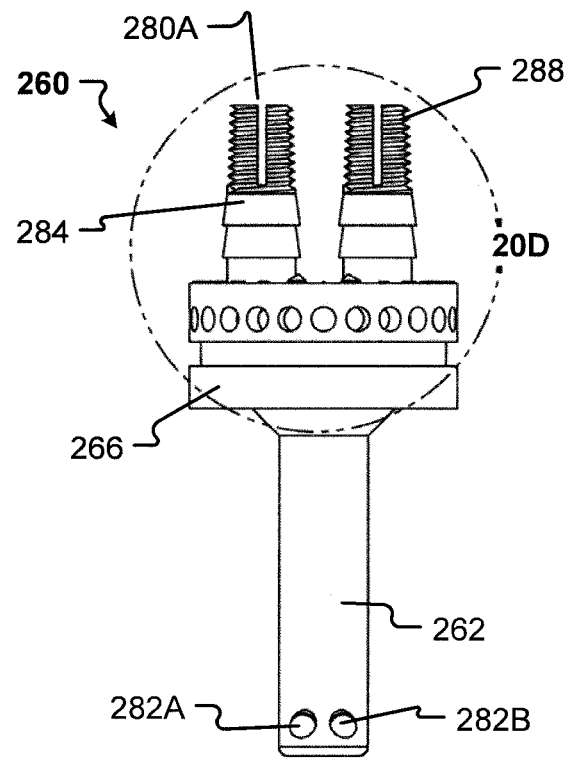
Figure 20C:
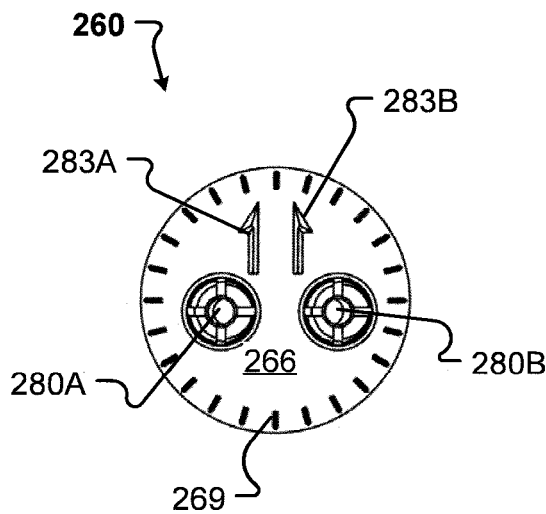
Figure 20D:
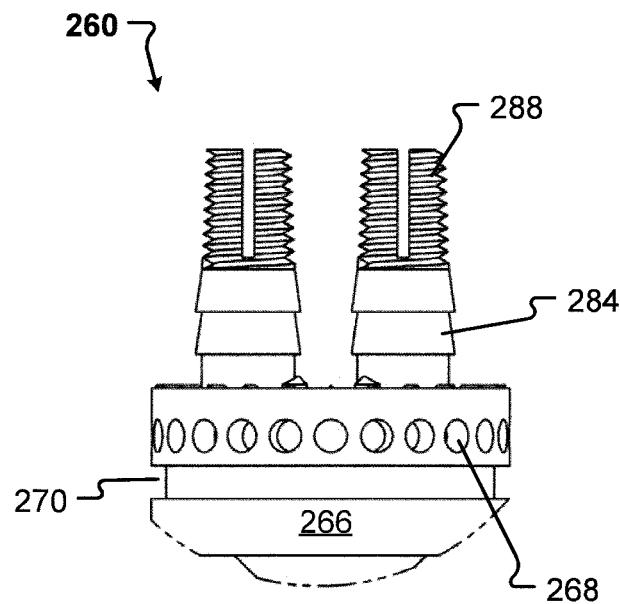

FIG. 13C illustrates a channel plug 186 of the present disclosure. The channel plug 186 may be used to provide a seal around an exterior of a catheter inserted in channel 180. Thus, channel plug 186 may be used in addition to, or instead of, a small O-ring 72A. The channel plug 186 has a cylindrical body with a small bore to receive a catheter. A large bore is sized to fit over the connector 184. In one embodiment, the channel plug 186 is formed of a polymeric material such as silicone.

Referring now to FIGS. 14-17, embodiments of catheter locks 188 of the present disclosure are generally illustrated in relation to a cannula 160. The catheter lock 188 may be used with cannulas of all embodiments of the present disclosure and is configured to prevent movement of a catheter in relation to the catheter. The catheter lock 188 includes transverse channels 190 that form prongs 191. When a catheter is in a preferred position, a fixture 192 is interconnected to the catheter lock. Because the prongs 191 are tapered, the fixture 192 forces the prongs inwardly, closing the transverse channels 190 around the catheter. Optionally, the transverse channels 190 may be filled with a compressible material, such as silicone. Thus, when fixture is interconnected to the prongs 191, the silicone material is compressed against an exterior of the catheter. In one embodiment, the fixture is a nut 192 that engages threads formed on the catheter lock 188.

Additionally, or alternatively, a channel sleeve 194 (best seen in FIG. 16) may be positioned within a channel 180. The channel sleeve 194 has a generally cylindrical body, a longitudinal bore 196 to receive a catheter or other tool, and protrusions 195 configured to fit into the transverse channels 190. In one embodiment, the protrusions 195 are generally parallel to a longitudinal axis of the channel sleeve 194. The channel sleeve 194 is formed of a compressible material. In one embodiment, the channel sleeve is formed of a Silastic liquid silicone.

Referring now to FIGS. 18-21 a 0 degree cannula 260 of an embodiment of the present disclosure is generally illustrated. The 0 degree cannula includes features the same as, or similar to, the blank cannula 60 and the single return cannula 160. Accordingly, the 0 degree cannula generally includes a shaft 262 interconnected to a head 266. A plurality apertures 268 are formed in the head. In one embodiment, the head includes 24 apertures 268. In another embodiment, the head 266 includes more, or fewer, apertures 268, such as 6, 12, 15, or 36 apertures 268 that align with the key hole 24 of a port 4.

Figure 22B:
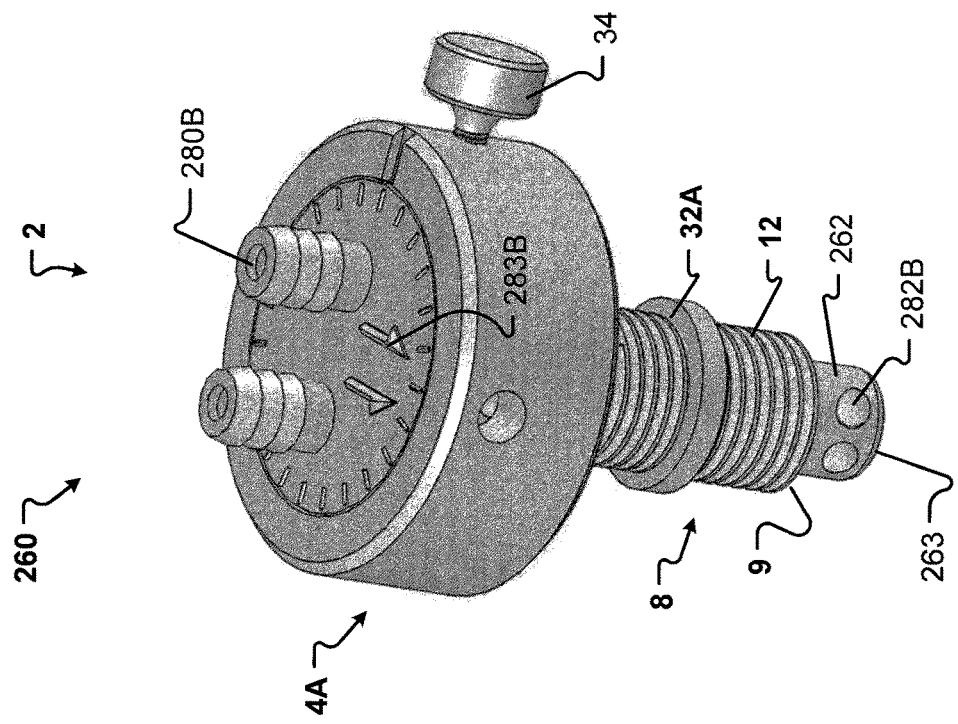
FIGS. 22A-22B illustrate a 0 degree cannula of the present disclosure aligned with and received by the cranial port of FIG. 1.
Figure 22A:
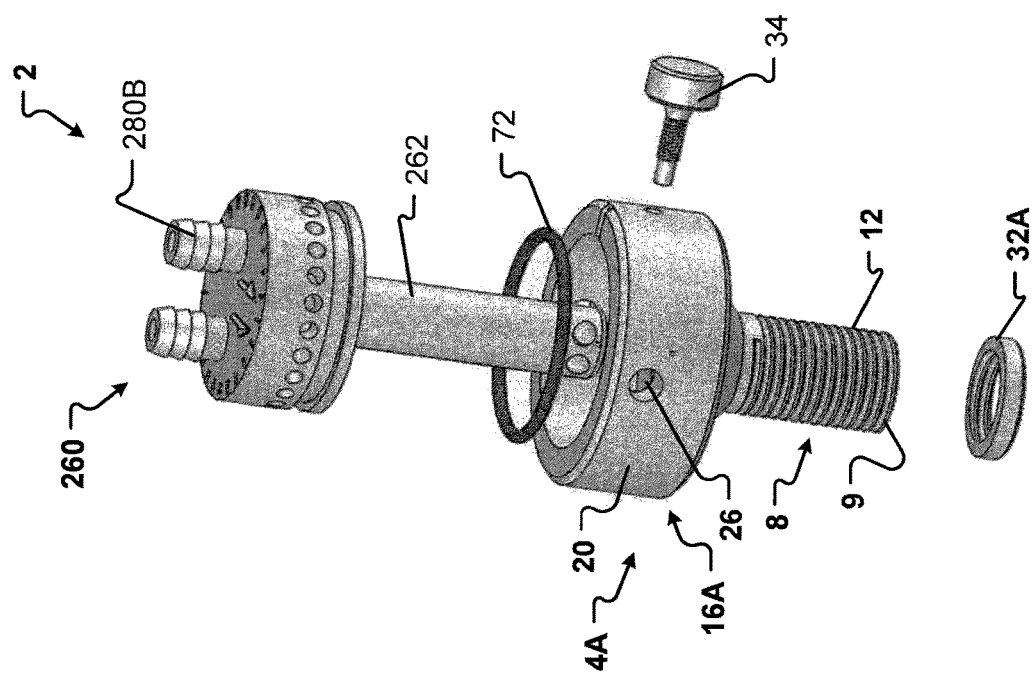
Figure 23B:
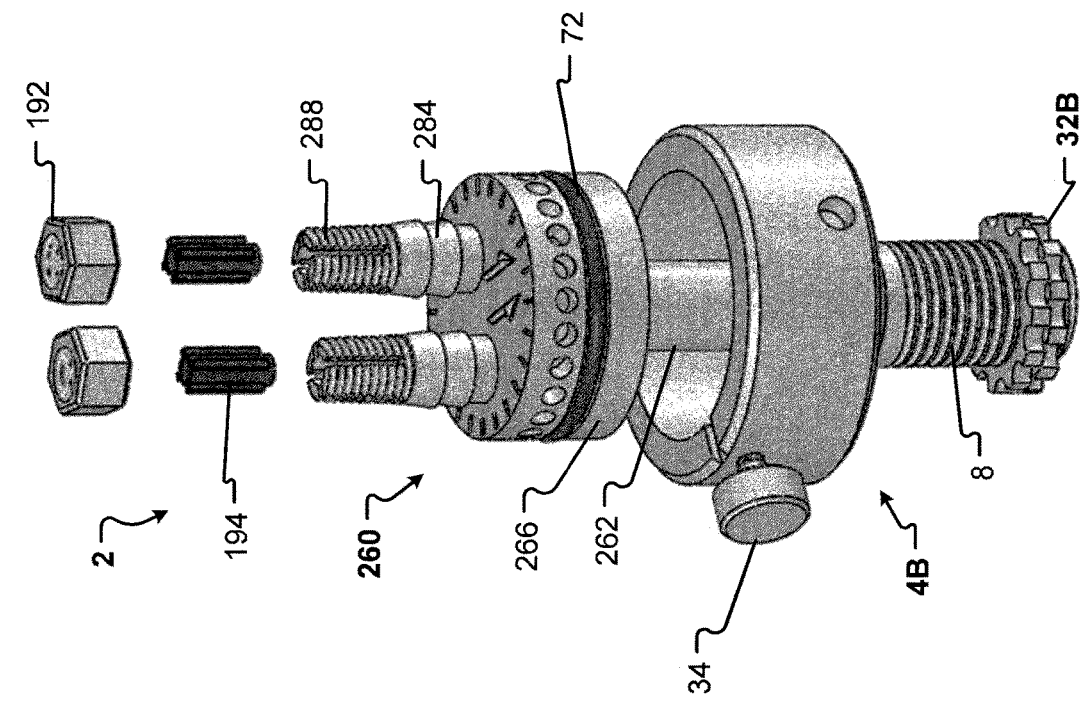
FIG. 23B is an exploded view of the cranial port and 0 degree cannula of FIG. 23A.
Figure 23A:
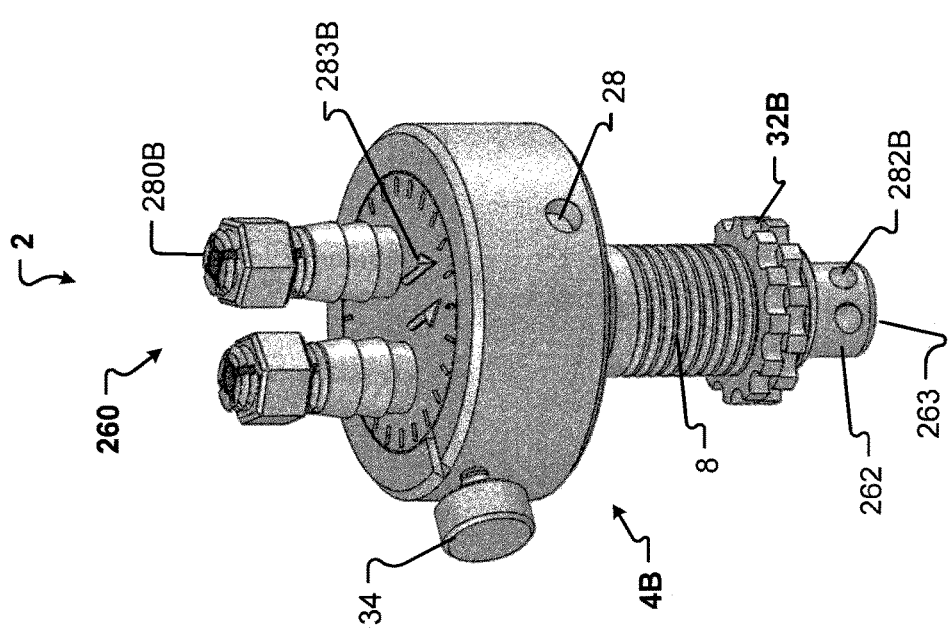
FIG. 23A illustrates another 0 degree cannula received by the cranial port of FIGS. 2-3.

Referring now to FIG. 22, a 0 degree cannula 260 is illustrated in relation to a port 4A such as illustrated in FIG. 1 to form a cranial guide 2 of one embodiment of the present disclosure. Similarly, FIG. 23 illustrates a 0 degree cannula 260 received by another port 4B of the embodiment generally described in conjunction with FIGS. 2-3 to define a Cranial guide 2 of another embodiment of the present disclosure.

Notably, compared to the single return cannula 160, the 0 degree cannula 260 includes an exit port 282 for each of two channels 280 through the cannula. In one embodiment, exit ports 282A, 282B are oriented to define trajectories that are substantially parallel. Each trajectory is substantially perpendicular to the shaft 262. The exit ports 282 do not penetrate the distal end 263 of the shaft. Further, the exit ports 4 are positioned on one side of the shaft 262. Accordingly, the channels 280 may be used to guide catheters to a targeted portion of the patient's cranium. Optionally, one channel may be used to guide a catheter to provide suction or aspiration. A second channel 280 may guide a catheter used to provide irrigation. The two catheters will exit the cannula 160 about parallel to each other.

Referring now to FIG. 24, a cranial guide 2 of an embodiment of the present disclosure is shown anchored in a burr hole 80 formed in a skull. More specifically, the stem 8 is received at least partially in the burr hole. Additionally, a distal surface 18 of the cap 16 is separated from the skull by a predetermined distance.

Referring now to FIGS. 25-27, views of a 180 degree cannula 360 of an embodiment of the present disclosure are provided. The 180 degree cannula 360 has a shape and features and dimensions which are the same as, or similar to, each of cannulas 60, 160, and 260. However, in addition to having a shaft 362, a head 366 with a plurality of apertures 368, and two channels 380, the exit ports 382 of the channels 380 are separated by about 180°. More specifically, the exit ports 382A, 382B are formed on approximately opposite sides of the shaft 362. Similar to other cannulas, the exit ports 362 are approximately perpendicular to a longitudinal axis of the shaft 362. Accordingly, the exit ports 362 do not extend through a distal end 363 of the shaft.

Figure 28B:
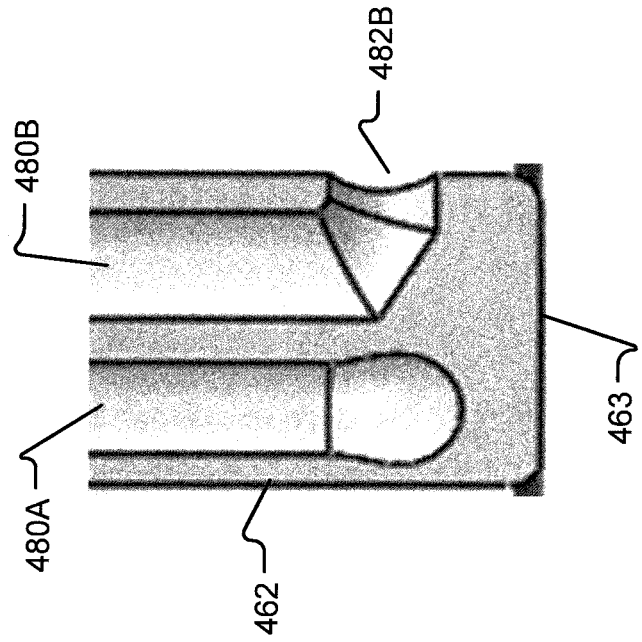
FIG. 28A illustrates a cross-sectional view of a 90 degree cannula of the present disclosure and FIG. 28B is an enlarged cross-sectional view of a distal portion of the shaft of the 90 degree cannula of FIG. 28A.
Figure 28A:
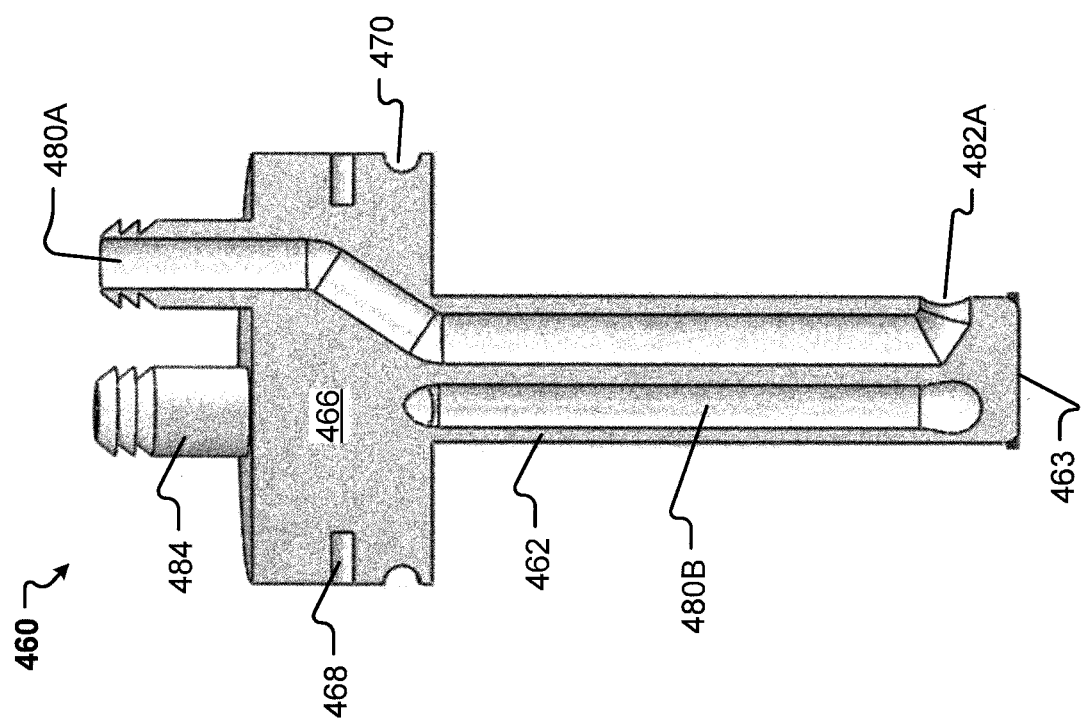

Yet another embodiment of a cannula 460 of the present disclosure is generally illustrated in FIG. 28. More specifically, a 90° cannula 460 of the present disclosure is similar to each of cannulas 260-360. However, the exit ports 482 are separated by approximately 90° around the shaft 462. The exit ports 482 extend through a cylindrical sidewall of the shaft 462. Accordingly, the distal end 463 of the shaft is closed.

Referring now to FIG. 29, an extracranial evacuation cannula 560 of an embodiment of the present disclosure is generally illustrated. The extracranial evacuation cannula 560 has a similar shape, size, and is comprised of similar materials to other cannulas 60, 160, 260, 360, 460 of the present disclosure. Accordingly, the extracranial evacuation cannula 560 interfaces with a port 4 in the same manner as the previously described cannulas. However, the extracranial evacuation cannula 560 is configured to be used for aspirating a hematoma without intracranial evacuation. To aspirate the hematoma, negative pressure is applied through a tube attached to the top of the connector 584. Optionally, the cannula 560 is made of PPSU.

The geometry and features of the extracranial evacuation cannula 560 differs in a few ways from other cannulas described herein. The head 566 has only one aperture 568 for alignment with the key hole 24 of the ports because the cannula 560 does not need to rotate with respect to the port 4.

The cannula 560 generally includes only one channel 580. In one embodiment, the channel 580 is generally aligned with a longitudinal axis of the cannula. An exit port 582 of the channel 580 is formed through a distal end 563 of the shaft 562. Accordingly, the channel 580 is substantially linear. Optionally, the channel 580 may be used to guide a catheter to a targeted portion of the patient's anatomy.

Additionally, the channel 580 has a larger interior diameter than the channels 180-480 of cannulas 160-460. In one embodiment, the channel 580 is between about 4 mm and 7 mm in diameter. In another embodiment, the channel 580 is between about 4.8 mm and 5.2 mm. The larger interior diameter of the channel 580 aides in providing uninterrupted aspiration. More specifically, the larger diameter prevents or minimizes clogging of the channel 580 and associated loss of suction to the hematoma to provide a desired flow rate from the hematoma.

Furthermore, in one embodiment, the shaft 562 has a shorter length than cannulas 160-460. More specifically, because the exit port 582 is generally aligned with the longitudinal axis, the exit port 582 does not need to extend beyond the distal end 9 of a port stem 8. In one embodiment, the cannula shaft 562 extends less than about 2 mm beyond the distal end 9 of the port stem 8 when the cannula is received in the port 4. In another embodiment, the cannula shaft 562 has a length less than the length of the port stem 8. This allows for aspiration of the entire subdural space beneath the port 4. Furthermore, since the cannula 560 does not penetrate very far (if at all) into the cranial space, the risk of hitting the brain is mitigated, maximizing patient safety.

Figure 30:
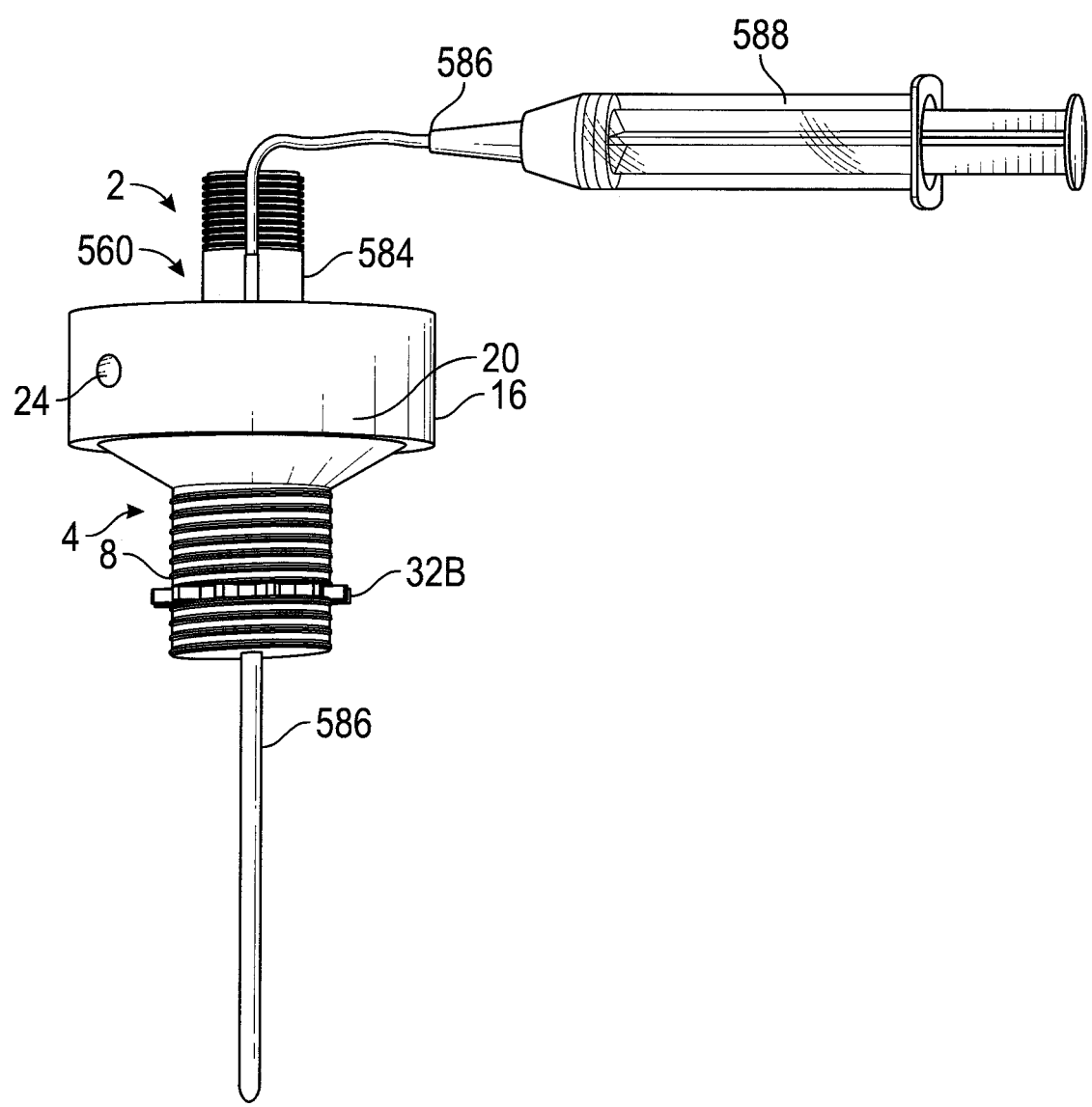
FIG. 30 is an illustration of the extracranial evacuation cannula of FIG. 29 received in a cranial port of an embodiment and further illustrating a syringe interconnected to a catheter extending through a channel of the cannula to provide suction or irrigation to a targeted portion of a patient's anatomy.
Figure 32A:
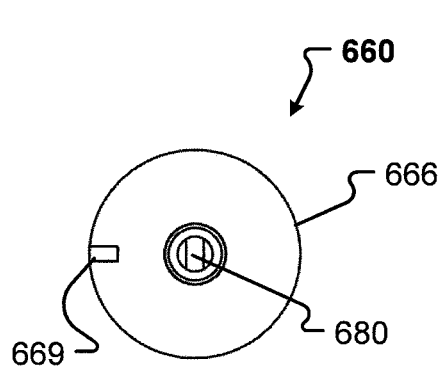
Figure 32B:
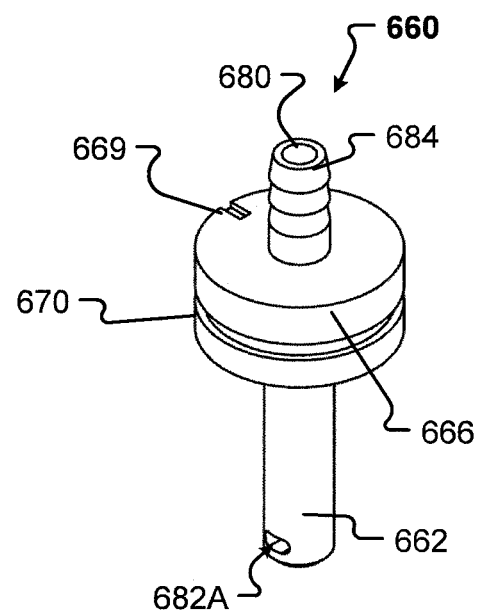
Figure 32C:
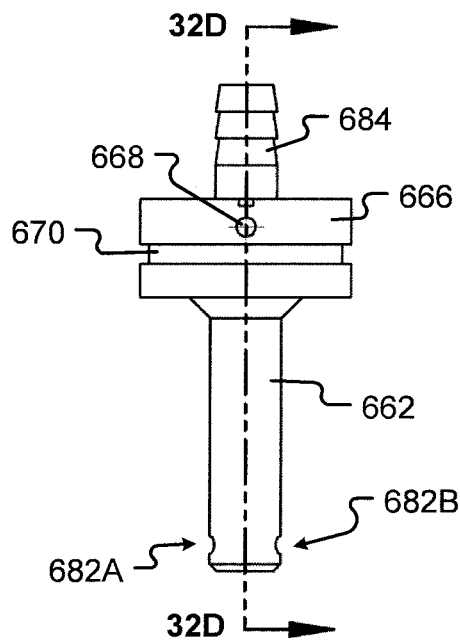
Figure 32D:
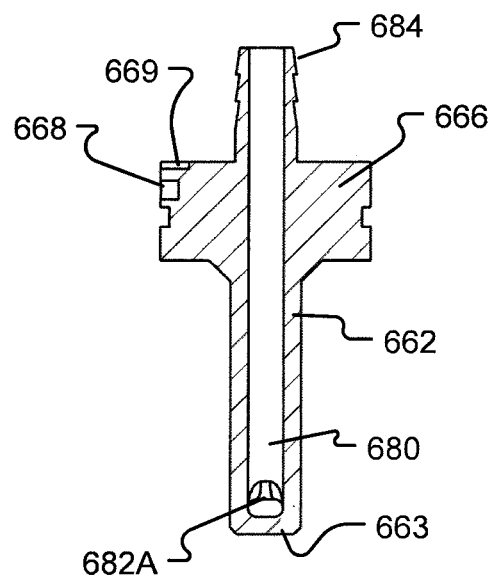
Figure 33A:
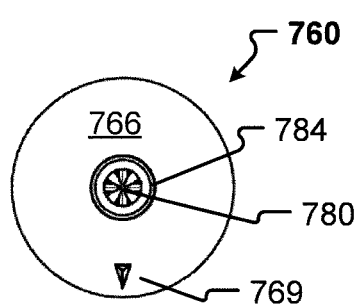
FIG. 33 shows a sieve extracranial evacuation cannula of an embodiment of the present disclosure.
Figure 33B:
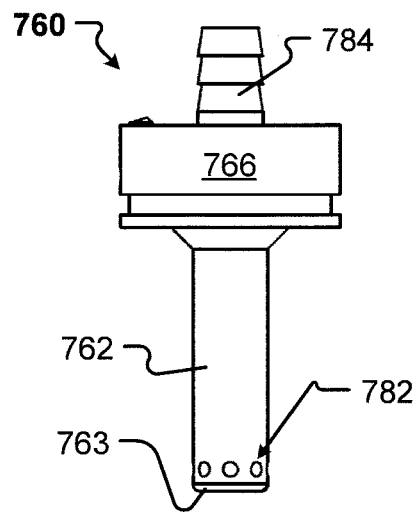
Figure 33C:
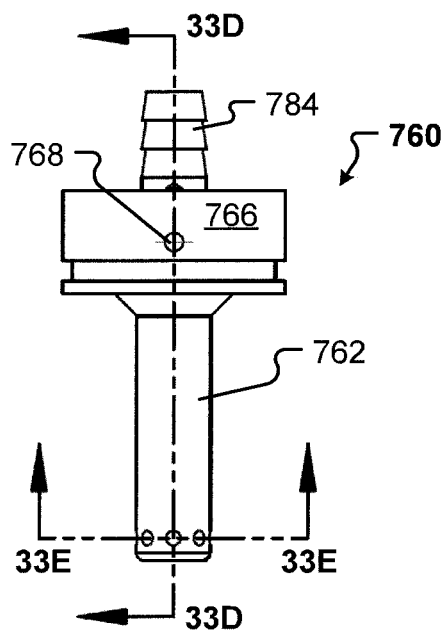
Figure 33D:
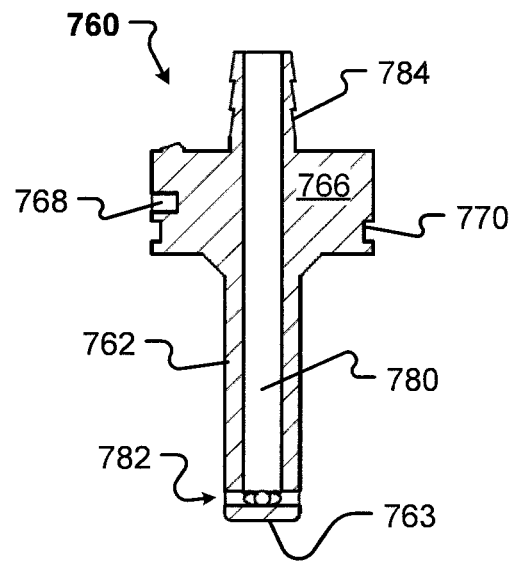
Figure 33E:
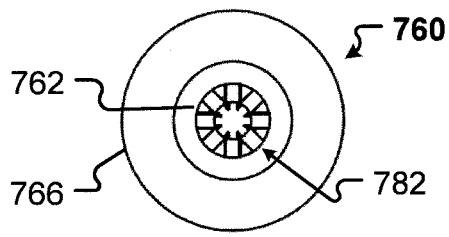

Referring now to FIG. 30, the extracranial evacuation cannula 560 of one embodiment of the present disclosure is illustrated received by a port 4 of an embodiment. FIG. 30 also illustrates a catheter 586 interconnected to a syringe 588. The catheter extends through the channel of the cannula 560. In this manner, the cannula 560 is used to provide suction or irrigation to a targeted portion of a patient's anatomy.

Catheters 586 used with all cannulas 160-1160 of the present disclosure generally have an exterior diameter about equal to the interior diameter of the channel 180-1180 through which the catheters will be guided. For channels that are curved, such as the channels 180-480 of cannulas 160-460, the catheter is flexible enough to follow curved channel portions but also sufficiently rigid to follow a desired trajectory when the catheter exits the exit port. In one embodiment, the catheter is compatible with medical imaging devices, such as a CT or MRI scanner. Optionally, the catheter may be visualized by the CT or MRI to guide the catheter during a medical procedure.

In one embodiment, the catheter 586 may be an Integra ventricular drainage catheter or an external ventricular drain (EVD) catheter. Optionally, the catheter may have an exterior diameter of between about 2.4 mm and 3 mm and an inside diameter of between about 1.1 mm and 1.7 mm. In one embodiment, the catheter is comprised of silicone and includes a stripe, such as of barium, that is visible on images generated by a CT or MRI scanner. Additionally, or alternatively, radiopaque markers may be positioned periodically along the length of the catheter for accurate depth control. In one embodiment, the catheter has a rounded distal end with holes along the sides for aspiration.

FIGS. 31-32 generally illustrate a dual open extracranial evacuation cannula 660 of the present disclosure. The cannula 660 is similar to cannula 560. However, cannula 660 notably has a longer shaft 662 than the length of shaft 562. In one embodiment, shaft 662 extends up to about 7 mm from the distal end 9 of a port stem 8. Additionally, the cannula 660 has a single channel 680. In one embodiment, the channel 680 has two exit ports 682. The exit ports 682 are about perpendicular to a longitudinal axis of the cannula 660. Optionally, the exit ports 682 are separated by about 180° such that each port 682 faces a different direction from the shaft 662. The exit ports 682 do not extend through a distal end 663 of the shaft 662.

Referring now to FIG. 33 a sieve extracranial evacuation cannula 760 of an embodiment of the present disclosure is generally illustrated. Cannula 760 is similar to cannula 660 and includes similar features and dimensions. However, cannula 760 includes a plurality of exit ports 782 formed around a longitudinal axis of the cannula 760. In one embodiment, the cannula 760 includes from four to twelve exit ports 782. In another embodiment, the cannula 760 includes eight exit ports 782 substantially evenly spaced around the shaft 762.

Figures 34A, 34B:
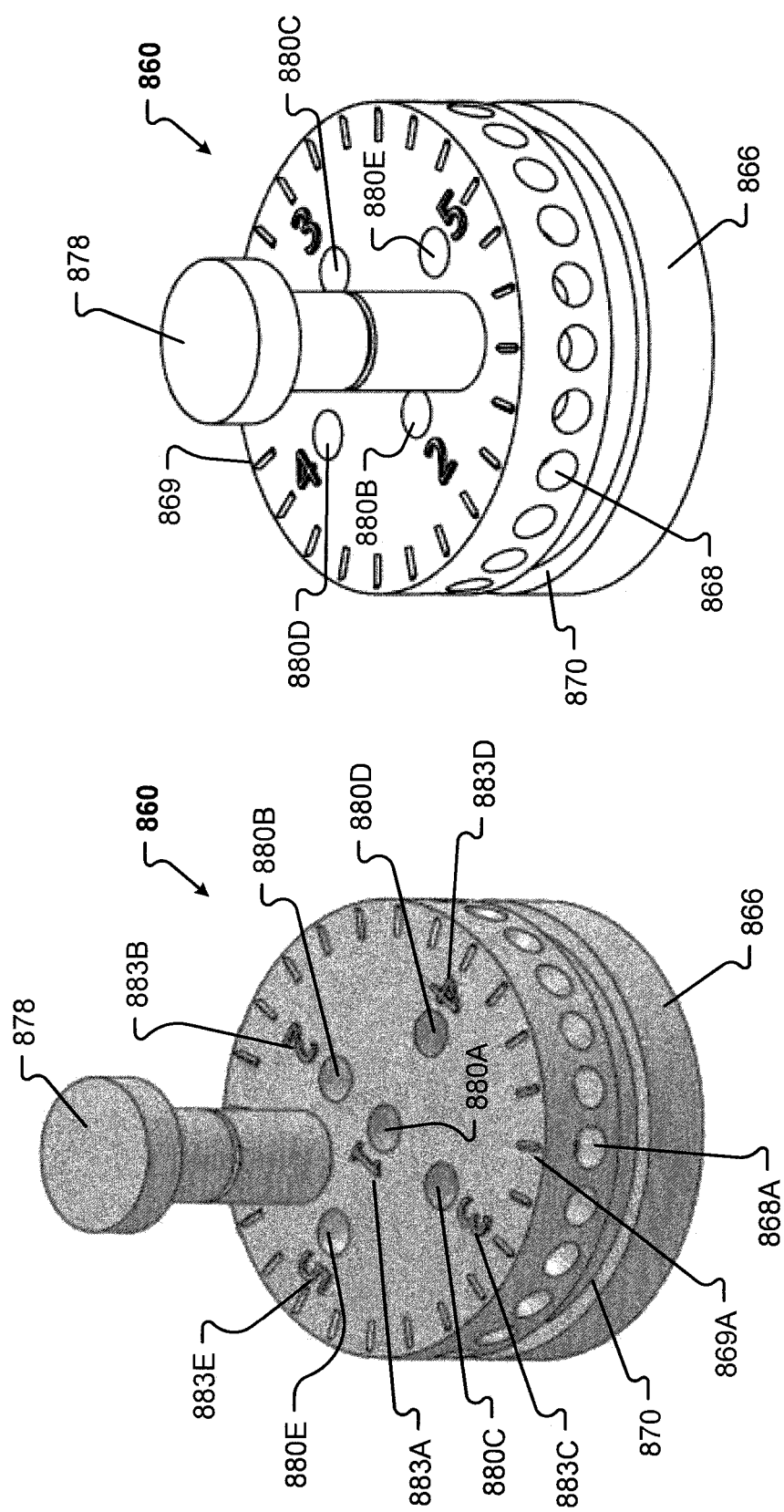
FIGS. 34-35 illustrate features of a slant cannula of an embodiment of the present disclosure, the slant cannula receivable within a chamber of the cranial ports of FIGS. 1-3.
Figure 35B:
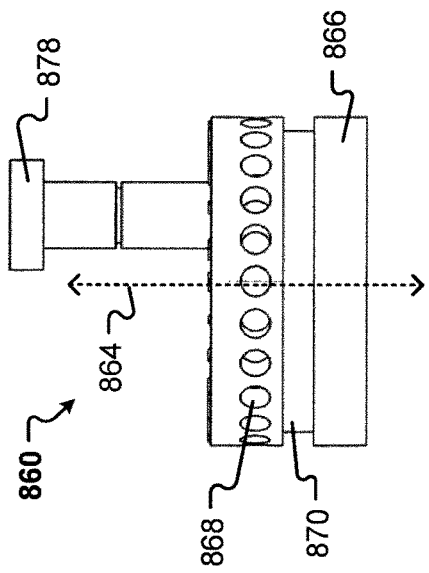
Figure 35D:
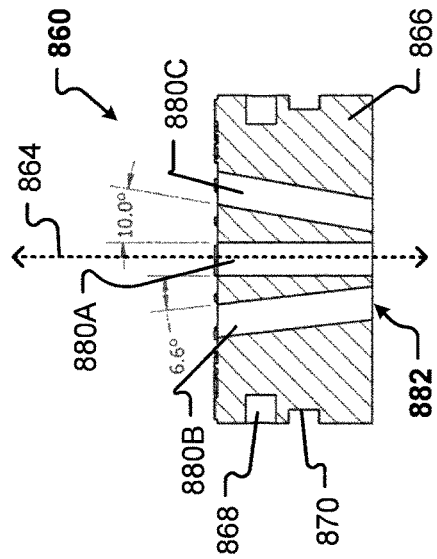
Figure 35A:
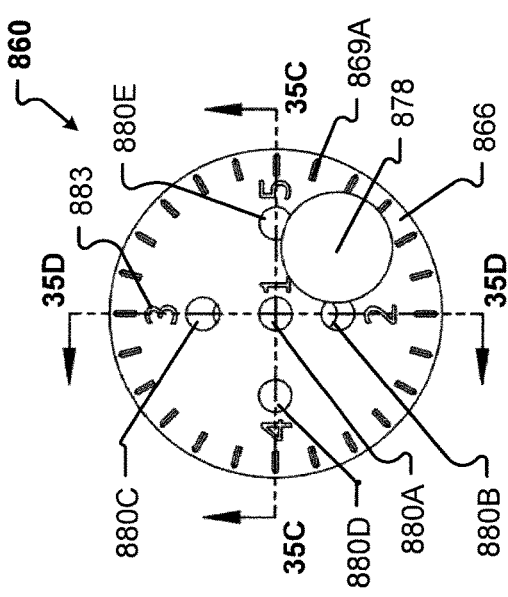
Figure 35C:
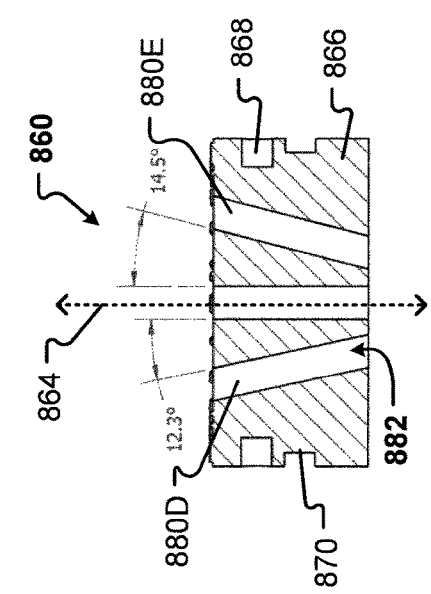

Referring now to FIGS. 34-35, a slant cannula 860 of an embodiment of the present disclosure is generally illustrated, the slant cannula 860 receivable within a chamber of a port 4. The slant cannula 860 is configured to guide a catheter into the brain of a patient along a range of angles and a various depths. A variety of medical procedures may be performed using the slant cannula 860, including without limitation procedures to drain or provide relief for intracerebral hemorrhages.

The slant cannula 860 generally comprises a head 866 that has the same, or similar, shape and size as the heads of other cannulas 60-760 of the present disclosure. However, the slant cannula 860 does not include a shaft. Optionally, a boss 878 may be interconnected to the head 866.

Additionally, the slant cannula 860 includes a plurality of channels 880. In one embodiment, from 1 to 5 channels 880 are formed through the head 866. Each channel 880 has a different orientation with respect to a longitudinal axis 864 substantially centered on the head. In one embodiment, a first channel 880A is oriented substantially parallel to the axis 864. Optionally, the first channel 880A may be concentrically aligned with the axis 864. A second channel 880B is oriented at an angle of between about 5.5° and about 7.6° to the axis 864. In one embodiment, the angle of the second channel 880B relative to the axis 864 is approximately 6.6°. A third channel 880C is oriented at an angle of between about 9° and about 11° to the axis 864. Alternatively, the third channel 880C can be formed at an angle of approximately 10° relative to the axis 864. A fourth channel 880D is oriented at an angle of between about 11° and about 13.5° to the axis 864. In one embodiment, the fourth channel 880D is oriented at approximately 12.3° to the axis. A fifth channel 880E is oriented at an angle of between about 13.5° and about 15.5° to the axis 864 or, in another embodiment, at about 14.5°. Accordingly, when the head 866 is received with a chamber 22 of a port 4, rotating the head 866 around the axis 864 facilitates guiding catheters through the channels 880 to a plurality of areas within a patient's cranium.

Optionally, indicia 883 are associated with each of the channels 880. In one embodiment, the indicia 883 are sequential and the first indicia 883A is associated with the least angled channel 880A and the final indicia 883E is associated with the most angled channel 880E.

The head 866 also includes a plurality of apertures 868. In one embodiment, the head 866 includes 24 apertures. In this manner, when a channel 880 is in a preferred orientation with respect to the port 4, a lock key 34 may be inserted into an aperture 868 aligned with the key hole 24 to fix the head 866 to the port 4. Further, because the cannula 860 includes four channels 880B-880E angled to the axis 864, one channel 880A generally aligned with the axis 864, and 24 apertures, the slant cannula 860 can be used to guide a catheter or other tool in up to 120 possible angles.

Figure 36A:
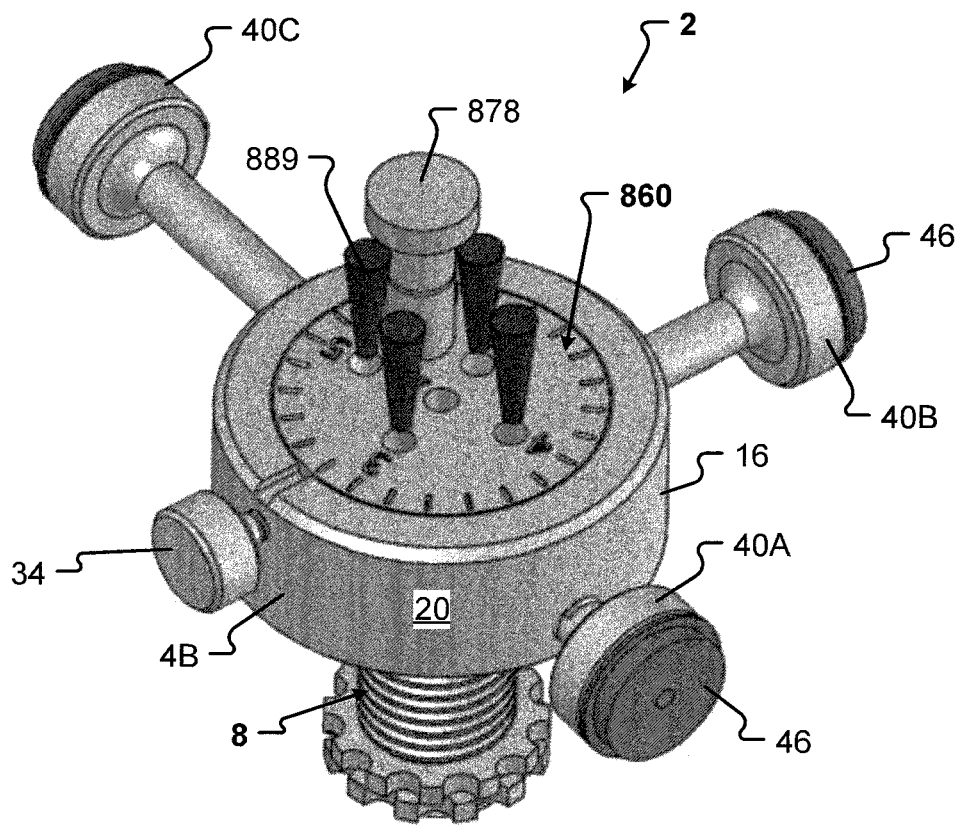
FIG. 36 provides views of the slant cannula of FIGS. 34-35 received by the cranial port of FIGS. 2-3.
Figure 36B:
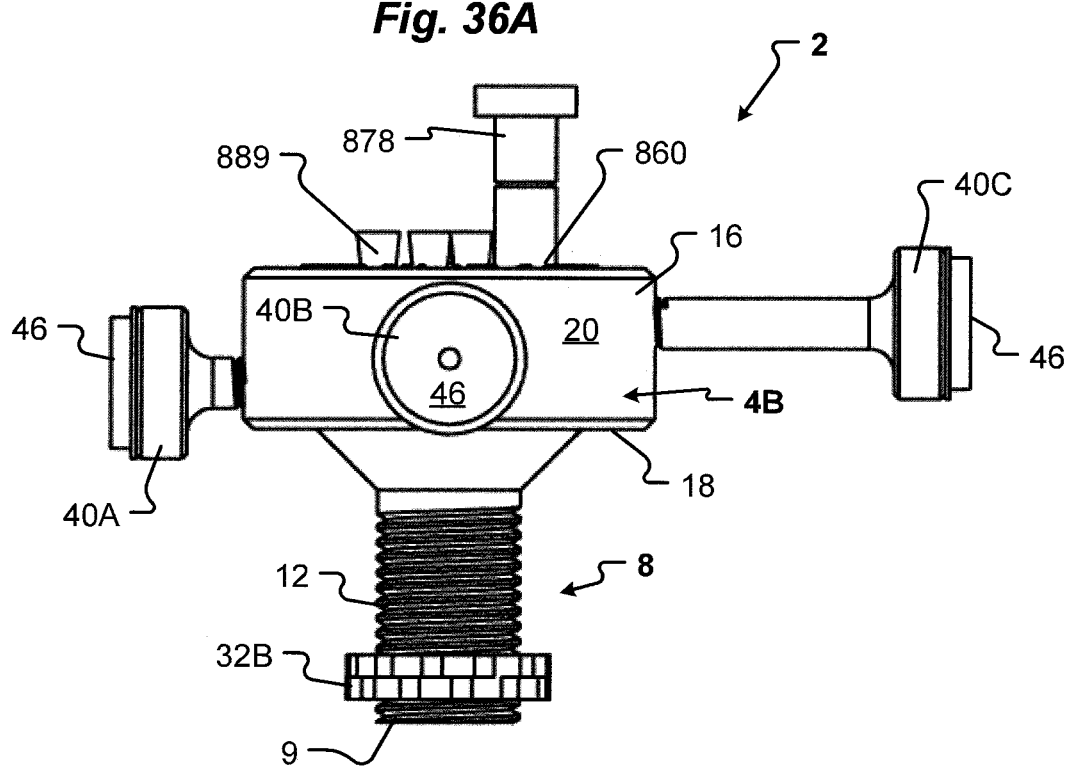
Figure 37:
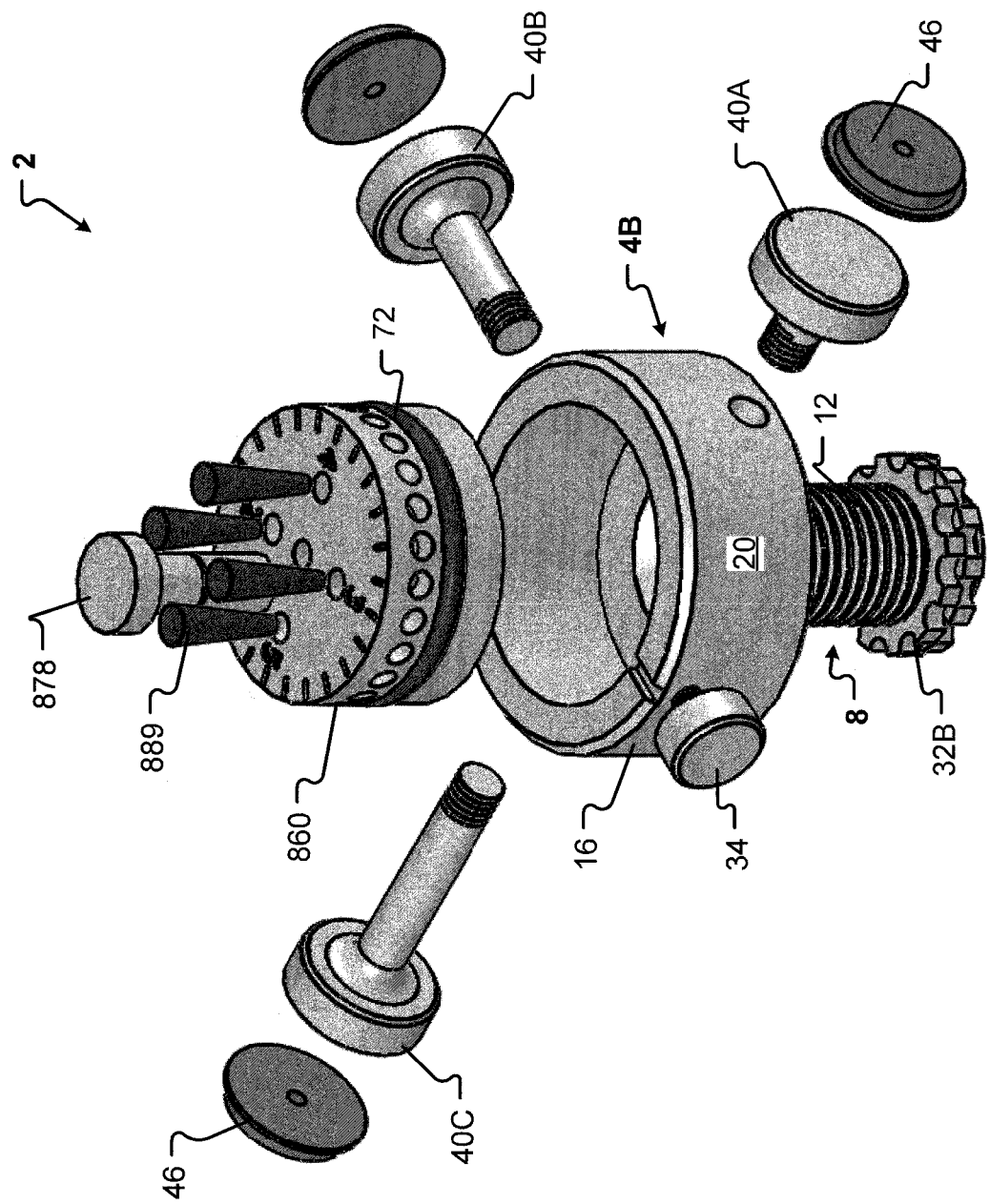
FIG. 37 is an exploded view of a cranial guide of the present disclosure and comprising a slant cannula of FIGS. 34-35 and a cranial port of FIGS. 2-3.
Figure 38B:
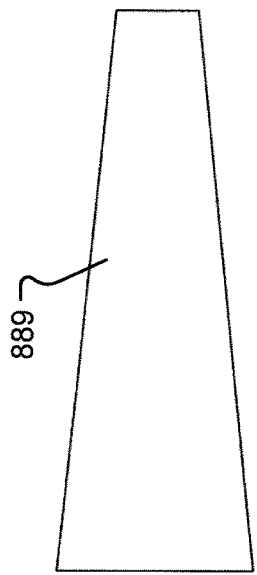
FIG. 38 provides views of a plug of the present disclosure which is configured to seal a channel of the slant cannula.
Figure 38D:
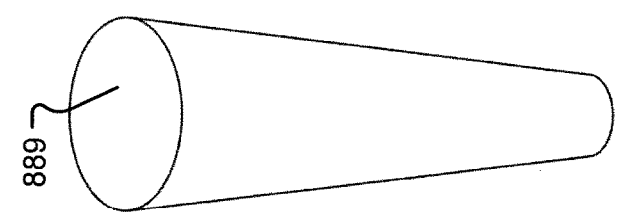
Figure 38A:
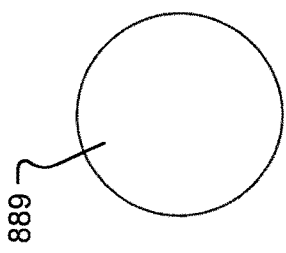
Figure 38C:
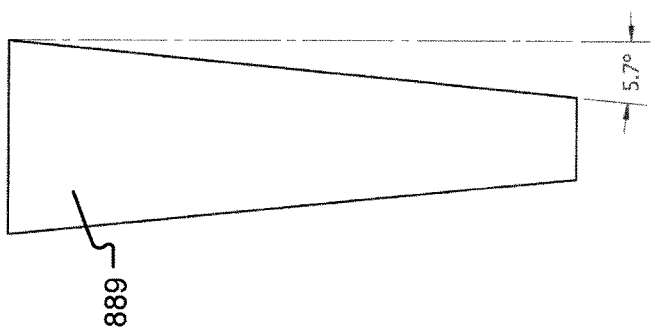

Referring now to FIGS. 36-37, the slant cannula 860 is illustrated with a port 4. A plug 889, further illustrated in FIG. 38, may be positioned in one or more of the channels 880. In this manner, four of the channels 880 may be sealed with a plug while one channel 880 is used to guide a catheter to a targeted portion of the patient's anatomy. In one embodiment, the plugs 889 are formed of silicone or a similar material.

FIGS. 39A-39D are graphs of portions of a patient's brain that may be targeted using the slant cannula 860, such as to reach a hematoma in disparate portions of the patient's brain. More specifically, the graphs illustrate a range of coverage of a tool guided through the channels 880 to particular depths. The shaded areas 892 of the graphs are areas that can be directly reached by a tool as the cannula 860 is rotated around the longitudinal axis 864 of the cannula 860 within the port 4.

Figure 39B:
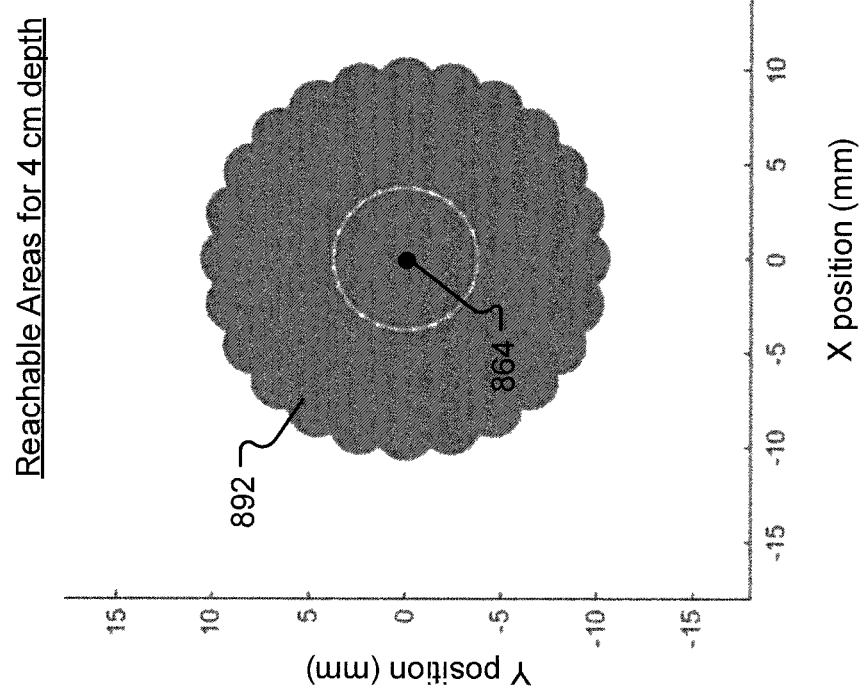
FIGS. 39A-39D are graphs of areas reachable by instruments guided through channels of the slant cannula of FIGS. 34-35.

The graphs relate to an embodiment of a cannula 860 including 24 apertures for locking the cannula to the port. Accordingly, as shown in FIG. 39D, 24 shaded areas 892A-892X are illustrated in an outer ring 894E which are associated with tool guided through channel 880E. White areas within the graphs correspond to areas that cannot be directed reached by a tool guided by a channel 880 of slant cannula 860. However, a hematoma that falls at least partially in a white area can still be evacuated by a nearby catheter position since the space between all reachable areas is not greater than about 2.5 mm at most.

Figure 39A:
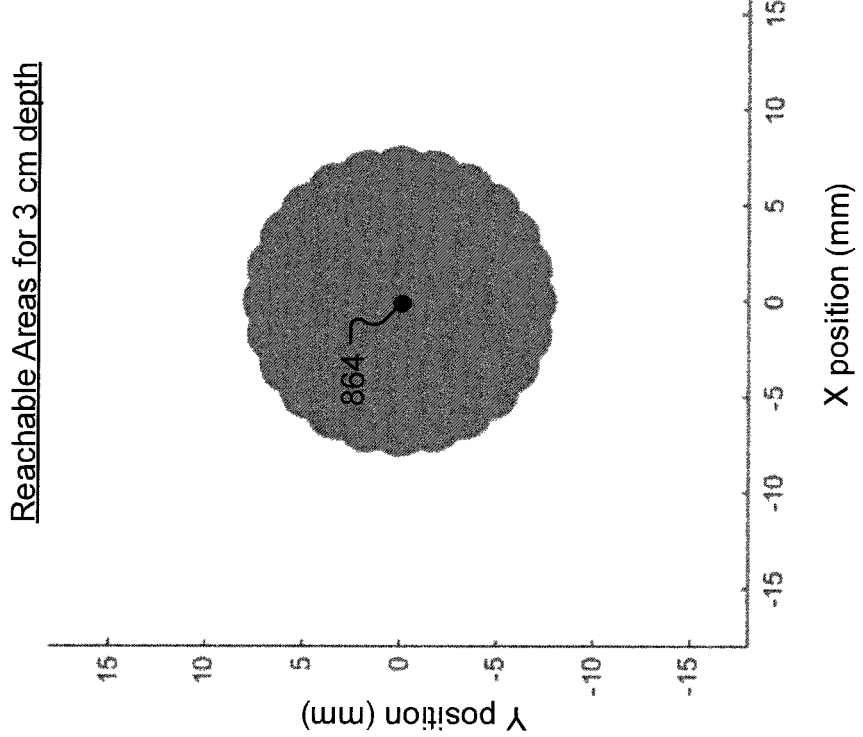
Figure 39D:
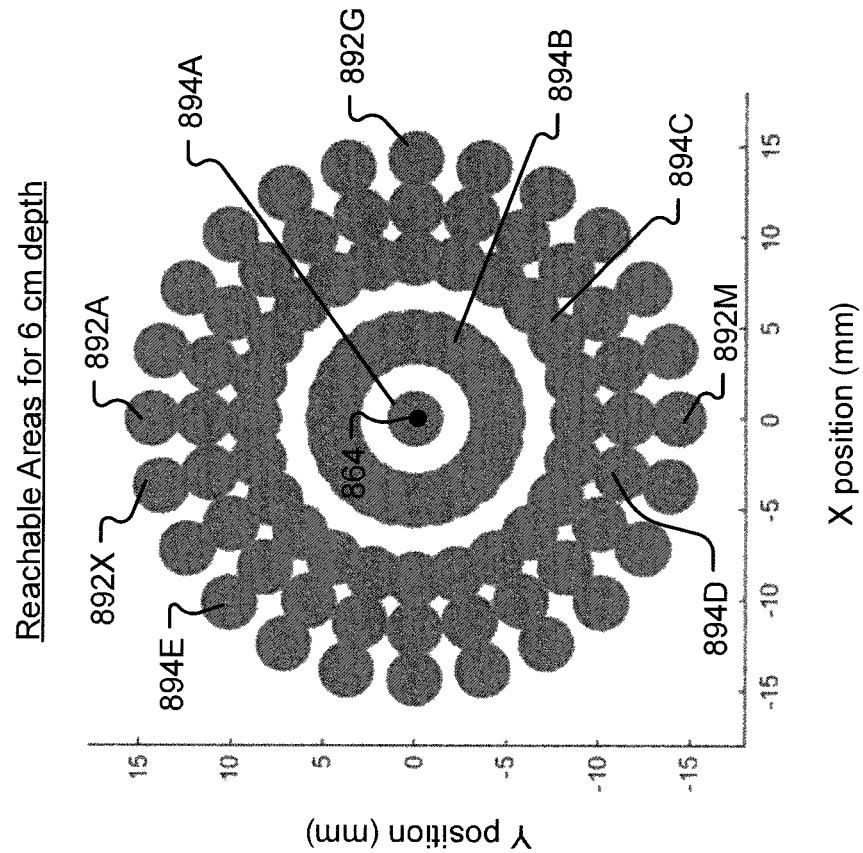

FIG. 39A illustrates coverage of areas 892 along an x-axis and a y-axis which are perpendicular to the longitudinal axis 864 when the tool extends up to about 3 cm through a distal end 9 of the stem 8 of port 4. In FIG. 39, the longitudinal axis 864 is perpendicular to the plane defined by the x- and y-axes and substantially centered at the point (0,0).

Figure 39C:
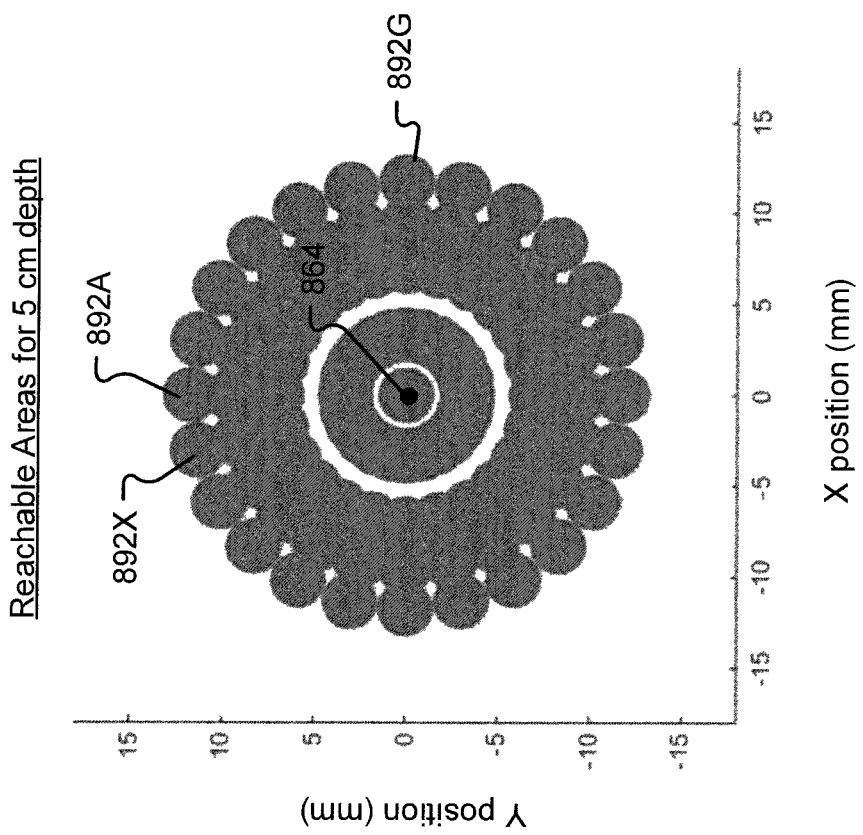

FIG. 39B illustrates areas 892 reachable when the tool is extended up to above 4 cm through the distal end 9 of the port 4. FIG. 39C is a graph of areas 892 reachable when the tool is extended up to about 5 cm through distal end 9 of the port 4.

Finally, FIG. 39D is still another graph illustrating coverage areas 892 provided by the slant cannula 860 when the tool is extended up to about 6 cm through the distal end 9 of the port 4. FIG. 39D also generally illustrates rings 894 associated with each of the channels. More specifically, ring 894A is associated with channel 880A. Similarly, rings 894B-894E are associated with channels 880B-880E respectively. To decrease the spacing between shaded areas 892 of the outer two rings 894D-894E associated with channels 880D-880E, more apertures 868 can be formed in the head 866. Additionally, or alternatively, one or more additional key holes 24 may be formed through the sidewall 20 of the port 4. In either or both of these ways, the number of orientations of the slant cannula 860 with respect to the head 16 of the port can be increased.

Figure 40:
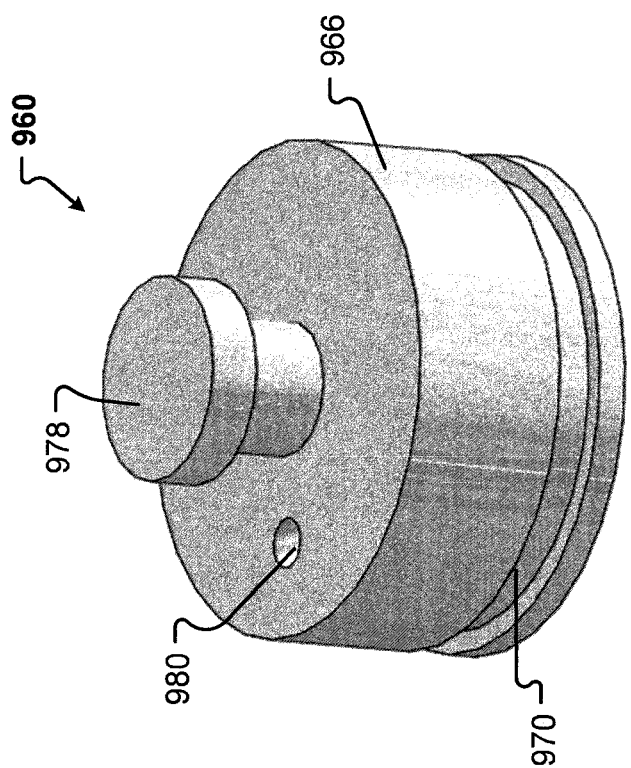
FIG. 40 is a perspective view of a cannula with a single channel of one embodiment of the present disclosure.

Referring now to FIG. 40, a single slant cannula 960 of the present disclosure is illustrated. The single slant cannula 960 is similar to slant cannula 860 and thus has a similar shape and size. However, single slant cannula 960 has a single channel 980. The channel 980 may be formed at an angle equivalent to the angle of one of channels 880A-880E. In one embodiment, the channel 980 is formed at an angle of between about 0° and about 15.5° relative to a longitudinal axis of the single slant cannula 960. Alternatively, the channel 980 may have an angle of between about 15° and about 18° with respect to a longitudinal axis of the cannula 960.

Optionally, in one embodiment, the single slant cannula 960 is manufactured for a particular patient. More specifically, images may be taken of a patient to identify the location of an intracerebral hemorrhage. A medical procedure to relieve the hemorrhage may then be planned, including a location of a burr hole to be formed in the patient's cranium. When the position of the burr hole is determined, an angle of the channel 980 through the single slant cannula 960 can be determined such that the cannula 960 can guide a tool, such as a catheter, to the location of the intracerebral hemorrhage. The cannula 960 may then be manufactured by a suitable method, including a 3D printing method. In this manner, the single slant cannula 960 may include a channel 980 formed at an angle that is specific to a particular procedure to be performed on a patient.

Referring now to FIG. 41, still another cannula 1060 of the present disclosure is illustrated. The cannula 1060 generally includes a head 1066 and a shaft 1062. A lumen 1072 extends through the head and shaft. In one embodiment, the walls of the lumen 1072 are angled at between about 4° and 6° with respect to a longitudinal axis of the cannula 1060.

A pivot 1074 is positioned in the cannula 1060 within the shaft 1076. The pivot 1074 can optionally rotate axially around the longitudinal axis. Additionally, the pivot 1074 may be rotated around a pivot axis substantially perpendicular to the longitudinal axis 1064. In one embodiment, the pivot 1074 can rotate between about −6° to about +6° with respect to the pivot axis. Optionally, the pivot 1074 is a ball joint.

In one embodiment, the pivot 1074 is positioned a predetermined distance from a distal end 1063 of the shaft 1062 such that the pivot 1074 is at least partially below the exterior surface of a patient's cranium when the cannula 1060 is received by a port 4 anchored in the patient's cranium. In another embodiment, at least a portion of the pivot 1074 extends below an interior portion of the patient's cranium when the cannula is in the port 4.

A shaft 1076 extends distally and proximally from the pivot 1074 within the cannula 1060. A channel 1080 is formed through the shaft 1076. The channel 1080 has the same, or similar, dimensions to other channels 180-980 of the present disclosure. O-rings 72A and channel plugs 186 may also be used with channel 1080 to ensure a seal between a catheter guided through the channel 1080 and the cannula 1060.

Referring now to FIG. 42, an arc guided cannula 1160 of the present disclosure is generally illustrated. The arc guided cannula 1160 is sized to be received by a port 4 of the present disclosure, such as port 4A. The arc guide cannula 1160 is similar to cannula 860, 960 and is configured for use in similar medical procedures. Thus, cannula 1160 has a similar size and shape as cannula 860, 960.

Cannula 1160 generally includes a head 1166 with a tapered channel 1180. The tapered channel 1180 is configured to guide a catheter to a targeted portion of the patient's anatomy. More specifically, the tapered channel 1180 has a width that is equal to the diameter of channels 180-1080 described herein. A proximal portion of the tapered channel 1180 has a cross-sectional length that is greater than a distal portion of the tapered channel. Accordingly, a cross-section of the tapered channel 1180 has the shape of a truncated triangle with the base of the triangle positioned distal to the stem 8 of port 4.

A guide arm 1190 is selectively interconnectable to the port 4. The guide arm 1190 may be rotated or otherwise moved with respect to the cannula 1160 to guide a catheter through the tapered channel 1180 at a predetermined angle. In one embodiment, the guide arm 1180 can align a catheter at angles of between about 0° and about 15° with respect to a longitudinal axis of the port 4.

While various embodiments of the disclosure have been described in detail, it is apparent that modifications and alterations of those embodiments will occur to those skilled in the art. However, it is to be expressly understood that such modifications and alterations are within the scope and spirit of the present disclosure, as set forth in the following claims. Further, the aspects and embodiments described herein are capable of other embodiments and of being practiced or of being carried out in various ways. In addition, it is to be understood that the phraseology and terminology used herein is for the purpose of description and should not be regarded as limiting. The use of "including," "comprising," or "having," and variations thereof, is meant to encompass the items listed and equivalents thereof, as well as additional items.

What is claimed is:

1. A cranial guide for an intracranial medical procedure to be performed on a patient, comprising:
   a cranial port including:
      a stem that is generally cylindrical and configured to be anchored in a burr hole to be formed in the patient's cranium;
      a cap including a distal surface interconnected to the stem, a sidewall portion extending proximally from the distal surface, and a chamber;
      a lumen having an interior diameter which extends through the stem to the chamber to define a passage through the cranial port; and
      a key hole extending through the cap sidewall portion;
   a guide cannula including:
      a head having a sidewall portion and a proximal portion, the head adapted to be received within the chamber of the cap, wherein the guide cannula can be rotated axially with respect to the cranial port;
      a plurality of apertures spaced around the sidewall portion of the head, each of the apertures alignable with the key hole; and
      at least one channel extending through the head and including a distal outlet; and
   a fixture configured to extend at least partially through the key hole into any of the plurality of apertures aligned with the key hole to prevent rotation of the guide cannula with respect to the cranial port.

2. The cranial guide of claim 1, wherein the at least one channel is configured to guide an instrument to a target within the patient's cranium.

3. The cranial guide of claim 1, wherein the at least one channel includes at least one of:
   a first channel at a first angle with respect to a longitudinal axis of the guide cannula;
   a second channel at a second angle with respect to the longitudinal axis;
   a third channel at a third angle with respect to the longitudinal axis;
   a fourth channel at a fourth angle with respect to the longitudinal axis; and
   a fifth channel substantially parallel to the longitudinal axis.

4. The cranial guide of claim 3, wherein the at least one channel includes the first, second, third, and fourth channels, wherein rotating the guide cannula with respect to the cranial port alters a trajectory of a distal outlet of each of the first, second, third, and fourth channels.

5. The cranial guide of claim 1, wherein the guide cannula further comprises a shaft interconnected to a distal portion of the head, the shaft including an exterior diameter which is not greater than the lumen interior diameter, and wherein the channel extends through the shaft.

6. The cranial guide of claim 5, wherein the distal outlet of the channel extends through a sidewall of the shaft.

7. The cranial guide of claim 5, further comprising an indicia on the proximal portion of the head to indicate the trajectory of the distal outlet of the channel.

8. The cranial guide of claim 5, wherein the shaft has a predetermined length such that when the head is received within the chamber, a distal end of the shaft extends a predetermined distance beyond a distal end of the stem.

9. The cranial guide of claim 1, wherein the guide cannula further comprises a connector extending from the proximal portion of the head, the connector configured to interconnect a tube to the at least one channel of the guide cannula.

10. The cranial guide of claim 1, wherein the guide cannula further comprises a boss extending from the proximal portion for manipulating the guide cannula.

11. The cranial guide of claim 1, wherein the cranial port further comprises at least one tap extending at least partially into the cap sidewall portion, the tap configured to receive a marker.

12. The cranial guide of 11, wherein the at least one tap comprises three taps having a predetermined spacing in the cap sidewall portion, a first one of the three taps configured to receive a first marker, a second one of the three taps configured to receive a second marker, and a third one of the three taps configured to receive a third marker.

13. The cranial guide of claim 1, further comprising threads on the stem configured to anchor the cranial port in the burr hole.

14. The cranial guide of claim 1, wherein the stem has a predetermined length such that when the cranial port is anchored in the burr hole in the patient's cranium, the distal surface of the cap is spaced from the patient's scalp.

15. The cranial guide device of claim 14, further comprising a depth set element releasably interconnectable to the stem such that, when the cranial port is anchored in the burr hole in the patient's cranium, a distal end of the stem is a predetermined distance from the patient's scalp.

16. The cranial guide device of claim 1, wherein the plurality of apertures comprises 24 apertures spaced substantially equidistant around the sidewall portion of the head.

* * * * *